(12) United States Patent
Li et al.

(10) Patent No.: US 10,544,239 B2
(45) Date of Patent: *Jan. 28, 2020

(54) ORGANOSILICA MATERIALS AND USES THEREOF

(71) Applicant: ExxonMobil Research and Engineering Company, Annandale, NJ (US)

(72) Inventors: Quanchang Li, Dayton, NJ (US); David Charles Calabro, Bridgewater, NJ (US); Mobae Amin Afeworki, Phillipsburg, NJ (US); Simon Christopher Weston, Annandale, NJ (US); Matcheld Maria Wilfried Mertens, Flemington, NJ (US); Tilman Wolfram Beutel, Neshanic Station, NJ (US); Wenyih Frank Lai, Bridgewater, NJ (US); Paul Podsiadlo, Easton, PA (US); Jean Willem Lodewijk Beeckman, Columbia, MD (US)

(73) Assignee: EXXONMOBILE RESEARCH AND ENGINEERING COMPANY, Annandale, NJ (US)

( * ) Notice: Subject to any disclaimer, the term of this patent is extended or adjusted under 35 U.S.C. 154(b) by 317 days.

This patent is subject to a terminal disclaimer.

(21) Appl. No.: 14/966,015

(22) Filed: Dec. 11, 2015

(65) Prior Publication Data
US 2016/0229959 A1 Aug. 11, 2016

Related U.S. Application Data

(60) Provisional application No. 62/091,071, filed on Dec. 12, 2014, provisional application No. 62/091,077, filed on Dec. 12, 2014.

(51) Int. Cl.
*C10G 45/52* (2006.01)
*B01D 15/00* (2006.01)
(Continued)

(52) U.S. Cl.
CPC ............. *C08F 10/02* (2013.01); *B01D 15/00* (2013.01); *B01D 53/02* (2013.01); *B01D 53/047* (2013.01); *B01D 53/0462* (2013.01); *B01D 53/228* (2013.01); *B01J 20/06* (2013.01); *B01J 20/08* (2013.01); *B01J 20/10* (2013.01); *B01J 20/103* (2013.01); *B01J 20/264* (2013.01); *B01J 20/286* (2013.01); *B01J 20/28011* (2013.01); *B01J 20/28057* (2013.01); *B01J 20/28069* (2013.01); *B01J 20/28078* (2013.01); *B01J 20/3042* (2013.01); *B01J 20/3236* (2013.01); *B01J 20/3238* (2013.01); *B01J 23/42* (2013.01); *B01J 23/44* (2013.01); *B01J 29/0325* (2013.01); *B01J 31/06* (2013.01); *B01J 31/125* (2013.01); *B01J 31/127* (2013.01); *B01J 35/1019* (2013.01); *B01J 35/1023* (2013.01); *B01J 35/1028* (2013.01); *B01J 35/1042* (2013.01); *B01J 35/1061* (2013.01); *B01J 37/036* (2013.01); *C01B 37/00* (2013.01); *C01B 39/00* (2013.01); *C07F 7/00* (2013.01); *C08F 2/00* (2013.01); *C08F 2/10* (2013.01); *C08F 2/42* (2013.01); *C08F 4/65916* (2013.01); *C08F 4/65925* (2013.01); *C08G 77/50* (2013.01); *C08G 77/58* (2013.01); *C08G 77/60* (2013.01); *C10G 25/003* (2013.01); *C10G 35/06* (2013.01); *C10G 45/00* (2013.01); *C10G 45/04* (2013.01); *C10G 45/34* (2013.01); *C10G 45/44* (2013.01); *C10G 45/46* (2013.01); *C10G 45/60* (2013.01); *C10G 45/64* (2013.01); *C10G 47/02* (2013.01); *C10G 50/00* (2013.01); *C10K 1/32* (2013.01); *C10M 101/02* (2013.01); *C10M 177/00* (2013.01); *B01D 2253/106* (2013.01); *B01D 2253/204* (2013.01);
(Continued)

(58) Field of Classification Search
None
See application file for complete search history.

(56) References Cited

U.S. PATENT DOCUMENTS

| 3,178,392 A | 4/1965 | Kriner |
| 4,218,308 A | 8/1980 | Itoh et al. |

(Continued)

FOREIGN PATENT DOCUMENTS

| CN | 101804335 A | 8/2010 |
| CN | 101980013 A | 2/2011 |

(Continued)

OTHER PUBLICATIONS

Topchiev et al., "Preparation of hexa alkoxy derivatives of cyclotrimethylenesilane", Doklady Akademii Nauk SSSR, 1955, pp. 95-96. vol. 103.
Kriner, "The preparation of cyclic siliconmethylene compounds", Journal of Organic Chemistry, Jun. 1964, pp. 1601-1606, vol. 29.
Kuivila et al., "Trimethylsilyl-substituted norbornenes, norbornanes, and nortricyclene", Journal of Organic Chemistry, Oct. 1964, pp. 2845-2851, vol. 29.
Vidal-Madjar et al., "Fast Analysis of Geometrical Isomers of Complex Compounds by Gas-Solid Chromatography", Gas Chromatography, Sep. 28, 1970—Oct. 2, 1970, pp. 381-386.
(Continued)

*Primary Examiner* — Yun Qian
(74) *Attorney, Agent, or Firm* — Priya G. Prasad

(57) ABSTRACT

Organosilica materials, which are a polymer of at least one independent monomer of Formula $[Z^1OZ^2OSiCH_2]_3$ (I), wherein each $Z^1$ and $Z^2$ independently represent a hydrogen atom, a $C_1$-$C_4$ alkyl group or a bond to a silicon atom of another monomer and at least one other trivalent metal oxide monomer are provided herein. Methods of preparing and processes of using the organosilica materials, e.g., for catalysis etc., are also provided herein.

19 Claims, 22 Drawing Sheets

(51) Int. Cl.

| | | |
|---|---|---|
| C08F 10/02 | (2006.01) | |
| B01J 31/06 | (2006.01) | |
| B01J 35/10 | (2006.01) | |
| C08G 77/58 | (2006.01) | |
| C08G 77/50 | (2006.01) | |
| B01J 20/08 | (2006.01) | |
| B01J 20/28 | (2006.01) | |
| B01J 37/03 | (2006.01) | |
| B01J 20/06 | (2006.01) | |
| B01J 20/10 | (2006.01) | |
| B01J 20/26 | (2006.01) | |
| B01J 20/286 | (2006.01) | |
| B01J 20/30 | (2006.01) | |
| B01J 20/32 | (2006.01) | |
| B01D 53/22 | (2006.01) | |
| B01J 23/42 | (2006.01) | |
| B01J 31/12 | (2006.01) | |
| C01B 37/00 | (2006.01) | |
| C01B 39/00 | (2006.01) | |
| C08G 77/60 | (2006.01) | |
| C08F 2/00 | (2006.01) | |
| C08F 2/10 | (2006.01) | |
| C08F 2/42 | (2006.01) | |
| C10G 25/00 | (2006.01) | |
| C10G 35/06 | (2006.01) | |
| C10G 45/00 | (2006.01) | |
| C10G 45/04 | (2006.01) | |
| C10G 45/34 | (2006.01) | |
| C10G 45/44 | (2006.01) | |
| C10G 45/46 | (2006.01) | |
| C10G 45/60 | (2006.01) | |
| C10G 45/64 | (2006.01) | |
| C10G 47/02 | (2006.01) | |
| C10G 50/00 | (2006.01) | |
| C10M 177/00 | (2006.01) | |
| C10K 1/32 | (2006.01) | |
| B01J 29/03 | (2006.01) | |
| B01D 53/04 | (2006.01) | |
| B01D 53/047 | (2006.01) | |
| B01D 53/02 | (2006.01) | |
| B01J 23/44 | (2006.01) | |
| C10M 101/02 | (2006.01) | |
| C07F 7/00 | (2006.01) | |
| C08F 4/659 | (2006.01) | |
| C08F 4/6592 | (2006.01) | |

(52) U.S. Cl.
CPC .. *B01D 2253/306* (2013.01); *B01D 2253/308* (2013.01); *B01D 2253/311* (2013.01); *B01D 2256/245* (2013.01); *B01D 2257/102* (2013.01); *B01D 2257/302* (2013.01); *B01D 2257/304* (2013.01); *B01D 2257/306* (2013.01); *B01D 2257/404* (2013.01); *B01D 2257/504* (2013.01); *B01D 2257/702* (2013.01); *B01D 2257/80* (2013.01); *B01J 35/1038* (2013.01); *B01J 35/1047* (2013.01); *B01J 35/1057* (2013.01); *B01J 2220/86* (2013.01); *B01J 2231/641* (2013.01); *B01J 2231/646* (2013.01); *C10M 2203/1006* (2013.01); *C10N 2270/00* (2013.01)

(56) References Cited

U.S. PATENT DOCUMENTS

| | | |
|---|---|---|
| 5,630,937 A | 5/1997 | Betz et al. |
| 5,719,322 A | 2/1998 | Lansbarkis et al. |
| 7,300,905 B2 | 11/2007 | Keefer et al. |
| 7,497,965 B2 | 3/2009 | Wariishi et al. |
| 7,538,065 B2 | 5/2009 | McCarthy et al. |
| 7,682,502 B2 | 3/2010 | McCarthy et al. |
| 7,705,062 B2 | 4/2010 | Markowitz et al. |
| 7,754,330 B2 | 7/2010 | Hamada et al. |
| 7,767,620 B2 | 8/2010 | Whitnall et al. |
| 7,947,799 B2 | 5/2011 | Landskron et al. |
| 8,110,692 B2 | 2/2012 | Bellussi et al. |
| 8,211,498 B2 | 7/2012 | Ku et al. |
| 8,277,600 B2 | 10/2012 | Hamada et al. |
| 8,277,661 B2 | 10/2012 | Sah et al. |
| 8,425,762 B2 | 4/2013 | McCarthy et al. |
| 8,441,006 B2 | 5/2013 | Mchalak et al. |
| 8,470,074 B2 | 6/2013 | Baugh et al. |
| 8,545,694 B2 | 10/2013 | McCarthy et al. |
| 8,562,856 B2 | 10/2013 | Giannantonio et al. |
| 8,568,520 B2 | 10/2013 | Ohashi et al. |
| 8,598,070 B1 | 12/2013 | Baugh et al. |
| 8,598,071 B1 | 12/2013 | Baugh et al. |
| 8,809,561 B2 | 8/2014 | Bellussi et al. |
| 9,181,282 B2 | 11/2015 | Ide et al. |
| 2003/0188991 A1 | 10/2003 | Shan et al. |
| 2005/0093189 A1 | 5/2005 | Vo |
| 2006/0058565 A1 | 3/2006 | DeWild |
| 2006/0070917 A1 | 4/2006 | McCarthy et al. |
| 2006/0165574 A1 | 7/2006 | Sayari |
| 2007/0034992 A1 | 2/2007 | Wariishi et al. |
| 2007/0054136 A1 | 3/2007 | Takahashi et al. |
| 2007/0112242 A1 | 5/2007 | Edmiston |
| 2007/0173401 A1 | 7/2007 | Landskron et al. |
| 2009/0130412 A1 | 5/2009 | Hatton et al. |
| 2009/0215612 A1 | 8/2009 | McCarthy et al. |
| 2009/0294922 A1 | 12/2009 | Hamada et al. |
| 2010/0155302 A1 | 6/2010 | Kaminsky et al. |
| 2010/0233482 A1 | 9/2010 | Hamada et al. |
| 2011/0139685 A1 | 6/2011 | McCarthy et al. |
| 2011/0190115 A1 | 8/2011 | Ciriminna et al. |
| 2012/0059181 A1* | 3/2012 | Bellussi ............. C01B 37/00 556/10 |
| 2012/0160742 A1 | 6/2012 | Sohn et al. |
| 2013/0075876 A1 | 3/2013 | Goethals et al. |
| 2013/0078172 A1 | 3/2013 | Li et al. |
| 2013/0249049 A1 | 9/2013 | Michalak et al. |
| 2014/0004358 A1 | 1/2014 | Blackwell et al. |
| 2014/0186246 A1 | 7/2014 | Calabro et al. |
| 2014/0208753 A1 | 7/2014 | Liu et al. |
| 2015/0011787 A1 | 1/2015 | Bellussi et al. |
| 2018/0142066 A1 | 5/2018 | Falkowski et al. |

FOREIGN PATENT DOCUMENTS

| | | |
|---|---|---|
| CN | 102052713 A | 5/2011 |
| CN | 102643429 A | 8/2012 |
| CN | 103157362 A | 6/2013 |
| CN | 103495340 A | 1/2014 |
| CN | 103613975 A | 3/2014 |
| CN | 104117343 A | 10/2014 |
| EP | 1995214 A2 | 11/2008 |
| JP | H10151343 A | 6/1998 |
| JP | H11295284 A | 10/1999 |
| JP | 2003167233 A | 6/2003 |
| JP | 2006083311 A | 3/2006 |
| JP | 2006095512 A | 4/2006 |
| JP | 2007070520 A | 3/2007 |
| JP | 2007238761 A | 9/2007 |
| JP | 2008045060 A | 2/2008 |
| JP | 2008062138 A | 3/2008 |
| JP | 2010100492 A | 5/2010 |
| JP | 2011025201 A | 2/2011 |
| JP | 2012149138 A | 8/2012 |
| JP | 2014057941 A | 4/2014 |
| JP | 5544672 B1 | 7/2014 |
| RU | 2291878 C1 | 1/2007 |
| WO | 9610537 A1 | 4/1996 |
| WO | 2006032140 A1 | 3/2006 |
| WO | 2007081212 A1 | 7/2007 |
| WO | 2008143385 A1 | 11/2008 |
| WO | 2010106408 A1 | 9/2010 |

(56) References Cited

FOREIGN PATENT DOCUMENTS

| WO | 2011145933 A1 | 11/2011 |
|---|---|---|
| WO | 2013093022 A1 | 6/2013 |
| WO | 2014010512 A1 | 1/2014 |
| WO | 2014090757 A1 | 6/2014 |

OTHER PUBLICATIONS

Niemeyer et al., "Effects of CO2 Sorption on the Rotational Reorientation Dynamics of a Model Solute Dissolved in Molten Poly(dimethylsiloxane)", Macromolecules, Jan. 13, 1998, pp. 77-85, vol. 31.

Shinji et al., "Novel Mesoporous Materials with a Uniform Distribution of Organic Groups and Inorganic Oxide in Their Frameworks", Journal of the American Chemical Society, Oct. 4, 1999, pp. 9611-9614, vol. 121.

Melde et al., "Mesoporous Sieves with Unified Hybrid Inorganic/Organic Frameworks", Chemistry of Materials, Oct. 9, 1999, pp. 3302-3308, vol. 11.

Eliseeva et al., "Antifoaming additive for alkaline absorption solutions for removal of carbon dioxide from synthesis gas", Khimicheskaya Promyshlennost, 1999, pp. 632-633, vol. 10.

Brondani, et al., "Polyfunctional carbosilanes and organosilicon compounds. Synthesis via Grignard reactions", Tetrahedron Letters, Mar. 2, 2001, pp. 2111-2114, vol. 34.

Gilman et al., "Reactions of triphenylsilyllithium with some dichloropropenes", Journal of Organometallic Chemistry, Apr. 13, 2001, pp. 293-303, vol. 2.

Landskron et al., "Periodic Mesoporous Organosilicas Containing Interconnected [Si(CH2)]3 Rings", Science, Oct. 10, 2003, pp. 266-269, vol. 302.

Harlick et al., "Applications of Pore-Expanded Mesoporous Silica. 5. Triamine Grafted Material with Exceptional CO2 Dynamic and Equilibrium Adsorption Performance", Industrial & Engineering Chemistry Research, Dec. 20, 2006, pp. 446-458 vol. 46.

Grudzien et al., "Cage-like ordered mesoporous organosilicas with isocyanurate bridging groups: Synthesis, template removal and structural properties", Microporous and Mesoporous Materials, pp. 68-77, vol. 118, No. 1-3.

Walcarius et al., "Mesoporous organosilica adsorbents: nanoengineered materials for removal of organic and inorganic pollutants", Journal of Materials Chemistry, Jan. 1, 2010, pp. 4478-4511, vol. 20, No. 22.

Vidal et al., "Adsorption of polycyclic aromatic hydrocarbons from aqueous solutions by modified periodic mesoporous organosilica", Journal of Colloid and Interface Science, Feb. 3, 2011, pp. 466-473, vol. 357, No. 2.

Goethals et al., "Ultra-low-k cyclic carbon-bridged PMO films with a high chemical resistance", Journal of Materials Chemistry, Feb. 21, 2012, pp. 8281-8286, vol. 22.

PCT/US2015/065258 Partial International Search Report and Written Opinion dated Mar. 16, 2016.

PCT/US2015/065194 International Search Report and Written Opinion dated Mar. 29, 2016.

PCT/US2015/065191 International Search Report and Written Opinion dated Mar. 29, 2016.

PCT/US2015/065306 International Search Report and Written Opinion dated Mar. 29, 2016.

PCT/US2015/065219 International Search Report and Written Opinion dated Apr. 5, 2016.

PCT/US2015/065283 International Search Report and Written Opinion dated Apr. 6, 2016.

PCT/US2015/065199 International Search Report and Written Opinion dated Apr. 8, 2016.

PCT/US2015/065204 International Search Report and Written Opinion dated Apr. 8, 2016.

PCT/US2015/065225 International Search Report and Written Opinion dated Apr. 8, 2016.

Grudzien et al., "Cage-like mesoporous organosilicas with isocyanurate bridging groups synthesized by soft templating with poly(ethylene oxide)-poly(butylene oxide)-poly(ethylene oxide) block copolymer", Journal of Colloid and Interface Science, May 1, 2009, pp. 354-362, vol. 333, No. 1, Elsevier.

Grudzien et al., "Periodic Mesoporous Organosilicas with Im3m Symmetry and Large Isocyanurate Bridging Groups", The Journal of Physical Chemistry B, Feb. 1, 2006, pp. 2972-2975, vol. 110, No. 7, ACS Publications.

Olkhovyk et al., "Periodic Mesoporous Organosilica with Large Heterocyclic Bridging Groups", Journal of American Chemical Society, Jan. 1, 2005, pp. 60-61, vol. 127, No. 1, ACS Publications.

Poli et al., "Different Routes for Preparing Mesoporous Organosilicas Containing the Troger's Base and Their Textural and Catalytic Implications", The Journal of Physical Chemistry C, Apr. 21, 2011, pp. 7573-7585, vol. 115, No. 15, ACS Publications.

PCT/US2015/065208 International Search Report and Written Opinion dated May 17, 2016.

PCT/US2015/065200 Partial International Search Report and Written Opinion dated May 23, 2016.

Diaz et al., "Hybrid organic-inorganic catalytic porous materials synthesized at neutral pH in absence of structural directing agents", Journal of Materials Chemistry, Jan. 1, 2009, pp. 5970-5979, vol. 19, No. 33, Royal Society of Chemistry.

Reale et al., "A fluoride-catalyzed sol-gel route to catalytically active non-ordered mesoporous silica materials in the absence of surfactants", Journal of Materials Chemistry, Jan. 1, 2005, pp. 1742-1754, vol. 15, No. 17, Royal Society of Chemistry.

PCT/US2015/065200 Partial International Search Report and Written Opinion dated Jul. 18, 2016.

Goethals, et al., "A new procedure to seal the pores of mesoporous low-k films with precondensed organosilica oligomers", Chemical Communications, 2012, pp. 2797-2799, vol. 48, No. 22, Royal Society of Chemistry.

Goethals et al., "Sealed ultra low-k organosilica films with improved electrical, mechanical and chemical properties", Journal of Materials Chemistry C, 2013, vol. 1, No. 25, Royal Society of Chemistry.

Goethals et al., "Hydrophobic high quality ring PMOs with an extremely high stability", Journal of Materials Chemistry, 2010, pp. 1709-1716, vol. 20, No. 9, Royal Society of Chemistry.

Landskron et al., "Periodic Mesoporous Organosilicas: Self-Assembly from Bridged Cyclic Silsesquioxane Precursors", Angewandte Chemie, International Edition, 2005, pp. 2107-2109, vol. 44, No. 14, Wiley-VCH Verlag GmbH & Co. KgaA.

* cited by examiner

ORGANOSILICA MATERIALS AND USES THEREOF

CROSS-REFERENCE TO RELATED APPLICATIONS

This application claims the benefit of provisional U.S. Ser. No. 62/091,071 and provisional U.S. Ser. No. 62/091,077, filed Dec. 12, 2014, the entire contents of which are expressly incorporated by reference herein.

This application is also related to several other co-pending U.S. applications, filed on even date herewith and bearing Application Nos. 14/965,992 (entitled "Organosilica Materials and Uses Thereof"), 14/966,001 (entitled "Methods of Producing Organosilica Materials and Uses Thereof"), 14/966,071 (entitled "Aromatic Hydrogenation Catalysts and Uses Thereof"), 14/965,984 (entitled "Organosilica Materials and Uses Thereof"), 14/966,383 (entitled "Organosilica Materials and Uses Thereof"), 14/966,284 (entitled "Organosilica Materials and Uses Thereof"), 14/966,407 (entitled "Coating Method Using Organosilica Materials and Uses Thereof"), 14/966,445 (entitled "Membrane Fabrication Method Using Organosilica Materials and Uses Thereof"), 14/966,534 (entitled "Adsorbent for Heteroatom Species Removal and Uses Thereof"), and 14/966,790 (entitled "Method for Separating Aromatic Compounds from Lube Basestocks"), the entire disclosures of each of which are incorporated by reference herein.

Additionally, this application is further related to several other co-pending U.S. applications, filed on even date herewith and bearing Application Nos. 15/526,512 (entitled "Organosilica Materials for Use as Adsorbents for Oxygenate Removal"), 15/526,524 (entitled "Supported Catalyst for Olefin Polymerization"), 15/526,529 (entitled "Supported Catalyst for Olefin Polymerization"), 15/526,513 (entitled "Supported Catalyst for Olefin Polymerization"), and 15/526,521 (entitled "Supported Catalyst for Olefin Polymerization"), the entire disclosures of each of which are incorporated by reference herein.

FIELD OF THE INVENTION

The present invention relates to organosilica materials, methods of making and uses thereof.

BACKGROUND OF THE INVENTION

Porous inorganic solids have found great utility as catalysts and separation media for industrial application. In particular, mesoporous materials, such as silicas and aluminas, having a periodic arrangement of mesopores are attractive materials for use in adsorption, separation and catalysis processes due to their uniform and tunable pores, high surface areas and large pore volumes. The pore structure of such mesoporous materials is large enough to absorb large molecules and the pore wall structure can be as thin as about 1 nm. Further, such mesoporous materials are known to have large specific surface areas (e.g., 1000 $m^2/g$) and large pore volumes (e.g., 1 $cm^3/g$). For these reasons, such mesoporous materials enable reactive catalysts, adsorbents composed of a functional organic compound, and other molecules to rapidly diffuse into the pores and therefore, can be advantageous over zeolites, which have smaller pore sizes. Consequently, such mesoporous materials can be useful not only for catalysis of high-speed catalytic reactions, but also as large capacity adsorbents.

It was further discovered that the inclusion of some organic groups in the mesoporous framework can provide adjustable reactive surfaces and also contributes to uniformity in pore size, higher mechanical strength, and hydrothermal stability of the material. Thus, mesoporous organosilica materials can exhibit unique properties compared to mesoporous silica such as enhanced hydrothermal stability, chemical stability, and mechanical properties. Organic groups can be incorporated using bridged silsesquioxane precursors of the form Si—R—Si to form mesoporous organosilicas.

Mesoporous organosilicas are conventionally formed by the self-assembly of the silsequioxane precursor in the presence of a structure directing agent, a porogen and/or a framework element. The precursor is hydrolysable and condenses around the structure directing agent. These materials have been referred to as Periodic Mesoporous Organosilicates (PMOs), due to the presence of periodic arrays of parallel aligned mesoscale channels. For example, Landskron, K., et al. [Science, 302:266-269 (2003)] report the self-assembly of 1,3,5-tris[diethoxysila]cylcohexane [$(EtO)_2SiCH_2$]$_3$ in the presence of a base and the structure directing agent, cetyltrimethylammonium bromide to form PMOs that are bridged organosilicas with a periodic mesoporous framework, which consist of $SiO_3R$ or $SiO_2R_2$ building blocks, where R is a bridging organic group. In PMOs, the organic groups can be homogenously distributed in the pore walls. U.S. Pat. Pub. No. 2012/0059181 reports the preparation of a crystalline hybrid organic-inorganic silicate formed from 1,1,3,3,5,5 hexaethoxy-1,3,5 trisilyl cyclohexane in the presence of $NaAlO_2$ and base. U.S. Patent Application Publication No. 2007/003492 reports preparation of a composition formed from 1,1,3,3,5,5 hexaethoxy-1,3,5 trisilyl cyclohexane in the presence of propylene glycol monomethyl ether.

However, the use of a structure directing agent, such as a surfactant, in the preparation of an organosilica material, such as a PMO, requires a complicated, energy intensive process to eliminate the structure directing agent at the end of the preparation process. This limits the ability to scale-up the process for industrial applications. Therefore, there is a need to provide additional organosilica materials with a desirable pore diameter, pore volume and surface area. Further, there is a need to provide such organosilica materials that can be prepared by a method that can be practiced in the absence of a structure directing agent, a porogen or surfactant.

SUMMARY OF THE INVENTION

It has been found that an organosilica material with desirable pore diameter, pore volume, and surface area can be achieved. Further, such organosilica material can be successfully prepared without the need for a structure directing agent, a porogen or surfactant.

Thus, in one aspect, embodiments of the invention provide an organosilica material, which is a polymer of at least one monomer of Formula [$Z^1OZ^2OSiCH_2$]$_3$ (I), wherein each $Z^1$ and $Z^2$ independently represent a hydrogen atom, a $C_1$-$C_4$ alkyl group or a bond to a silicon atom of another monomer and at least one other trivalent metal oxide monomer.

Other embodiments, including particular aspects of the embodiments summarized above, will be evident from the detailed description that follows.

DETAILED DESCRIPTION OF THE INVENTION

Figure 1:
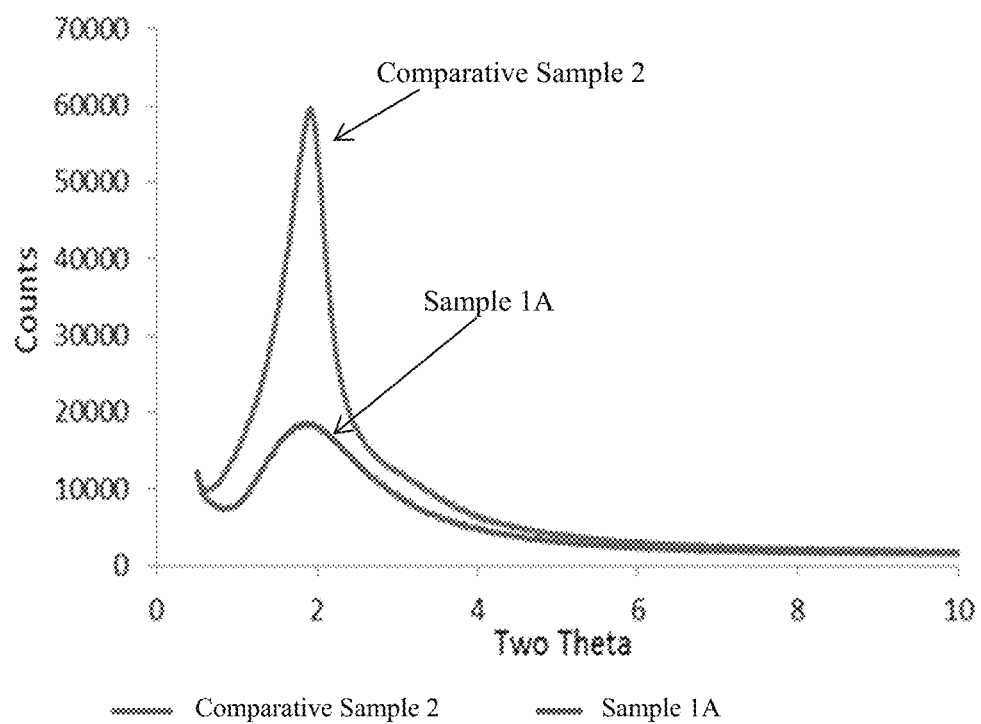
FIG. 1 illustrates an X-Ray Diffraction (XRD) spectrum for Sample 1A and Comparative Sample 2.

In various aspects of the invention, organosilica materials, methods for preparing organosilica materials and gas and liquid separation processes using the organosilica materials are provided.

I. Definitions

For purposes of this invention and the claims hereto, the numbering scheme for the Periodic Table Groups is according to the IUPAC Periodic Table of Elements.

The term "and/or" as used in a phrase such as "A and/or B" herein is intended to include "A and B", "A or B", "A", and "B".

The terms "substituent", "radical", "group", and "moiety" may be used interchangeably.

As used herein, and unless otherwise specified, the term "$C_n$" means hydrocarbon(s) having n carbon atom(s) per molecule, wherein n is a positive integer.

As used herein, and unless otherwise specified, the term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

As used herein, and unless otherwise specified, the term "alkyl" refers to a saturated hydrocarbon radical having from 1 to 12 carbon atoms (i.e. $C_1$-$C_{12}$ alkyl), particularly from 1 to 8 carbon atoms (i.e. $C_1$-$C_8$ alkyl), particularly from 1 to 6 carbon atoms (i.e. $C_1$-$C_6$ alkyl), and particularly from 1 to 4 carbon atoms (i.e. $C_1$-$C_4$ alkyl). Examples of alkyl groups include, but are not limited to, methyl, ethyl, propyl, butyl, pentyl, hexyl, heptyl, octyl, decyl, and so forth. The alkyl group may be linear, branched or cyclic. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl and so forth. As used herein, "$C_1$ alkyl" refers to methyl (—$CH_3$), "$C_2$ alkyl" refers to ethyl (—$CH_2CH_3$), "$C_3$ alkyl" refers to propyl (—$CH_2CH_2CH_3$) and "$C_4$ alkyl" refers to butyl (e.g. —$CH_2CH_2CH_2CH_3$, —$(CH_3)CHCH_2CH_3$, —$CH_2CH(CH_3)_2$, etc.). Further, as used herein, "Me" refers to methyl, and "Et" refers to ethyl, "i-Pr" refers to isopropyl, "t-Bu" refers to tert-butyl, and "Np" refers to neopentyl.

As used herein, and unless otherwise specified, the term "alkylene" refers to a divalent alkyl moiety containing 1 to 12 carbon atoms (i.e. $C_1$-$C_{12}$ alkylene) in length and meaning the alkylene moiety is attached to the rest of the molecule at both ends of the alkyl unit. For example, alkylenes include, but are not limited to, —$CH_2$—, —$CH_2CH_2$—, —$CH(CH_3)CH_2$—, —$CH_2CH_2CH_2$—, etc. The alkylene group may be linear or branched.

As used herein, and unless otherwise specified, the term "nitrogen-containing alkyl" refers to an alkyl group as defined herein wherein one or more carbon atoms in the alkyl group is substituted with a nitrogen atom or a nitrogen-containing cyclic hydrocarbon having from 2 to 10 carbon atoms (i.e., a nitrogen-containing cyclic $C_2$-$C_{10}$ hydrocarbon), particularly having from 2 to 5 carbon atoms (i.e., a nitrogen-containing cyclic $C_2$-$C_5$ hydrocarbon), and particularly having from 2 to 5 carbon atoms (i.e., a nitrogen-containing cyclic $C_2$-$C_5$ hydrocarbon). The nitrogen-containing cyclic hydrocarbon may have one or more nitrogen atoms. The nitrogen atom(s) may optionally be substituted with one or two $C_1$-$C_6$ alkyl groups. The nitrogen-containing alkyl can have from 1 to 12 carbon atoms (i.e. $C_1$-$C_{12}$ nitrogen-containing alkyl), particularly from 1 to 10 carbon atoms (i.e. $C_1$-$C_{10}$ nitrogen-containing alkyl), particularly from 2 to 10 carbon atoms (i.e. $C_2$-$C_{10}$ nitrogen-containing alkyl), particularly from 3 to 10 carbon atoms (i.e. $C_3$-$C_{10}$ nitrogen-containing alkyl), and particularly from 3 to 8 carbon atoms (i.e. $C_1$-$C_{10}$ nitrogen-containing alkyl). Examples of nitrogen-containing alkyls include, but are not limited to,

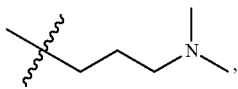

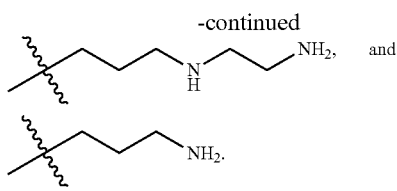

As used herein, and unless otherwise specified, the term "nitrogen-containing alkylene" refers to an alkylene group as defined herein wherein one or more carbon atoms in the alkyl group is substituted with a nitrogen atom. The nitrogen atom(s) may optionally be substituted with one or two $C_1$-$C_6$ alkyl groups. The nitrogen-containing alkylene can have from 1 to 12 carbon atoms (i.e. $C_1$-$C_{12}$ nitrogen-containing alkylene), particularly from 2 to 10 carbon atoms (i.e. $C_2$-$C_{10}$ nitrogen-containing alkylene), particularly from 3 to 10 carbon atoms (i.e. $C_3$-$C_{10}$ nitrogen-containing alkylene), particularly from 4 to 10 carbon atoms (i.e. $C_4$-$C_{10}$ nitrogen-containing alkylene), and particularly from 3 to 8 carbon atoms (i.e. $C_3$-$C_8$ nitrogen-containing alkyl). Examples of nitrogen-containing alkylenes include, but are not limited to,

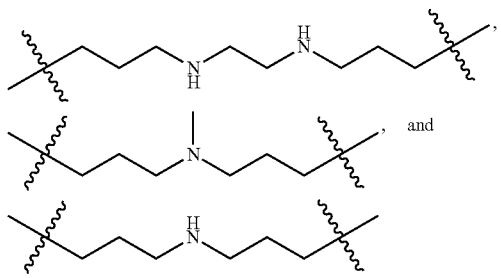

As used herein, and unless otherwise specified, the term "alkenyl" refers to an unsaturated hydrocarbon radical having from 2 to 12 carbon atoms (i.e., $C_2$-$C_{12}$ alkenyl), particularly from 2 to 8 carbon atoms (i.e., $C_2$-$C_8$ alkenyl), particularly from 2 to 6 carbon atoms (i.e., $C_2$-$C_6$ alkenyl), and having one or more (e.g., 2, 3, etc.) carbon-carbon double bonds. The alkenyl group may be linear, branched or cyclic. Examples of alkenyls include, but are not limited to ethenyl (vinyl), 2-propenyl, 3-propenyl, 1,4-pentadienyl, 1,4-butadienyl, 1-butenyl, 2-butenyl and 3-butenyl. "Alkenyl" is intended to embrace all structural isomeric forms of an alkenyl. For example, butenyl encompasses 1,4-butadienyl, 1-butenyl, 2-butenyl and 3-butenyl, etc.

As used herein, and unless otherwise specified, the term "alkenylene" refers to a divalent alkenyl moiety containing 2 to about 12 carbon atoms (i.e. $C_2$-$C_{12}$ alkenylene) in length and meaning that the alkylene moiety is attached to the rest of the molecule at both ends of the alkyl unit. For example, alkenylenes include, but are not limited to, —CH=CH—, —CH=CHCH$_2$—, —CH=CH=CH—, —CH$_2$CH$_2$CH=CHCH$_2$—, etc. —CH$_2$CH$_2$—, —CH(CH$_3$)CH$_2$—, —CH$_2$CH$_2$CH$_2$—, etc. The alkenylene group may be linear or branched.

As used herein, and unless otherwise specified, the term "alkynyl" refers to an unsaturated hydrocarbon radical having from 2 to 12 carbon atoms (i.e., $C_2$-$C_{12}$ alkynyl), particularly from 2 to 8 carbon atoms (i.e., $C_2$-$C_8$ alkynyl), particularly from 2 to 6 carbon atoms (i.e., $C_2$-$C_6$ alkynyl), and having one or more (e.g., 2, 3, etc.) carbon-carbon triple bonds. The alkynyl group may be linear, branched or cyclic. Examples of alkynyls include, but are not limited to ethynyl, 1-propynyl, 2-butynyl, and 1,3-butadiynyl. "Alkynyl" is intended to embrace all structural isomeric forms of an alkynyl. For example, butynyl encompasses 2-butynyl, and 1,3-butadiynyl and propynyl encompasses 1-propynyl and 2-propynyl (propargyl).

As used herein, and unless otherwise specified, the term "alkynylene" refers to a divalent alkynyl moiety containing 2 to about 12 carbon atoms (i.e. $C_2$-$C_{12}$ alkenylene) in length and meaning that the alkylene moiety is attached to the rest of the molecule at both ends of the alkyl unit. For example, alkenylenes include, but are not limited to, —C≡C—, —C≡CCH$_2$—, —C≡CCH$_2$C≡C—, —CH$_2$CH$_2$C≡CCH$_2$—, etc. —CH$_2$CH$_2$—, —CH(CH$_3$)CH$_2$—, —CH$_2$CH$_2$CH$_2$—, etc. The alkynlene group may be linear or branched.

As used herein, and unless otherwise specified, the term "alkoxy" refers to —O-alkyl containing from 1 to about 10 carbon atoms. The alkoxy may be straight-chain or branched-chain. Non-limiting examples include methoxy, ethoxy, propoxy, butoxy, isobutoxy, tert-butoxy, pentoxy, and hexoxy. "$C_1$ alkoxy" refers to methoxy, "$C_2$ alkoxy" refers to ethoxy, "$C_3$ alkoxy" refers to propoxy and "$C_4$ alkoxy" refers to butoxy. Further, as used herein, "OMe" refers to methoxy and "OEt" refers to ethoxy.

As used herein, and unless otherwise specified, the term "aromatic" refers to unsaturated cyclic hydrocarbons having a delocalized conjugated π system and having from 5 to 20 carbon atoms (aromatic $C_5$-$C_{20}$ hydrocarbon), particularly from 5 to 12 carbon atoms (aromatic $C_5$-$C_{12}$ hydrocarbon), and particularly from 5 to 10 carbon atoms (aromatic $C_5$-$C_{12}$ hydrocarbon). Exemplary aromatics include, but are not limited to benzene, toluene, xylenes, mesitylene, ethylbenzene, cumene, naphthalene, methylnaphthalene, dimethylnaphthalenes, ethylnaphthalenes, acenaphthalene, anthracene, phenanthrene, tetraphene, naphthacene, benzanthracenes, fluoranthrene, pyrene, chrysene, triphenylene, and the like, and combinations thereof. Additionally, the aromatic may comprise one or more heteroatoms. Examples of heteroatoms include, but are not limited to, nitrogen, oxygen, and/or sulfur. Aromatics with one or more heteroatom include, but are not limited to furan, benzofuran, thiophene, benzothiophene, oxazole, thiazole and the like, and combinations thereof. The aromatic may comprise monocyclic, bicyclic, tricyclic, and/or polycyclic rings (in some embodiments, at least monocyclic rings, only monocyclic and bicyclic rings, or only monocyclic rings) and may be fused rings.

As used herein, and unless otherwise specified, the term "aryl" refers to any monocyclic or polycyclic cyclized carbon radical containing 6 to 14 carbon ring atoms, wherein at least one ring is an aromatic hydrocarbon. Examples of aryls include, but are not limited to phenyl, naphthyl, pyridinyl, and indolyl.

As used herein, and unless otherwise specified, the term "aralkyl" refers to an alkyl group substituted with an aryl group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of aralkyl groups include, but are not limited to phenymethyl, phenylethyl, and naphthylmethyl. The aralkyl may comprise one or more heteroatoms and be referred to as a "heteroaralkyl." Examples of heteroatoms include, but are not limited to, nitrogen (i.e., nitrogen-containing heteroaralkyl), oxygen (i.e., oxygen-containing heteroaralkyl), and/or sulfur (i.e., sulfur-containing heteroaralkyl). Examples of heteroaralkyl groups include, but are not limited to, pyridinylethyl, indolylmethyl, furylethyl, and quinolinylpropyl.

As used herein, and unless otherwise specified, the term "heterocyclo" refers to fully saturated, partially saturated or unsaturated or polycyclic cyclized carbon radical containing from 4 to 20 carbon ring atoms and containing one or more heteroatoms atoms. Examples of heteroatoms include, but are not limited to, nitrogen (i.e., nitrogen-containing heterocyclo), oxygen (i.e., oxygen-containing heterocyclo), and/or sulfur (i.e., sulfur-containing heterocyclo). Examples of heterocyclo groups include, but are not limited to, thienyl, furyl, pyrrolyl, piperazinyl, pyridyl, benzoxazolyl, quinolinyl, imidazolyl, pyrrolidinyl, and piperidinyl.

As used herein, and unless otherwise specified, the term "heterocycloalkyl" refers to an alkyl group substituted with heterocyclo group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of heterocycloalkyl groups include, but are not limited to thienylmethyl, furylethyl, pyrrolylmethyl, piperazinylethyl, pyridylmethyl, benzoxazolylethyl, quinolinylpropyl, and imidazolylpropyl.

As used herein, the term "hydroxyl" refers to an —OH group.

As used herein, the term "mesoporous" refers to solid materials having pores that have a diameter within the range of from about 2 nm to about 50 nm.

As used herein, the term "organosilica" refers to an organosiloxane compound that comprises one or more organic groups bound to two or more Si atoms.

As used herein, the term "silanol" refers to a Si—OH group.

As used herein, the term "silanol content" refers to the percent of the Si—OH groups in a compound and can be calculated by standard methods, such as NMR.

As used herein, the terms "structure directing agent," "SDA," and/or "porogen" refer to one or more compounds added to the synthesis media to aid in and/or guide the polymerization and/or polycondensing and/or organization of the building blocks that form the organosilica material framework. Further, a "porogen" is understood to be a compound capable of forming voids or pores in the resultant organosilica material framework. As used herein, the term "structure directing agent" encompasses and is synonymous and interchangeable with the terms "templating agent" and "template."

As used herein, and unless otherwise specified, the term "adsorption" includes physisorption, chemisorption, and condensation onto a solid material and combinations thereof.

II. Organosilica Materials

The invention relates to organosilica materials. In a first embodiment, the organosilica material may be a polymer of at least one independent monomer of Formula $[Z^1OZ^2OSiCH_2]_3$ (I), wherein each $Z^1$ and $Z^2$ independently can be a hydrogen atom, a $C_1$-$C_4$ alkyl group or a bond to a silicon atom of another monomer and at least one other independent trivalent metal oxide monomer.

As used herein, and unless otherwise specified, "a bond to a silicon atom of another monomer" means the bond can advantageously displace a moiety (particularly an oxygen-containing moiety such as a hydroxyl, an alkoxy or the like), if present, on a silicon atom of the another monomer so there may be a bond directly to the silicon atom of the another monomer thereby connecting the two monomers, e.g., via a Si—O—Si linkage. For clarity, in this bonding scenario, the "another monomer" can be a monomer of the same type or a monomer of a different type.

II.A. Monomers of Formula (I)

In various embodiments, each $Z^1$ and/or $Z^2$ can be a hydrogen atom.

Additionally or alternatively, each $Z^1$ and/or $Z^2$ can be a $C_1$-$C_4$ alkyl group, a $C_1$-$C_3$ alkyl group, a $C_1$-$C_2$ alkyl group or methyl.

Additionally or alternatively, each $Z^1$ and/or $Z^2$ can be a bond to a silicon atom of another monomer.

Additionally or alternatively, each $Z^1$ and $Z^2$ independently can be a hydrogen atom, a $C_1$-$C_2$ alkyl group or a bond to a silicon atom of another monomer.

Additionally or alternatively, each $Z^1$ and $Z^2$ independently can be a hydrogen atom, ethyl or a bond to a silicon atom of another monomer.

Additionally or alternatively, each $Z^1$ and $Z^2$ independently can be a hydrogen atom or a bond to a silicon atom of another monomer.

II.B. Trivalent Metal Oxide Monomer

In various embodiments, the at least one other trivalent metal oxide monomer may be an independent unit of Formula $M^1(OZ^3)_3$ (II), wherein $M^1$ can be a Group 13 metal and each $Z^3$ independently can be a hydrogen atom, a $C_1$-$C_6$ alkyl or a bond to a silicon atom of another monomer.

Additionally or alternatively, $M^1$ can be B, Al, Ga, In, Tl, or Uut. In particular, $M^1$ can be Al or B.

Additionally or alternatively, each $Z^3$ can be a hydrogen atom.

Additionally or alternatively, $M^1$ can be Al or B and each $Z^3$ can be a hydrogen atom.

Additionally or alternatively, each $Z^3$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, each $Z^3$ can be methyl, ethyl, propyl or butyl.

Additionally or alternatively, $M^1$ can be Al or B and each $Z^3$ can be a hydrogen atom, methyl, ethyl, propyl or butyl.

Additionally or alternatively, each $Z^3$ can be a bond to a silicon atom of another monomer.

Additionally or alternatively, $M^1$ can be Al or B and each $Z^3$ can be a hydrogen atom, methyl, ethyl, propyl, butyl or a bond to a silicon atom of another monomer.

Additionally or alternatively, $M^1$ can be Al or B and each $Z^3$ can be a hydrogen atom or a bond to a silicon atom of another monomer.

Additionally or alternatively, $M^1$ can be Al and each $Z^3$ can be a hydrogen atom, methyl, ethyl, propyl, butyl or a bond to a silicon atom of another monomer.

In a particular embodiment, $M^1$ can be Al and each $Z^3$ can be a hydrogen atom, methyl or a bond to a silicon atom of another monomer.

In another particular embodiment, $M^1$ can be Al and each $Z^3$ can be a hydrogen atom, ethyl or a bond to a silicon atom of another monomer.

In another particular embodiment, $M^1$ can be Al and each $Z^3$ can be a hydrogen atom, propyl or a bond to a silicon atom of another monomer.

In another particular embodiment, $M^1$ can be Al and each $Z^3$ can be a hydrogen atom, butyl or a bond to a silicon atom of another monomer.

Additionally or alternatively, when present with Formula (I), each $Z^1$ and $Z^2$ independently can be can be a hydrogen atom, a $C_1$-$C_2$ alkyl group or a bond to a silicon atom of another monomer; $M^1$ can be Al or B; and each $Z^3$ can be a hydrogen atom, methyl, ethyl, propyl, butyl or a bond to a silicon atom of another monomer.

In another particular embodiment, when present with Formula (I), each $Z^1$ and $Z^2$ independently can be can be a hydrogen atom, ethyl or a bond to a silicon atom of another monomer; $M^1$ can be Al or B; and each $Z^3$ can be a hydrogen atom, methyl, ethyl, propyl, butyl or a bond to a silicon atom of another monomer.

In another particular embodiment, when present with Formula (I), each $Z^1$ and $Z^2$ independently can be can be a hydrogen atom, or a bond to a silicon atom of another monomer; $M^1$ can be Al or B; and each $Z^3$ can be a hydrogen atom or a bond to a silicon atom of another monomer.

In various embodiments, the at least one other trivalent metal oxide monomer may be an independent unit of Formula $(Z^4O)_2M^2$-O—Si$(OZ^5)_3$ (III), wherein $M^2$ can be a Group 13 metal and each $Z^4$ and each $Z^5$ independently can be a hydrogen atom, a $C_1$-$C_6$ alkyl group or a bond to a silicon atom of another monomer.

Additionally or alternatively, $M^2$ can be B, Al, Ga, In, Tl, or Uut. In particular, $M^2$ can be Al or B.

Additionally or alternatively, each $Z^4$ and/or each $Z^5$ can be a hydrogen atom.

Additionally or alternatively, $M^2$ can be Al or B and each $Z^4$ and/or each $Z^5$ can be a hydrogen atom.

Additionally or alternatively, each $Z^4$ and/or each $Z^5$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, each $Z^4$ and/or each $Z^5$ can be methyl, ethyl, propyl or butyl.

Additionally or alternatively, $M^2$ can be Al or B; and each $Z^4$ and each $Z^5$ independently can be a hydrogen atom, methyl, ethyl, propyl or butyl.

Additionally or alternatively, each $Z^4$ and/or each $Z^5$ can be a bond to a silicon atom of another monomer.

Additionally or alternatively, $M^2$ can be Al or B; and each $Z^4$ and each $Z^5$ independently can be a hydrogen atom, methyl, ethyl, propyl, butyl or a bond to a silicon atom of another monomer.

Additionally or alternatively, $M^2$ can be Al or B; and each $Z^4$ and each $Z^5$ independently can be a hydrogen atom or a bond to a silicon atom of another monomer.

Additionally or alternatively, $M^2$ can be Al; and each $Z^4$ and each $Z^5$ independently can be a hydrogen atom, methyl, ethyl, propyl, butyl or a bond to a silicon atom of another monomer.

In a particular embodiment, $M^2$ can be Al; and each $Z^4$ and each $Z^5$ independently can be a hydrogen atom, methyl or a bond to a silicon atom of another monomer.

In another particular embodiment, $M^2$ can be Al; and each $Z^4$ and each $Z^5$ independently can be a hydrogen atom, ethyl or a bond to a silicon atom of another monomer.

In another particular embodiment, $M^2$ can be Al; and each $Z^4$ and each $Z^5$ independently can be a hydrogen atom, propyl or a bond to a silicon atom of another monomer.

In another particular embodiment, $M^2$ can be Al; and each $Z^4$ and each $Z^5$ independently can be a hydrogen atom, butyl or a bond to a silicon atom of another monomer.

Additionally or alternatively, when present with Formula (I), each $Z^1$ and $Z^2$ independently can be can be a hydrogen atom, a $C_1$-$C_2$ alkyl group or a bond to a silicon atom of another monomer; $M^2$ can be Al or B; and each $Z^4$ and each $Z^5$ independently can be a hydrogen atom, methyl, ethyl, propyl, butyl or a bond to a silicon atom of another monomer.

Additionally or alternatively, when present with Formula (I), each $Z^1$ and $Z^2$ independently can be can be a hydrogen atom, ethyl or a bond to a silicon atom of another monomer; $M^2$ can be Al or B; and each $Z^4$ and each $Z^5$ independently can be a hydrogen atom, methyl, ethyl, propyl, butyl or a bond to a silicon atom of another monomer.

Additionally or alternatively, when present with Formula (I), each $Z^1$ and $Z^2$ independently can be can be a hydrogen atom or a bond to a silicon atom of another monomer; $M^2$ can be Al or B; and each $Z^4$ and each $Z^5$ independently can be a hydrogen atom or a bond to a silicon atom of another monomer.

II.C. Additional Optional Monomers

1. Formula (IV)

In various embodiments, the organosilica material may further comprise a monomer having at least one independent unit of Formula $[Z^6OZ^7SiCH_2]_3$ (IV), wherein each $Z^6$ can be a hydrogen atom, a $C_1$-$C_4$ alkyl group or a bond to a silicon atom of another monomer and each $Z^7$ can be a hydroxyl group, a $C_1$-$C_6$ alkyl group or an oxygen atom bonded to a silicon atom of another monomer.

As used herein, and unless otherwise specified, "an oxygen atom bonded to a silicon atom of another monomer" means that the oxygen atom can advantageously displace a moiety (particularly an oxygen-containing moiety such as a hydroxyl), if present, on a silicon atom of the another monomer so the oxygen atom may be bonded directly to the silicon atom of the another monomer thereby connecting the two monomers, e.g., via a Si—O—Si linkage. For clarity, in this bonding scenarios, the "another monomer" can be a monomer of the same type or a monomer of a different type.

In various embodiments, each $Z^6$ can be a hydrogen atom.

Additionally or alternatively, each $Z^6$ can be a $C_1$-$C_4$ alkyl group, a $C_1$-$C_3$ alkyl group, a $C_1$-$C_2$ alkyl group or methyl.

Additionally or alternatively, each $Z^6$ can be a hydrogen atom or a $C_1$-$C_2$ alkyl group.

Additionally or alternatively, each $Z^6$ can be a bond to a silicon atom of another monomer.

Additionally or alternatively, each $Z^6$ can be a hydrogen atom, a $C_1$-$C_2$ alkyl group or a bond to a silicon atom of another monomer.

Additionally or alternatively, each $Z^6$ can be a hydrogen atom, ethyl or a bond to a silicon atom of another monomer.

Additionally or alternatively, each $Z^7$ can be a hydroxyl group.

Additionally or alternatively, each $Z^7$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl.

Additionally or alternatively, each $Z^7$ can be a hydroxyl group or a $C_1$-$C_4$ alkyl group.

Additionally or alternatively, each $Z^7$ can be an oxygen atom bonded to a silicon atom of another monomer.

Additionally or alternatively, each $Z^7$ can be a hydroxyl group, a $C_1$-$C_4$ alkyl group or an oxygen atom bonded to a silicon atom of another monomer.

Additionally or alternatively, each $Z^7$ can be a hydroxyl group, methyl or an oxygen atom bonded to a silicon atom of another monomer.

Additionally or alternatively, each $Z^6$ can be a hydrogen atom, a $C_1$-$C_2$ alkyl group or a bond to a silicon atom of another monomer and each $Z^7$ can be a hydroxyl group, a $C_1$-$C_4$ alkyl group or an oxygen atom bonded to a silicon atom of another monomer.

Additionally or alternatively, each $Z^6$ can be a hydrogen atom, ethyl or a bond to a silicon atom of another monomer and each $Z^7$ can be a hydroxyl group, methyl or an oxygen atom bonded to a silicon atom of another monomer.

Additionally or alternatively, each $Z^6$ can be a hydrogen atom or a bond to a silicon atom of another monomer and each $Z^7$ can be a hydroxyl group, methyl or an oxygen atom bonded to a silicon atom of another monomer.

2. Formula (V)

In various embodiments, the organosilica material may further comprise a monomer having at least one independent unit of Formula $Z^8OZ^9Z^{10}Z^{11}Si$ (V), wherein each $Z^8$ can be a hydrogen atom or a $C_1$-$C_4$ alkyl group or a bond to a silicon atom of another monomer; and $Z^9$, $Z^{10}$ and $Z^{11}$ each independently can be selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroaralkyl group, and a nitrogen-containing optionally substituted heterocycloalkyl group, and an oxygen atom bonded to a silicon atom of another monomer.

In various aspects, each $Z^8$ can be a hydrogen atom.

Additionally or alternatively, each $Z^8$ can be a $C_1$-$C_4$ alkyl group, a $C_1$-$C_3$ alkyl group, a $C_1$-$C_2$ alkyl group or methyl.

Additionally or alternatively, each $Z^8$ can be a hydrogen atom or a $C_1$-$C_2$ alkyl group.

Additionally or alternatively, each $Z^8$ can be a bond to a silicon atom of another monomer.

Additionally or alternatively, each $Z^8$ can be a hydrogen atom, a $C_1$-$C_2$ alkyl group or a bond to a silicon atom of another monomer.

Additionally or alternatively, each $Z^8$ can be a hydrogen atom, ethyl, methyl or a bond to a silicon atom of another monomer.

Additionally or alternatively, $Z^9$, $Z^{10}$ and $Z^{11}$ each independently can be a hydroxyl group.

Additionally or alternatively, each $Z^8$ can be a hydrogen atom, a $C_1$-$C_2$ alkyl group or a bond to a silicon atom of another monomer; and $Z^9$, $Z^{10}$ and $Z^{11}$ each independently can be a hydroxyl group.

Additionally or alternatively, $Z^9$, $Z^{10}$ and $Z^{11}$ each independently can be a $C_1$-$C_4$ alkyl group, a $C_1$-$C_3$ alkyl group, a $C_1$-$C_2$ alkyl group or methyl.

Additionally or alternatively, $Z^9$, $Z^{10}$ and $Z^{11}$ each independently can be a hydroxyl group or a $C_1$-$C_2$ alkyl group.

Additionally or alternatively, each $Z^8$ can be a hydrogen atom, a $C_1$-$C_2$ alkyl group or a bond to a silicon atom of another monomer; and $Z^9$, $Z^{10}$ and $Z^{11}$ each independently can be a hydroxyl group or a $C_1$-$C_2$ alkyl group.

Additionally or alternatively, $Z^9$, $Z^{10}$ and $Z^{11}$ each independently can be a $C_1$-$C_4$ alkoxy group, a $C_1$-$C_3$ alkoxy group, a $C_1$-$C_2$ alkoxy group or methoxy.

Additionally or alternatively, $Z^9$, $Z^{10}$ and $Z^{11}$ each independently can be selected from the group consisting of a hydroxyl group, a $C_1$-$C_2$ alkyl group and a $C_1$-$C_2$ alkoxy group.

Additionally or alternatively, each $Z^8$ can be a hydrogen atom, a $C_1$-$C_2$ alkyl group or a bond to a silicon atom of another monomer; and $Z^9$, $Z^{10}$ and $Z^{11}$ each can be selected from the group consisting of a hydroxyl group, a $C_1$-$C_2$ alkyl group and a $C_1$-$C_2$ alkoxy group.

Additionally or alternatively, $Z^9$, $Z^{10}$ and $Z^{11}$ each independently can be a nitrogen-containing $C_1$-$C_{10}$ alkyl group, a nitrogen-containing $C_1$-$C_9$ alkyl group, a nitrogen-containing $C_1$-$C_8$ alkyl group, a nitrogen-containing $C_1$-$C_7$ alkyl group, a nitrogen-containing $C_1$-$C_6$ alkyl group, a nitrogen-containing $C_1$-$C_5$ alkyl group, a nitrogen-containing $C_1$-$C_4$ alkyl group, a nitrogen-containing $C_1$-$C_3$ alkyl group, a nitrogen-containing $C_1$-$C_2$ alkyl group, or a methylamine. In particular, $Z^9$, $Z^{10}$ and $Z^{11}$ each independently can be a nitrogen-containing $C_2$-$C_{10}$ alkyl group, a nitrogen-containing $C_3$-$C_{10}$ alkyl group, a nitrogen-containing $C_3$-$C_9$ alkyl group, or a nitrogen-containing $C_3$-$C_8$ alkyl group. The aforementioned nitrogen-containing alkyl groups may have one or more nitrogen atoms (e.g., 2, 3, etc.). Examples of nitrogen-containing $C_1$-$C_{10}$ alkyl groups include, but are not limited to,

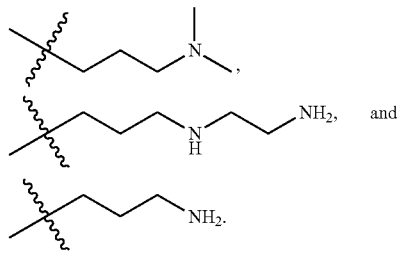

Additionally or alternatively, $Z^9$, $Z^{10}$ and $Z^{11}$ each independently can be selected from the group consisting of a hydroxyl group, a $C_1$-$C_2$ alkyl group, a $C_1$-$C_2$ alkoxy group and a nitrogen-containing $C_3$-$C_{10}$ alkyl group.

Additionally or alternatively, each $Z^8$ can be a hydrogen atom, a $C_1$-$C_2$ alkyl group or a bond to a silicon atom of another monomer; and $Z^9$, $Z^{10}$ and $Z^{11}$ each independently can be selected from the group consisting of a hydroxyl group, a $C_1$-$C_2$ alkyl group, a $C_1$-$C_2$ alkoxy group and a nitrogen-containing $C_3$-$C_{10}$ alkyl group.

Additionally or alternatively, $Z^9$, $Z^{10}$ and $Z^{11}$ each independently can be a nitrogen-containing heteroaralkyl group. The nitrogen-containing heteroaralkyl group can be a nitrogen-containing $C_4$-$C_{12}$ heteroaralkyl group, a nitrogen-containing $C_4$-$C_{10}$ heteroaralkyl group, or a nitrogen-containing $C_4$-$C_8$ heteroaralkyl group. Examples of nitrogen-containing heteroaralkyl groups include but are not limited to pyridinylethyl, pyridinylpropyl, pyridinylmethyl, indolylmethyl, pyrazinylethyl, and pyrazinylpropyl. The aforementioned nitrogen-containing heteroaralkyl groups may have one or more nitrogen atoms (e.g., 2, 3, etc.).

Additionally or alternatively, $Z^9$, $Z^{10}$ and $Z^{11}$ each independently can be selected from the group consisting of a hydroxyl group, a $C_1$-$C_2$ alkyl group, a $C_1$-$C_2$ alkoxy group, nitrogen-containing $C_3$-$C_{10}$ alkyl group and a nitrogen-containing heteroaralkyl group.

Additionally or alternatively, each $Z^8$ can be a hydrogen atom, a $C_1$-$C_2$ alkyl group or a bond to a silicon atom of another monomer; and $Z^9$, $Z^{10}$ and $Z^{11}$ each independently can be selected from the group consisting of a hydroxyl group, a $C_1$-$C_2$ alkyl group, a $C_1$-$C_2$ alkoxy group, a nitrogen-containing $C_3$-$C_{10}$ alkyl group and a nitrogen-containing heteroaralkyl group.

Additionally or alternatively, $Z^9$, $Z^{10}$ and $Z^{11}$ each independently can be a nitrogen-containing heterocycloalkyl group, wherein the heterocycloalkyl group may be optionally substituted with a $C_1$-$C_6$ alkyl group, particularly a $C_1$-$C_4$ alkyl group. The nitrogen-containing heterocycloalkyl group can be a nitrogen-containing $C_4$-$C_{12}$ heterocycloalkyl group, a nitrogen-containing $C_4$-$C_{10}$ heterocycloalkyl group, or a nitrogen-containing $C_4$-$C_8$ heterocycloalkyl group. Examples of nitrogen-containing heterocycloalkyl groups include but are not limited to piperazinylethyl, piperazinylpropyl, piperidinylethyl, piperidinylpropyl. The aforementioned nitrogen-containing heterocycloalkyl groups may have one or more nitrogen atoms (e.g., 2, 3, etc.).

Additionally or alternatively, $Z^9$, $Z^{10}$ and $Z^{11}$ each independently can be selected from the group consisting of a hydroxyl group, a $C_1$-$C_2$ alkyl group, a $C_1$-$C_2$ alkoxy group, nitrogen-containing $C_3$-$C_{10}$ alkyl group, a nitrogen-containing heteroaralkyl group, and a nitrogen-containing optionally substituted heterocycloalkyl group.

Additionally or alternatively, each $Z^8$ can be a hydrogen atom, a $C_1$-$C_2$ alkyl group or a bond to a silicon atom of another monomer; and $Z^9$, $Z^{10}$ and $Z^{11}$ each independently can be selected from the group consisting of a hydroxyl group, a $C_1$-$C_2$ alkyl group, a $C_1$-$C_2$ alkoxy group, a nitrogen-containing $C_3$-$C_{10}$ alkyl group, a nitrogen-containing heteroaralkyl group and a nitrogen-containing optionally substituted heterocycloalkyl group.

Additionally or alternatively, $Z^9$, $Z^{10}$ and $Z^{11}$ each independently can be an oxygen atom bonded to a silicon atom of another monomer.

Additionally or alternatively, each $Z^8$ can be a hydrogen atom, a $C_1$-$C_2$ alkyl group or a bond to a silicon atom of another monomer; and $Z^9$, $Z^{10}$ and $Z^{11}$ each independently can be selected from the group consisting of a hydroxyl group, a $C_1$-$C_2$ alkyl group, a $C_1$-$C_2$ alkoxy group, a nitrogen-containing $C_3$-$C_{10}$ alkyl group, a nitrogen-containing heteroaralkyl group, a nitrogen-containing optionally substituted heterocycloalkyl group and an oxygen atom bonded to a silicon atom of another monomer.

Additionally or alternatively, each $Z^8$ can be a hydrogen atom, a $C_1$-$C_2$ alkyl group or a bond to a silicon atom of another monomer; and $Z^9$, $Z^{10}$ and $Z^{11}$ each independently can be selected from the group consisting of a hydroxyl group, a $C_1$-$C_2$ alkyl group, a $C_1$-$C_2$ alkoxy group, a nitrogen-containing $C_3$-$C_5$ alkyl group, $C_4$-$C_{10}$ heteroaralkyl group, a nitrogen-containing optionally substituted $C_4$-$C_{10}$ heterocycloalkyl group, and an oxygen atom bonded to a silicon atom of another monomer.

Additionally or alternatively, each $Z^8$ can be a hydrogen atom or a bond to a silicon atom of another monomer; and $Z^9$, $Z^{10}$ and $Z^{11}$ each independently can be selected from the group consisting of a hydroxyl group, a $C_1$-$C_2$ alkyl group, a nitrogen-containing $C_3$-$C_8$ alkyl group, $C_4$-$C_{10}$ heteroaralkyl group, a nitrogen-containing optionally substituted $C_4$-$C_{10}$ heterocycloalkyl group, and an oxygen atom bonded to a silicon atom of another monomer.

In a particular embodiment, each $Z^8$ can be a hydrogen atom, ethyl or a bond to a silicon atom of another monomer; and $Z^9$, $Z^{10}$ and $Z^{11}$ each independently can be selected from the group consisting of a hydroxyl group, ethoxy, and an oxygen atom bonded to a silicon atom of another monomer.

In another particular embodiment, each $Z^8$ can be a hydrogen atom, ethyl or a bond to a silicon atom of another comonomer; $Z^9$ and $Z^{10}$ each independently can be selected from the group consisting of a hydroxyl group, ethoxy, and an oxygen atom bonded to a silicon atom of another monomer; and $Z^{11}$ can be methyl.

In another particular embodiment, each $Z^8$ can be a hydrogen atom, methyl or a bond to a silicon atom of another comonomer; $Z^9$ and $Z^{10}$ each independently can be selected from the group consisting of a hydroxyl group, methoxy, and an oxygen atom bonded to a silicon atom of another monomer; and $Z^{11}$ each can be

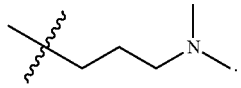 [SMILES: *CCCN(C)C]

In another particular embodiment, each $Z^8$ can be a hydrogen atom, ethyl or a bond to a silicon atom of another comonomer; $Z^9$ and $Z^{10}$ each independently can be selected from the group consisting of a hydroxyl group, ethoxy, and an oxygen atom bonded to a silicon atom of another monomer; and each $Z^{11}$ can be

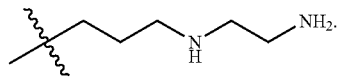 [SMILES: *CCCNCCN]

In another particular embodiment, each $Z^8$ can be a hydrogen atom, ethyl or a bond to a silicon atom of another comonomer; $Z^9$ and $Z^{10}$ each independently can be selected from the group consisting of a hydroxyl group, ethoxy, and an oxygen atom bonded to a silicon atom of another monomer; and each $Z^{11}$ can be

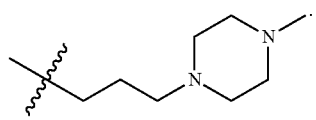 [SMILES: *CCCN1CCN(C)CC1]

In another particular embodiment, each $Z^8$ can be a hydrogen atom, ethyl or a bond to a silicon atom of another comonomer; $Z^9$ and $Z^{10}$ each independently can be selected from the group consisting of a hydroxyl group, ethoxy, and an oxygen atom bonded to a silicon atom of another monomer; and each $Z^{11}$ can be

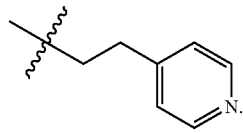 [SMILES: *CCc1ccncc1]

In another particular embodiment, $Z^8$ can be a hydrogen atom, ethyl or a bond to a silicon atom of another comonomer; $Z^9$ and $Z^{10}$ each independently can be selected from the group consisting of a hydroxyl group, ethoxy, and an oxygen atom bonded to a silicon atom of another monomer; and $Z^{11}$ can be

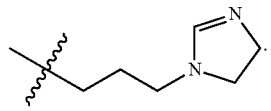 [SMILES: *CCCN1C=NCC1]

In another particular embodiment, each $Z^8$ can be a hydrogen atom, ethyl or a bond to a silicon atom of another comonomer; $Z^9$ and $Z^{10}$ each independently can be selected from the group consisting of a hydroxyl group, ethoxy, and an oxygen atom bonded to a silicon atom of another monomer; and each $Z^{11}$ can be

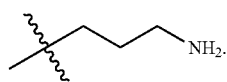

3. Formula (VI)

In various embodiments, the organosilica material may further comprise a monomer having at least one unit of Formula $Z^{12}Z^{13}Z^{14}Si-R-SiZ^{12}Z^{13}Z^{14}$ (VI), wherein each $Z^{12}$ independently can be a hydroxyl group, a $C_1$-$C_4$ alkoxy group or an oxygen atom bonded to a silicon atom of another comonomer; each $Z^{13}$ and $Z^{14}$ independently can be a hydroxyl group, a $C_1$-$C_4$ alkoxy group, a $C_1$-$C_4$ alkyl group or an oxygen atom bonded to a silicon atom of another monomer; and each R is selected from the group consisting a $C_1$-$C_8$ alkylene group, a $C_2$-$C_8$ alkenylene group, a $C_2$-$C_8$ alkynylene group, a nitrogen-containing $C_2$-$C_{10}$ alkylene group, an optionally substituted $C_6$-$C_{20}$ aralkyl and an optionally substituted $C_4$-$C_{20}$ heterocycloalkyl group.

In various aspects, each $Z^{12}$ can be a hydroxyl group.

Additionally or alternatively, each $Z^{12}$ can be a $C_1$-$C_4$ alkoxy group, a $C_1$-$C_3$ alkoxy group, a $C_1$-$C_2$ alkoxy group or methoxy.

Additionally or alternatively, each $Z^{12}$ can be a hydroxyl group or a $C_1$-$C_2$ alkoxy group.

Additionally or alternatively, each $Z^{12}$ can be an oxygen atom bonded to a silicon atom of another comonomer.

Additionally or alternatively, each $Z^{12}$ can be a hydroxyl group, a $C_1$-$C_2$ alkoxy group or an oxygen atom bonded to a silicon atom of another comonomer.

Additionally or alternatively, each $Z^{12}$ can be a hydroxyl group or an oxygen atom bonded to a silicon atom of another comonomer.

Additionally or alternatively, each $Z^{13}$ and $Z^{14}$ independently can be a hydroxyl group.

Additionally or alternatively, each $Z^{13}$ and $Z^{14}$ independently can be a $C_1$-$C_4$ alkoxy group, a $C_1$-$C_3$ alkoxy group, a $C_1$-$C_2$ alkoxy group or methoxy.

Additionally or alternatively, each $Z^{13}$ and $Z^{14}$ independently can be a hydroxyl group or a $C_1$-$C_2$ alkoxy group.

Additionally or alternatively, each $Z^{13}$ and $Z^{14}$ independently can be a $C_1$-$C_4$ alkyl group, a $C_1$-$C_3$ alkyl group, a $C_1$-$C_2$ alkyl group or methyl.

Additionally or alternatively, each $Z^{13}$ and $Z^{14}$ independently can be a hydroxyl group, a $C_1$-$C_2$ alkoxy group, or a $C_1$-$C_2$ alkyl group.

Additionally or alternatively, each $Z^{13}$ and $Z^{14}$ independently can be an oxygen atom bonded to a silicon atom of another comonomer.

Additionally or alternatively, each $Z^{13}$ and $Z^{14}$ independently can be a hydroxyl group, a $C_1$-$C_2$ alkoxy group, a $C_1$-$C_2$ alkyl group, or an oxygen atom bonded to a silicon atom of another comonomer.

Additionally or alternatively, each $Z^{13}$ and $Z^{14}$ independently can be a hydroxyl group, a $C_1$-$C_2$ alkyl group, or an oxygen atom bonded to a silicon atom of another comonomer.

Additionally or alternatively, each $Z^{12}$ can be a hydroxyl group, a $C_1$-$C_2$ alkoxy group or an oxygen atom bonded to a silicon atom of another comonomer; and each $Z^{13}$ and $Z^{14}$ independently can be a hydroxyl group, a $C_1$-$C_2$ alkoxy group, a $C_1$-$C_2$ alkyl group, or an oxygen atom bonded to a silicon atom of another comonomer.

Additionally or alternatively, each $Z^{12}$ can be a hydroxyl group, ethoxy, methoxy or an oxygen atom bonded to a silicon atom of another comonomer; and each $Z^{13}$ and $Z^{14}$ independently can be a hydroxyl group, ethoxy, methyl, or an oxygen atom bonded to a silicon atom of another comonomer.

Additionally or alternatively, each $Z^{12}$ can be a hydroxyl group or an oxygen atom bonded to a silicon atom of another comonomer; and each $Z^{13}$ and $Z^{14}$ independently can be a hydroxyl group, methyl, or an oxygen atom bonded to a silicon atom of another comonomer.

Additionally or alternatively, each R can be a $C_1$-$C_8$ alkylene group, a $C_1$-$C_7$ alkylene group, a $C_1$-$C_6$ alkylene group, a $C_1$-$C_5$ alkylene group, a $C_1$-$C_4$ alkylene group, a $C_1$-$C_3$ alkylene group, a $C_1$-$C_2$ alkylene group or —$CH_2$—.

Additionally or alternatively, each $Z^{12}$ can be a hydroxyl group, a $C_1$-$C_2$ alkoxy group or an oxygen atom bonded to a silicon atom of another comonomer; each $Z^{13}$ and $Z^{14}$ independently can be a hydroxyl group, a $C_1$-$C_2$ alkoxy group, a $C_1$-$C_2$ alkyl group, or an oxygen atom bonded to a silicon atom of another comonomer; and each R can be a $C_1$-$C_4$ alkylene group.

Additionally or alternatively, each R can be a $C_2$-$C_8$ alkenylene group, a $C_2$-$C_7$ alkenylene group, a $C_2$-$C_6$ alkenylene group, a $C_2$-$C_5$ alkenylene group, a $C_2$-$C_4$ alkenylene group, a $C_2$-$C_3$ alkenylene group, or —HC=CH—.

Additionally or alternatively, each $Z^{12}$ can be a hydroxyl group, a $C_1$-$C_2$ alkoxy group or an oxygen atom bonded to a silicon atom of another comonomer; each $Z^{13}$ and $Z^{14}$ independently can be a hydroxyl group, a $C_1$-$C_2$ alkoxy group, a $C_1$-$C_2$ alkyl group, or an oxygen atom bonded to a silicon atom of another comonomer; and each R can be selected from the group consisting of a $C_1$-$C_4$ alkylene group and a $C_2$-$C_4$ alkenylene group.

Additionally or alternatively, each R can be a $C_2$-$C_8$ alkynylene group, a $C_2$-$C_7$ alkynylene group, a $C_2$-$C_6$ alkynylene group, a $C_2$-$C_5$ alkynylene group, a $C_2$-$C_4$ alkynylene group, a $C_2$-$C_3$ alkynylene group, or —C≡C—

Additionally or alternatively, each $Z^{12}$ can be a hydroxyl group, a $C_1$-$C_2$ alkoxy group or an oxygen atom bonded to a silicon atom of another comonomer; each $Z^{13}$ and $Z^{14}$ independently can be a hydroxyl group, a $C_1$-$C_2$ alkoxy group, a $C_1$-$C_2$ alkyl group, or an oxygen atom bonded to a silicon atom of another comonomer; and each R can be selected from the group consisting of a $C_1$-$C_4$ alkylene group, a $C_2$-$C_4$ alkenylene group and a $C_2$-$C_4$ alkynylene group.

Additionally or alternatively, each R can be a nitrogen-containing $C_2$-$C_{10}$ alkylene group, a nitrogen-containing $C_3$-$C_{10}$ alkylene group, a nitrogen-containing $C_4$-$C_{10}$ alkylene group, a nitrogen-containing $C_4$-$C_9$ alkylene group, a nitrogen-containing $C_4$-$C_8$ alkylene group, or nitrogen containing $C_3$-$C_8$ alkylene group. The aforementioned nitrogen-containing alkylene groups may have one or more nitrogen atoms (e.g., 2, 3, etc.). Examples of nitrogen-containing alkylene groups include, but are not limited to,

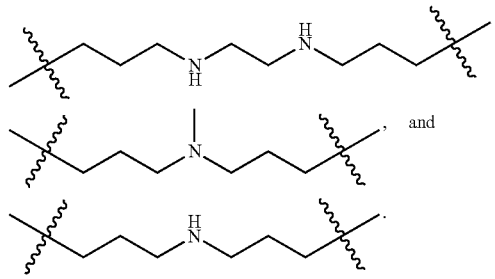

Additionally or alternatively, each $Z^{12}$ can be a hydroxyl group, a $C_1$-$C_2$ alkoxy group or an oxygen atom bonded to a silicon atom of another comonomer; each $Z^{13}$ and $Z^{14}$ independently can be a hydroxyl group, a $C_1$-$C_2$ alkoxy group, a $C_1$-$C_2$ alkyl group, or an oxygen atom bonded to a silicon atom of another comonomer; and each R can be selected from the group consisting of a $C_1$-$C_4$ alkylene group, a $C_2$-$C_4$ alkenylene group, a $C_2$-$C_4$ alkynylene group and a nitrogen-containing $C_4$-$C_{10}$ alkylene group.

Additionally or alternatively, each R can be an optionally substituted $C_6$-$C_{20}$ aralkyl, an optionally substituted $C_6$-$C_{14}$ aralkyl, or an optionally substituted $C_6$-$C_{10}$ aralkyl. Examples of $C_6$-$C_{20}$ aralkyls include, but are not limited to, phenylmethyl, phenylethyl, and naphthylmethyl. The aralkyl may be optionally substituted with a $C_1$-$C_6$ alkyl group, particularly a $C_1$-$C_4$ alkyl group.

Additionally or alternatively, each $Z^{12}$ can be a hydroxyl group, a $C_1$-$C_2$ alkoxy group or an oxygen atom bonded to a silicon atom of another comonomer; each $Z^{13}$ and $Z^{14}$ independently can be a hydroxyl group, a $C_1$-$C_2$ alkoxy group, a $C_1$-$C_2$ alkyl group, or an oxygen atom bonded to a silicon atom of another comonomer; and R can be selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group and an optionally substituted $C_6$-$C_{10}$ aralkyl.

Additionally or alternatively, each R can be an optionally substituted $C_4$-$C_{20}$ heterocycloalkyl group, an optionally substituted $C_4$-$C_{16}$ heterocycloalkyl group, an optionally substituted $C_4$-$C_{12}$ heterocycloalkyl group, or an optionally substituted $C_4$-$C_{10}$ heterocycloalkyl group. Examples of $C_4$-$C_{20}$ heterocycloalkyl groups include, but are not limited to, thienylmethyl, furylethyl, pyrrolylmethyl, piperazinylethyl, pyridylmethyl, benzoxazolylethyl, quinolinylpropyl, and imidazolylpropyl. The heterocycloalkyl may be optionally substituted with a $C_1$-$C_6$ alkyl group, particularly a $C_1$-$C_4$ alkyl group.

Additionally or alternatively, each $Z^{12}$ can be a hydroxyl group, a $C_1$-$C_2$ alkoxy group or an oxygen atom bonded to a silicon atom of another comonomer; each $Z^{13}$ and $Z^{14}$ independently can be a hydroxyl group, a $C_1$-$C_2$ alkoxy group, a $C_1$-$C_2$ alkyl group, or an oxygen atom bonded to a silicon atom of another comonomer; and R can be selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl and an optionally substituted $C_4$-$C_{10}$ heterocycloalkyl group.

Additionally or alternatively, each $Z^{12}$ can be a hydroxyl group, ethoxy, methoxy or an oxygen atom bonded to a silicon atom of another comonomer; each $Z^{13}$ and $Z^{14}$ independently can be a hydroxyl group, ethoxy, methoxy, methyl, or an oxygen atom bonded to a silicon atom of another comonomer; and R can be selected from the group consisting of —CH$_2$—, —CH$_2$CH$_2$—, —HC=CH—,

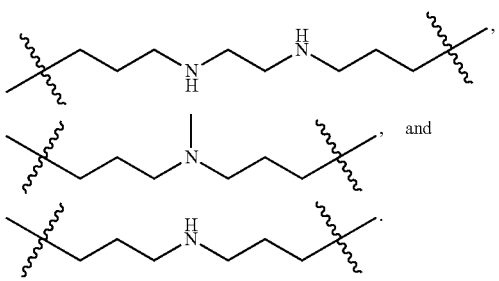

Additionally or alternatively, each $Z^{12}$ can be a hydroxyl group or an oxygen atom bonded to a silicon atom of another comonomer; each $Z^{13}$ and $Z^{14}$ independently can be a hydroxyl group, methyl, or an oxygen atom bonded to a silicon atom of another comonomer; and each R can be selected from the group consisting of —CH$_2$—, —CH$_2$CH$_2$—, —HC=CH—,

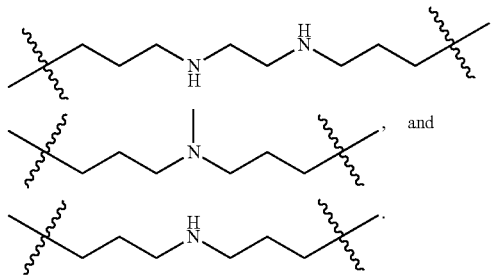

In a particular embodiment, each $Z^{12}$ can be a hydroxyl group, ethoxy or an oxygen atom bonded to a silicon atom of another comonomer; each $Z^{13}$ can be a hydroxyl group, ethoxy, and an oxygen atom bonded to a silicon atom of another monomer; each $Z^{14}$ can be methyl; and each R can be —CH$_2$CH$_2$—.

In another particular embodiment, each $Z^{12}$ can be a hydroxyl group, ethoxy or an oxygen atom bonded to a silicon atom of another comonomer; each $Z^{13}$ and $Z^{14}$ independently can be selected from the group consisting of a hydroxyl group, ethoxy, and an oxygen atom bonded to a silicon atom of another monomer; and R can be —CH$_2$—.

In another particular embodiment, each $Z^{12}$ can be a hydroxyl group, ethoxy or an oxygen atom bonded to a silicon atom of another comonomer; each $Z^{13}$ and $Z^{14}$ independently can be selected from the group consisting of a hydroxyl group, ethoxy, and an oxygen atom bonded to a silicon atom of another monomer; and R can be —HC=CH—.

In another particular embodiment, each $Z^{12}$ can be a hydroxyl group, methoxy or an oxygen atom bonded to a silicon atom of another comonomer; each $Z^{13}$ and $Z^{14}$ independently can be selected from the group consisting of a hydroxyl group, methoxy, and an oxygen atom bonded to a silicon atom of another monomer; and each R can be

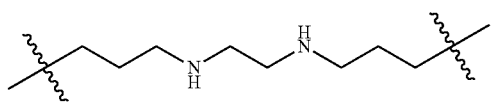

In another particular embodiment, each $Z^{12}$ can be a hydroxyl group, ethoxy or an oxygen atom bonded to a silicon atom of another comonomer; each $Z^{13}$ can be a hydroxyl group, ethoxy, and an oxygen atom bonded to a silicon atom of another monomer; each $Z^{14}$ can be methyl; and each R can be

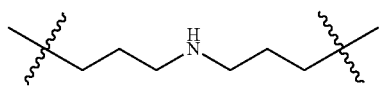

In another particular embodiment, each $Z^{12}$ can be a hydroxyl group, methoxy or an oxygen atom bonded to a silicon atom of another comonomer; each $Z^{13}$ can be a hydroxyl group, methoxy, and an oxygen atom bonded to a silicon atom of another monomer; each $Z^{14}$ can be methyl; and each R can be

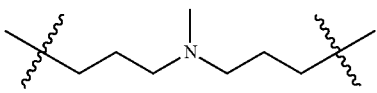

The organosilica materials made by the methods described herein can be characterized as described in the following sections.

II.A. X-Ray Diffraction Peaks

The organosilica materials described herein can exhibit powder X-ray diffraction patterns with one peak between about 1 and about 4 degrees 2θ, particularly one peak between about 1 and about 3 degrees 2θ or between about 1 and about 2 degrees 2θ. Additionally or alternatively, the organosilica materials can exhibit substantially no peaks in the range of about 0.5 to about 10 degrees 2θ, about 0.5 to about 12 degrees 2θ range, about 0.5 to about 15 degrees 2θ, about 0.5 to about 20 degrees 2θ, about 0.5 to about 30 degrees 2θ, about 0.5 to about 40 degrees 2θ, about 0.5 to about 50 degrees 2θ, about 0.5 to about 60 degrees 2θ, about 0.5 to about 70 degrees 2θ, about 2 to about 10 degrees 2θ, about 2 to about 12 degrees 2θ range, about 2 to about 15 degrees 2θ, about 2 to about 20 degrees 2θ, about 2 to about 30 degrees 2θ, about 2 to about 40 degrees 2θ, about 2 to about 50 degrees 2θ, about 2 to about 60 degrees 2θ, about 2 to about 70 degrees 2θ, about 3 to about 10 degrees 2θ, about 3 to about 12 degrees 2θ range, about 3 to about 15 degrees 2θ, about 3 to about 20 degrees 2θ, about 3 to about 30 degrees 2θ, about 3 to about 40 degrees 2θ, about 3 to about 50 degrees 2θ, about 3 to about 60 degrees 2θ, or about 3 to about 70 degrees 2θ.

II.B. Silanol Content

The organosilica materials can have a silanol content that varies within wide limits, depending on the composition of the synthesis solution. The silanol content can conveniently be determined by solid state silicon NMR.

In various aspects, the organosilica material can have a silanol content of greater than about 5%, greater than about 10%, greater than about 15%, greater than about 20%, greater than about 25%, greater than about 30%, greater than about 33%, greater than 35%, greater than about 40%, greater than about 41%, greater than about 44%, greater than about 45%, greater than about 50%, greater than about 55%, greater than about 60%, greater than about 65%, greater than about 70%, greater than about 75%, or about 80%. In certain embodiments, the silanol content can be greater than about 30% or greater than about 41%.

Additionally or alternatively, the organosilica material may have a silanol content of about 5% to about 80%, about 5% to about 75%, about 5% to about 70%, about 5% to about 65%, about 5% to about 60%, about 5% to about 55%, about 5% to about 50%, about 5% to about 45%, about 5% to about 44%, about 5% to to about 41%, about 5% to about 40%, about 5% to about 35%, about 5% to about 33%, about 5% to about 30%, about 5% to about 25%, about 5% to about 20%, about 5% to about 15%, about 5% to about 10%, about 10% to about 80%, about 10% to about 75%, about 10% to about 70%, about 10% to about 65%, about 10% to about 60%, about 10% to about 55%, about 10% to about 50%, about 10% to about 45%, about 10% to about 44%, about 10% to about 41%, about 10% to about 40%, about 10% to about 35%, about 10% to about 33%, about 10% to about 30%, about 10% to about 25%, about 10% to about 20%, about 20% to about 80%, about 20% to about 75%, about 20% to about 70%, about 20% to about 65%, about 20% to about 60%, about 20% to about 55%, about 20% to about 50%, about 20% to about 45%, about 20% to about 44%, about 20% to about 41%, about 20% to about 40%, about 20% to about 35%, about 20% to about 33%, about 20% to about 30%, about 20% to about 25%, about 30% to about 80%, about 30% to about 75%, about 30% to about 70%, about 30% to about 65%, about 30% to about 60%, about 30% to about 55%, about 30% to about 50%, about 30% to about 45%, about 30% to about 44%, about 30% to about 41%, about 30% to about 40%, about 30% to about 35%, about 30% to about 33%, about 40% to about 80%, about 40% to about 75%, about 40% to about 70%, about 40% to about 65%, about 40% to about 60%, about 40% to about 55%, about 40% to about 50%, about 40% to about 45%, about 40% to about 44%, or about 40% to about 41%.

II.C. Pore Size

The organosilica material described herein are advantageously in a mesoporous form. As indicated previously, the term mesoporous refers to solid materials having pores with a diameter within the range of from about 2 nm to about 50 nm. The average pore diameter of the organosilica material can be determined, for example, using nitrogen adsorption-desorption isotherm techniques within the expertise of one of skill in the art, such as the BET (Brunauer Emmet Teller) method.

The organosilica material can have an average pore diameter of about 0.2 nm, about 0.4 nm, about 0.5 nm, about 0.6 nm, about 0.8 nm, about 1.0 nm, about 1.5 nm, about 1.8 nm or less than about 2.0 nm.

Additionally or alternatively, the organosilica material can advantageously have an average pore diameter within the mesopore range of about 2.0 nm, about 2.5 nm, about 3.0 nm, about 3.1 nm, about 3.2 nm, about 3.3 nm, about 3.4 nm, about 3.5 nm, about 3.6 nm, about 3.7 nm, about 3.8 nm, about 3.9 nm about 4.0 nm, about 4.1 nm, about 4.5 nm, about 5.0 nm, about 6.0 nm, about 7.0 nm, about 7.3 nm, about 8 nm, about 8.4 nm, about 9 nm, about 10 nm, about 11 nm, about 13 nm, about 15 nm, about 18 nm, about 20 nm, about 23 nm, about 25 nm, about 30 nm, about 40 nm, about 45 nm, or about 50 nm.

Additionally or alternatively, the organosilica material can have an average pore diameter of 0.2 nm to about 50 nm, about 0.2 nm to about 40 nm, about 0.2 nm to about 30 nm, about 0.2 nm to about 25 nm, about 0.2 nm to about 23 nm, about 0.2 nm to about 20 nm, about 0.2 nm to about 18 nm, about 0.2 nm to about 15 nm, about 0.2 nm to about 13 nm, about 0.2 nm to about 11 nm, about 0.2 nm to about 10 nm, about 0.2 nm to about 9 nm, about 0.2 nm to about 8.4 nm, about 0.2 nm to about 8 nm, about 0.2 nm to about 7.3 nm, about 0.2 nm to about 7.0 nm, about 0.2 nm to about 6.0 nm, about 0.2 nm to about 5.0 nm, about 0.2 nm to about 4.5 nm, about 0.2 nm to about 4.1 nm, about 0.2 nm to about 4.0 nm, about 0.2 nm to about 3.9 nm, about 0.2 nm to about 3.8 nm, about 0.2 nm to about 3.7 nm, about 0.2 nm to about 3.6 nm, about 0.2 nm to about 3.5 nm, about 0.2 nm to about 3.4 nm, about 0.2 nm to about 3.3 nm, about 0.2 nm to about 3.2 nm, about 0.2 nm to about 3.1 nm, about 0.2 nm to about 3.0 nm, about 0.2 nm to about 2.5 nm, about 0.2 nm to about 2.0 nm, about 0.2 nm to about 1.0 nm, about 1.0 nm to about 50 nm, about 1.0 nm to about 40 nm, about 1.0 nm to about 30 nm, about 1.0 nm to about 25 nm, about 1.0 nm to about 23 nm, about 1.0 nm to about 20 nm, about 1.0 nm to about 18 nm, about 1.0 nm to about 15 nm, about 1.0 nm to about 13 nm, about 1.0 nm to about 11 nm, about 1.0 nm to about 10 nm, about 1.0 nm to about 9 nm, about 1.0 nm to about 8.4 nm, about 1.0 nm to about 8 nm, about 1.0 nm to about 7.3 nm, about 1.0 nm to about 7.0 nm, about 1.0 nm to about 6.0 nm, about 1.0 nm to about 5.0 nm, about 1.0 nm to about 4.5 nm, about 1.0 nm to about 4.1 nm, about 1.0 nm to about 4.0 nm, about 1.0 nm to about 3.9 nm, about 1.0 nm to about 3.8 nm, about 1.0 nm to about 3.7 nm, about 1.0 nm to about 3.6 nm, about 1.0 nm to about 3.5 nm, about 1.0 nm to about 3.4 nm, about 1.0 nm to about 3.3 nm, about 1.0 nm to about 3.2 nm, about 1.0 nm to about 3.1 nm, about 1.0 nm to about 3.0 nm or about 1.0 nm to about 2.5 nm.

In particular, the organosilica material can advantageously have an average pore diameter in the mesopore range of about 2.0 nm to about 50 nm, about 2.0 nm to about 40 nm, about 2.0 nm to about 30 nm, about 2.0 nm to about 25 nm, about 2.0 nm to about 23 nm, about 2.0 nm to about 20 nm, about 2.0 nm to about 18 nm, about 2.0 nm to about 15 nm, about 2.0 nm to about 13 nm, about 2.0 nm to about 11 nm, about 2.0 nm to about 10 nm, about 2.0 nm to about 9 nm, about 2.0 nm to about 8.4 nm, about 2.0 nm to about 8 nm, about 2.0 nm to about 7.3 nm, about 2.0 nm to about 7.0 nm, about 2.0 nm to about 6.0 nm, about 2.0 nm to about 5.0 nm, about 2.0 nm to about 4.5 nm, about 2.0 nm to about 4.1 nm, about 2.0 nm to about 4.0 nm, about 2.0 nm to about 3.9 nm, about 2.0 nm to about 3.8 nm, about 2.0 nm to about 3.7 nm, about 2.0 nm to about 3.6 nm, about 2.0 nm to about 3.5 nm, about 2.0 nm to about 3.4 nm, about 2.0 nm to about 3.3 nm, about 2.0 nm to about 3.2 nm, about 2.0 nm to about 3.1 nm, about 2.0 nm to about 3.0 nm, about 2.0 nm to about 2.5 nm, about 2.5 nm to about 50 nm, about 2.5 nm to about 40 nm, about 2.5 nm to about 30 nm, about 2.5 nm to about 25 nm, about 2.5 nm to about 23 nm, about 2.5 nm to about 20 nm, about 2.5 nm to about 18 nm, about 2.5 nm to about 15 nm, about 2.5 nm to about 13 nm, about 2.5 nm to about 11 nm, about 2.5 nm to about 10 nm, about 2.5 nm to about 9 nm, about 2.5 nm to about 8.4 nm, about 2.5 nm to about 8 nm, about 2.5 nm to about 7.3 nm, about 2.5 nm to about 7.0 nm, about 2.5 nm to about 6.0 nm, about 2.5 nm to about 5.0 nm, about 2.5 nm to about 4.5 nm, about 2.5 nm to about 4.1 nm, about 2.5 nm to about 4.0 nm, about 2.5 nm to about 3.9 nm, about 2.5 nm to about 3.8 nm, about 2.5 nm to about 3.7 nm, about 2.5 nm to about 3.6 nm, about 2.5 nm to about 3.5 nm, about 2.5 nm to about 3.4 nm, about 2.5 nm to about 3.3 nm, about 2.5 nm to about 3.2 nm, about 2.5 nm to about 3.1 nm, about 2.5 nm to about 3.0 nm, about 3.0 nm to about 50 nm, about 3.0 nm to about 40 nm, about 3.0 nm to about 30 nm, about 3.0 nm to about 25 nm, about 3.0 nm to about 23 nm, about 3.0 nm to about 20 nm, about 3.0 nm to about 18 nm, about 3.0 nm to about 15 nm, about 3.0 nm to about 13 nm, about 3.0 nm to about 11 nm, about 3.0 nm to about 10 nm, about 3.0 nm to about 9 nm, about 3.0 nm to about 8.4 nm, about 3.0 nm to about 8 nm, about 3.0 nm to about 7.3 nm, about 3.0 nm to about 7.0 nm, about 3.0 nm to about 6.0 nm, about 3.0 nm to about 5.0 nm, about 3.0 nm to about 4.5 nm, about 3.0 nm to about 4.1 nm, or about 3.0 nm to about 4.0 nm.

In one particular embodiment, the organosilica material described herein can have an average pore diameter of about 1.0 nm to about 30.0 nm, particularly about 1.0 nm to about 25.0 nm, particularly about 1.5 nm to about 25.0 nm, particularly about 2.0 nm to about 25.0 nm, particularly about 2.0 nm to about 20.0 nm, particularly about 2.0 nm to about 15.0 nm, or particularly about 2.0 nm to about 10.0 nm.

Using surfactant as a template to synthesize mesoporous materials can create highly ordered structure, e.g. well-defined cylindrical-like pore channels. In some circumstances, there may be no hysteresis loop observed from $N_2$ adsorption isotherm. In other circumstances, for instance where mesoporous materials can have less ordered pore structures, a hysteresis loop may be observed from N2 adsorption isotherm experiments. In such circumstances, without being bound by theory, the hysteresis can result from the lack of regularity in the pore shapes/sizes and/or from bottleneck constrictions in such irregular pores.

II.D. Surface Area

The surface area of the organosilica material can be determined, for example, using nitrogen adsorption-desorption isotherm techniques within the expertise of one of skill in the art, such as the BET (Brunauer Emmet Teller) method. This method may determine a total surface area, an external surface area, and a microporous surface area. As used herein, and unless otherwise specified, "total surface area" refers to the total surface area as determined by the BET method. As used herein, and unless otherwise specified, "microporous surface area" refers to microporous surface are as determined by the BET method.

In various embodiments, the organosilica material can have a total surface area greater than or equal to about 100 $m^2/g$, greater than or equal to about 200 $m^2/g$, greater than or equal to about 300 $m^2/g$, greater than or equal to about 400 $m^2/g$, greater than or equal to about 450 $m^2/g$, greater than or equal to about 500 $m^2/g$, greater than or equal to about 550 $m^2/g$, greater than or equal to about 600 $m^2/g$, greater than or equal to about 700 $m^2/g$, greater than or equal to about 800 $m^2/g$, greater than or equal to about 850 $m^2/g$, greater than or equal to about 900 $m^2/g$, greater than or equal to about 1,000 $m^2/g$, greater than or equal to about 1,050 $m^2/g$, greater than or equal to about 1,100 $m^2/g$, greater than or equal to about 1,150 $m^2/g$, greater than or equal to about 1,200 $m^2/g$, greater than or equal to about 1,250 $m^2/g$, greater than or equal to about 1,300 $m^2/g$, greater than or equal to about 1,400 $m^2/g$, greater than or equal to about 1,450 $m^2/g$, greater than or equal to about 1,500 $m^2/g$, greater than or equal to about 1,550 $m^2/g$, greater than or equal to about 1,600 $m^2/g$, greater than or equal to about 1,700 $m^2/g$, greater than or equal to about 1,800 $m^2/g$, greater than or equal to about 1,900 $m^2/g$, greater than or equal to about 2,000 $m^2/g$, greater than or equal to greater than or equal to about 2,100 $m^2/g$, greater than or equal to about 2,200 $m^2/g$, greater than or equal to about 2,300 $m^2/g$ or about 2,500 $m^2/g$.

Additionally or alternatively, the organosilica material may have a total surface area of about 50 $m^2/g$ to about 2,500 $m^2/g$, about 50 $m^2/g$ to about 2,000 $m^2/g$, about 50 $m^2/g$ to about 1,500 $m^2/g$, about 50 $m^2/g$ to about 1,000 $m^2/g$, about 100 $m^2/g$ to about 2,500 $m^2/g$, about 100 $m^2/g$ to about 2,300 $m^2/g$, about 100 $m^2/g$ to about 2,200 $m^2/g$, about 100 $m^2/g$ to about 2,100 $m^2/g$, about 100 $m^2/g$ to about 2,000 $m^2/g$, about 100 $m^2/g$ to about 1,900 $m^2/g$, about 100 $m^2/g$ to about 1,800 $m^2/g$, about 100 $m^2/g$ to about 1,700 $m^2/g$, about 100 $m^2/g$ to about 1,600 $m^2/g$, about 100 $m^2/g$ to about 1,550 $m^2/g$, about 100 $m^2/g$ to about 1,500 $m^2/g$, about 100 $m^2/g$ to about 1,450 $m^2/g$, about 100 $m^2/g$ to about 1,400 $m^2/g$, about 100 $m^2/g$ to about 1,300 $m^2/g$, about 100 $m^2/g$ to about 1,250 $m^2/g$, about 100 $m^2/g$ to about 1,200 $m^2/g$, about 100 $m^2/g$ to about 1,150 $m^2/g$, about 100 $m^2/g$ to about 1,100 $m^2/g$, about 100 $m^2/g$ to about 1,050 $m^2/g$, about 100 $m^2/g$ to about 1,000 $m^2/g$, about 100 $m^2/g$ to about 900 $m^2/g$, about 100 $m^2/g$ to about 850 $m^2/g$, about 100 $m^2/g$ to about 800 $m^2/g$, about 100 $m^2/g$ to about 700 $m^2/g$, about 100 $m^2/g$ to about 600 $m^2/g$, about 100 $m^2/g$ to about 550 $m^2/g$, about 100 $m^2/g$ to about 500 $m^2/g$, about 100 $m^2/g$ to about 450 $m^2/g$, about 100 $m^2/g$ to about 400 $m^2/g$, about 100 $m^2/g$ to about 300 $m^2/g$, about 100 $m^2/g$ to about 200 $m^2/g$, about 200 $m^2/g$ to about 2,500 $m^2/g$, about 200 $m^2/g$ to about 2,300 $m^2/g$, about 200 $m^2/g$ to about 2,200 $m^2/g$, about 200 $m^2/g$ to about 2,100 $m^2/g$, about 200 $m^2/g$ to about 2,000 m²/g, about 200 m²/g to about 1,900 m²/g, about 200 m²/g to about 1,800 m²/g, about 200 m²/g to about 1,700 m²/g, about 200 m²/g to about 1,600 m²/g, about 200 m²/g to about 1,550 m²/g, about 200 m²/g to about 1,500 m²/g, about 200 m²/g to about 1,450 m²/g, about 200 m²/g to about 1,400 m²/g, about 200 m²/g to about 1,300 m²/g, about 200 m²/g to about 1,250 m²/g, about 200 m²/g to about 1,200 m²/g, about 200 m²/g to about 1,150 m²/g, about 200 m²/g to about 1,100 m²/g, about 200 m²/g to about 1,050 m²/g, about 200 m²/g to about 1,000 m²/g, about 200 m²/g to about 900 m²/g, about 200 m²/g to about 850 m²/g, about 200 m²/g to about 800 m²/g, about 200 m²/g to about 700 m²/g, about 200 m²/g to about 600 m²/g, about 200 m²/g to about 550 m²/g, about 200 m²/g to about 500 m²/g, about 200 m²/g to about 450 m²/g, about 200 m²/g to about 400 m²/g, about 200 m²/g to about 300 m²/g, about 500 m²/g to about 2,500 m²/g, about 500 m²/g to about 2,300 m²/g, about 500 m²/g to about 2,200 m²/g, about 500 m²/g to about 2,100 m²/g, about 500 m²/g to about 2,000 m²/g, about 500 m²/g to about 1,900 m²/g, about 500 m²/g to about 1,800 m²/g, about 500 m²/g to about 1,700 m²/g, about 500 m²/g to about 1,600 m²/g, about 500 m²/g to about 1,550 m²/g, about 500 m²/g to about 1,500 m²/g, about 500 m²/g to about 1,450 m²/g, about 500 m²/g to about 1,400 m²/g, about 500 m²/g to about 1,300 m²/g, about 500 m²/g to about 1,250 m²/g, about 500 m²/g to about 1,200 m²/g, about 500 m²/g to about 1,150 m²/g, about 500 m²/g to about 1,100 m²/g, about 500 m²/g to about 1,050 m²/g, about 500 m²/g to about 1,000 m²/g, about 500 m²/g to about 900 m²/g, about 500 m²/g to about 850 m²/g, about 500 m²/g to about 800 m²/g, about 500 m²/g to about 700 m²/g, about 500 m²/g to about 600 m²/g, about 500 m²/g to about 550 m²/g, about 1,000 m²/g to about 2,500 m²/g, about 1,000 m²/g to about 2,300 m²/g, about 1,000 m²/g to about 2,200 m²/g, about 1,000 m²/g to about 2,100 m²/g, about 1,000 m²/g to about 2,000 m²/g, about 1,000 m²/g to about 1,900 m²/g, about 1,000 m²/g to about 1,800 m²/g, about 1,000 m²/g to about 1,700 m²/g, about 1,000 m²/g to about 1,600 m²/g, about 1,000 m²/g to about 1,550 m²/g, about 1,000 m²/g to about 1,500 m²/g, about 1,000 m²/g to about 1,450 m²/g, about 1,000 m²/g to about 1,400 m²/g, about 1,000 m²/g to about 1,300 m²/g, about 1,000 m²/g to about 1,250 m²/g, about 1,000 m²/g to about 1,200 m²/g, about 1,000 m²/g to about 1,150 m²/g, about 1,000 m²/g to about 1,100 m²/g, or about 1,000 m²/g to about 1,050 m²/g.

In one particular embodiment, the organosilica material described herein may have a total surface area of about 200 m²/g to about 2,500 m²g, particularly about 400 m²/g to about 2,500 m²g, particularly about 400 m²/g to about 2,000 m²/g, or particularly about 400 m²/g to about 1,500 m²/g.

III.E. Pore Volume

The pore volume of the organosilica material made by the methods described herein can be determined, for example, using nitrogen adsorption-desorption isotherm techniques within the expertise of one of skill in the art, such as the BET (Brunauer Emmet Teller) method.

In various embodiments, the organosilica material can have a pore volume greater than or equal to about 0.1 cm³/g, greater than or equal to about 0.2 cm³/g, greater than or equal to about 0.3 cm³/g, greater than or equal to about 0.4 cm³/g, greater than or equal to about 0.5 cm³/g, greater than or equal to about 0.6 cm³/g, greater than or equal to about 0.7 cm³/g, greater than or equal to about 0.8 cm³/g, greater than or equal to about 0.9 cm³/g, greater than or equal to about 1.0 cm³/g, greater than or equal to about 1.1 cm³/g, greater than or equal to about 1.2 cm³/g, greater than or equal to about 1.3 cm³/g, greater than or equal to about 1.4 cm³/g, greater than or equal to about 1.5 cm³/g, greater than or equal to about 1.6 cm³/g, greater than or equal to about 1.7 cm³/g, greater than or equal to about 1.8 cm³/g, greater than or equal to about 1.9 cm³/g, greater than or equal to about 2.0 cm³/g, greater than or equal to about 2.5 cm³/g, greater than or equal to about 3.0 cm³/g, greater than or equal to about 3.5 cm³/g, greater than or equal to about 4.0 cm³/g, greater than or equal to about 5.0 cm³/g, greater than or equal to about 6.0 cm³/g, greater than or equal to about 7.0 cm³/g, or about 10.0 cm³/g.

Additionally or alternatively, the organosilica material can have a pore volume of about 0.1 cm³/g to about 10.0 cm³/g, about 0.1 cm³/g to about 7.0 cm³/g, about 0.1 cm³/g to about 6.0 cm³/g, about 0.1 cm³/g to about 5.0 cm³/g, about 0.1 cm³/g to about 4.0 cm³/g, about 0.1 cm³/g to about 3.5 cm³/g, about 0.1 cm³/g to about 3.0 cm³/g, about 0.1 cm³/g to about 2.5 cm³/g, about 0.1 cm³/g to about 2.0 cm³/g, about 0.1 cm³/g to about 1.9 cm³/g, about 0.1 cm³/g to about 1.8 cm³/g, about 0.1 cm³/g to about 1.7 cm³/g, about 0.1 cm³/g to about 1.6 cm³/g, about 0.1 cm³/g to about 1.5 cm³/g, about 0.1 cm³/g to about 1.4 cm³/g, about 0.1 cm³/g to about 1.3 cm³/g, about 0.1 cm³/g to about 1.2 cm³/g, about 0.1 cm³/g to about 1.1, about 0.1 cm³/g to about 1.0 cm³/g, about 0.1 cm³/g to about 0.9 cm³/g, about 0.1 cm³/g to about 0.8 cm³/g, about 0.1 cm³/g to about 0.7 cm³/g, about 0.1 cm³/g to about 0.6 cm³/g, about 0.1 cm³/g to about 0.5 cm³/g, about 0.1 cm³/g to about 0.4 cm³/g, about 0.1 cm³/g to about 0.3 cm³/g, about 0.1 cm³/g to about 0.2 cm³/g, 0.2 cm³/g to about 10.0 cm³/g, about 0.2 cm³/g to about 7.0 cm³/g, about 0.2 cm³/g to about 6.0 cm³/g, about 0.2 cm³/g to about 5.0 cm³/g, about 0.2 cm³/g to about 4.0 cm³/g, about 0.2 cm³/g to about 3.5 cm³/g, about 0.2 cm³/g to about 3.0 cm³/g, about 0.2 cm³/g to about 2.5 cm³/g, about 0.2 cm³/g to about 2.0 cm³/g, about 0.2 cm³/g to about 1.9 cm³/g, about 0.2 cm³/g to about 1.8 cm³/g, about 0.2 cm³/g to about 1.7 cm³/g, about 0.2 cm³/g to about 1.6 cm³/g, about 0.2 cm³/g to about 1.5 cm³/g, about 0.2 cm³/g to about 1.4 cm³/g, about 0.2 cm³/g to about 1.3 cm³/g, about 0.2 cm³/g to about 1.2 cm³/g, about 0.2 cm³/g to about 1.1, about 0.5 cm³/g to about 1.0 cm³/g, about 0.5 cm³/g to about 0.9 cm³/g, about 0.5 cm³/g to about 0.8 cm³/g, about 0.5 cm³/g to about 0.7 cm³/g, about 0.5 cm³/g to about 0.6 cm³/g, about 0.5 cm³/g to about 0.5 cm³/g, about 0.5 cm³/g to about 0.4 cm³/g, about 0.5 cm³/g to about 0.3 cm³/g, 0.5 cm³/g to about 10.0 cm³/g, about 0.5 cm³/g to about 7.0 cm³/g, about 0.5 cm³/g to about 6.0 cm³/g, about 0.5 cm³/g to about 5.0 cm³/g, about 0.5 cm³/g to about 4.0 cm³/g, about 0.5 cm³/g to about 3.5 cm³/g, about 0.5 cm³/g to about 3.0 cm³/g, about 0.5 cm³/g to about 2.5 cm³/g, about 0.5 cm³/g to about 2.0 cm³/g, about 0.5 cm³/g to about 1.9 cm³/g, about 0.5 cm³/g to about 1.8 cm³/g, about 0.5 cm³/g to about 1.7 cm³/g, about 0.5 cm³/g to about 1.6 cm³/g, about 0.5 cm³/g to about 1.5 cm³/g, about 0.5 cm³/g to about 1.4 cm³/g, about 0.5 cm³/g to about 1.3 cm³/g, about 0.5 cm³/g to about 1.2 cm³/g, about 0.5 cm³/g to about 1.1, about 0.5 cm³/g to about 1.0 cm³/g, about 0.5 cm³/g to about 0.9 cm³/g, about 0.5 cm³/g to about 0.8 cm³/g, about 0.5 cm³/g to about 0.7 cm³/g, or about 0.5 cm³/g to about 0.6 cm³/g.

In a particular embodiment, the organosilica material can have a pore volume of about 0.1 cm³/g to about 5.0 cm³/g, particularly about 0.1 cm³/g to about 3.0 cm³/g, particularly about 0.2 cm³/g to about 2.5 cm³/g, or particularly about 0.2 cm³/g to about 1.5 cm³/g.

III.F. Additional Metals

In some embodiments, the organosilica material can further comprise at least one catalyst metal incorporated within the pores of the organosilica material. Exemplary catalyst metals can include, but are not limited to, a Group 6 element, a Group 8 element, a Group 9 element, a Group 10 element or a combination thereof. Exemplary Group 6 elements can include, but are not limited to, chromium, molybdenum, and/or tungsten, particularly including molybdenum and/or tungsten. Exemplary Group 8 elements can include, but are not limited to, iron, ruthenium, and/or osmium. Exemplary Group 9 elements can include, but are not limited to, cobalt, rhodium, and/or iridium, particularly including cobalt. Exemplary Group 10 elements can include, but are not limited to, nickel, palladium and/or platinum.

The catalyst metal can be incorporated into the organosilica material by any convenient method, such as by impregnation, by ion exchange, or by complexation to surface sites. The catalyst metal so incorporated may be employed to promote any one of a number of catalytic transformations commonly conducted in petroleum refining or petrochemicals production. Examples of such catalytic processes can include, but are not limited to, hydrogenation, dehydrogenation, aromatization, aromatic saturation, hydrodesulfurization, olefin oligomerization, polymerization, hydrodenitrogenation, hydrocracking, naphtha reforming, paraffin isomerization, aromatic transalkylation, saturation of double/triple bonds, and the like, as well as combinations thereof.

Thus, in another embodiment, a catalyst material comprising the organosilica material described herein is provided. The catalyst material may optionally comprise a binder or be self-bound. Suitable binders include, but are not limited to, active and inactive materials, synthetic or naturally occurring zeolites, as well as inorganic materials such as clays and/or oxides such as silica, alumina, zirconia, titania, silica-alumina, cerium oxide, magnesium oxide, or combinations thereof. In particular, the binder may be silica-alumina, alumina and/or a zeolite, particularly alumina. Silica-alumina may be either naturally occurring or in the form of gelatinous precipitates or gels including mixtures of silica and metal oxides. It should be noted it is recognized herein that the use of a material in conjunction with a zeolite binder material, i.e., combined therewith or present during its synthesis, which itself is catalytically active may change the conversion and/or selectivity of the finished catalyst. It is also recognized herein that inactive materials can suitably serve as diluents to control the amount of conversion if the present invention is employed in alkylation processes so that alkylation products can be obtained economically and orderly without employing other means for controlling the rate of reaction. These inactive materials may be incorporated into naturally occurring clays, e.g., bentonite and kaolin, to improve the crush strength of the catalyst under commercial operating conditions and function as binders or matrices for the catalyst. The catalysts described herein typically can comprise, in a composited form, a ratio of support material to binder material of about 100 parts support material to about zero parts binder material; about 99 parts support material to about 1 parts binder material; about 95 parts support material to about 5 parts binder material. Additionally or alternatively, the catalysts described herein typically can comprise, in a composited form, a ratio of support material to binder material ranging from about 90 parts support material to about 10 parts binder material to about 10 parts support material to about 90 parts binder material; about 85 parts support material to about 15 parts binder material to about 15 parts support material to about 85 parts binder material; about 80 parts support material to 20 parts binder material to 20 parts support material to 80 parts binder material, all ratios being by weight, typically from 80:20 to 50:50 support material: binder material, preferably from 65:35 to 35:65. Compositing may be done by conventional means including mulling the materials together followed by extrusion of pelletizing into the desired finished catalyst particles.

In some embodiments, the organosilica material can further comprise cationic metal sites incorporated into the network structure. Such cationic metal sites may be incorporated by any convenient method, such as impregnation or complexation to the surface, through an organic precursor, or by some other method. This organometallic material may be employed in a number of hydrocarbon separations conducted in petroleum refining or petrochemicals production. Examples of such compounds to be desirably separated from petrochemicals/fuels can include olefins, paraffins, aromatics, and the like.

Additionally or alternatively, the organosilica material can further comprise a surface metal incorporated within the pores of the organosilica material. The surface metal can be selected from a Group 1 element, a Group 2 element, a Group 13 element, and a combination thereof. When a Group 1 element is present, it can preferably comprise or be sodium and/or potassium. When a Group 2 element is present, it can include, but may not be limited to, magnesium and/or calcium. When a Group 13 element is present, it can include, but may not be limited to, boron and/or aluminum.

One or more of the Group 1, 2, 6, 8-10 and/or 13 elements may be present on an exterior and/or interior surface of the organosilica material. For example, one or more of the Group 1, 2 and/or 13 elements may be present in a first layer on the organosilica material and one or more of the Group 6, 8, 9 and/or 10 elements may be present in a second layer, e.g., at least partially atop the Group 1, 2 and/or 13 elements. Additionally or alternatively, only one or more Group 6, 8, 9 and/or 10 elements may present on an exterior and/or interior surface of the organosilica material. The surface metal(s) can be incorporated into/onto the organosilica material by any convenient method, such as by impregnation, deposition, grafting, co-condensation, by ion exchange, and/or the like.

III. Methods of Making Organosilica Materials

In another embodiment, methods of producing the organosilica material described herein are provided. The method comprises:

(a) providing an aqueous mixture that contains essentially no structure directing agent and/or porogen;

(b) adding at least one compound of Formula $[R^1R^2SiCH_2]_3$ (Ia) into the aqueous mixture to form a solution, wherein each $R^1$ can be a $C_1$-$C_4$ alkoxy group and each $R^2$ can be a $C_1$-$C_4$ alkoxy group or a $C_1$-$C_4$ alkyl group;

(c) adding at least one source of trivalent metal oxide to the solution:

(d) aging the solution to produce a pre-product; and (e) drying the pre-product to obtain an organosilica material which is a polymer comprising at least one independent monomer of Formula (I) as described herein.

Additionally or alternatively, the at least one compound of Formula $[R^1R^2SiCH_2]_3$ (Ia) can be added in step (b) as at least partially hydroxylated and/or as at least partially polymerized/oligomerized, such that each $R^1$ can more broadly represent a hydroxyl group, a $C_1$-$C_4$ alkoxy group or an oxygen atom bonded to a silicon atom of another siloxane and each $R^2$ can more broadly represent a hydroxyl group, a $C_1$-$C_4$ alkoxy group, a $C_1$-$C_4$ alkyl group, or an oxygen atom bonded to a silicon atom of another siloxane. In other words, an unaged pre-product can be added in step (b), in addition to or as an alternative to the monomeric (at least one) compound of Formula $[R^1R^2SiCH_2]_3$ (Ia).

III.A. Aqueous Mixture

The organosilica materials described herein may be made using essentially no structure directing agent or porogen. Thus, the aqueous mixture contains essentially no added structure directing agent and/or no added porogen.

As used herein, "no added structure directing agent," and "no added porogen" means either (i) there is no component present in the synthesis of the organosilica material that aids in and/or guides the polymerization and/or polycondensing and/or organization of the building blocks that form the framework of the organosilica material; or (ii) such component is present in the synthesis of the organosilica material in a minor, or a non-substantial, or a negligible amount such that the component cannot be said to aid in and/or guide the polymerization and/or polycondensing and/or organization of the building blocks that form the framework of the organosilica material. Further, "no added structure directing agent" is synonymous with "no added template" and "no added templating agent."

1. Structure Directing Agent

Examples of a structure directing agent can include, but are not limited to, non-ionic surfactants, ionic surfactants, cationic surfactants, silicon surfactants, amphoteric surfactants, polyalkylene oxide surfactants, fluorosurfactants, colloidal crystals, polymers, hyper branched molecules, star-shaped molecules, macromolecules, dendrimers, and combinations thereof. Additionally or alternatively, the surface directing agent can comprise or be a poloxamer, a triblock polymer, a tetraalkylammonium salt, a nonionic polyoxyethylene alkyl, a Gemini surfactant, or a mixture thereof. Examples of a tetraalkylammonium salt can include, but are not limited to, cetyltrimethylammonium halides, such as cetyltrimethylammonium chloride (CTAC), cetyltrimethylammonium bromide (CTAB), and octadecyltrimethylammonium chloride. Other exemplary surface directing agents can additionally or alternatively include hexadecyltrimethylammonium chloride and/or cetylpyridinium bromide.

Poloxamers are block copolymers of ethylene oxide and propylene oxide, more particularly nonionic triblock copolymers composed of a central hydrophobic chain of polyoxypropylene (poly(propylene oxide)) flanked by two hydrophilic chains of polyoxyethylene (poly(ethylene oxide)). Specifically, the term "poloxamer" refers to a polymer having the formula $HO(C_2H_4))a(C_3H_6O)_b(C_2H_4O)_aH$ in which "a" and "b" denote the number of polyoxyethylene and polyoxypropylene units, respectively. Poloxamers are also known by the trade name Pluronic, for example Pluronic® 123 and Pluronic® F 127. An additional triblock polymer is B50-6600.

Nonionic polyoxyethylene alkyl ethers are known by the trade name Brij®, for example Brij® 56, Brij® 58, Brij® 76, Brij® 78. Gemini surfactants are compounds having at least two hydrophobic groups and at least one or optionally two hydrophilic groups per molecule have been introduced.

2. Porogen

A porogen material is capable of forming domains, discrete regions, voids and/or pores in the organosilica material. An example of a porogen is a block copolymer (e.g., a di-block polymer). As used herein, porogen does not include water. Examples of polymer porogens can include, but are not limited to, polyvinyl aromatics, such as polystyrenes, polyvinylpyridines, hydrogenated polyvinyl aromatics, polyacrylonitriles, polyalkylene oxides, such as polyethylene oxides and polypropylene oxides, polyethylenes, polylactic acids, polysiloxanes, polycaprolactones, polycaprolactams, polyurethanes, polymethacrylates, such as polymethylmethacrylate or polymethacrylic acid, polyacrylates, such as polymethylacrylate and polyacrylic acid, polydienes such as polybutadienes and polyisoprenes, polyvinyl chlorides, polyacetals, and amine-capped alkylene oxides, as well as combinations thereof.

Additionally or alternatively, porogens can be thermoplastic homopolymers and random (as opposed to block) copolymers. As used herein, "homopolymer" means compounds comprising repeating units from a single monomer. Suitable thermoplastic materials can include, but are not limited to, homopolymers or copolymers of polystyrenes, polyacrylates, polymethacrylates, polybutadienes, polyisoprenes, polyphenylene oxides, polypropylene oxides, polyethylene oxides, poly(dimethylsiloxanes), polytetrahydrofurans, polyethylenes, polycyclohexylethylenes, polyethyloxazolines, polyvinylpyridines, polycaprolactones, polylactic acids, copolymers of these materials and mixtures of these materials. Examples of polystyrene include, but are not limited to anionic polymerized polystyrene, syndiotactic polystyrene, unsubstituted and substituted polystyrenes (for example, poly(α-methyl styrene)). The thermoplastic materials may be linear, branched, hyperbranched, dendritic, or star like in nature.

Additionally or alternatively, the porogen can be a solvent. Examples of solvents can include, but are not limited to, ketones (e.g., cyclohexanone, cyclopentanone, 2-heptanone, cycloheptanone, cyclooctanone, cyclohexylpyrrolidinone, methyl isobutyl ketone, methyl ethyl ketone, acetone), carbonate compounds (e.g., ethylene carbonate, propylene carbonate), heterocyclic compounds (e.g., 3-methyl-2-oxazolidinone, dimethylimidazolidinone, N-methylpyrrolidone, pyridine), cyclic ethers (e.g., dioxane, tetrahydrofuran), chain ethers (e.g., diethyl ether, ethylene glycol dimethyl ether, propylene glycol dimethyl ether, tetraethylene glycol dimethyl ether, polyethylene glycol dimethyl ether, ethylene glycol monomethyl ether, ethylene glycol monoethyl ether, propylene glycol monomethyl ether (PGME), triethylene glycol monobutyl ether, propylene glycol monopropyl ether, triethylene glycol monomethyl ether, diethylene glycol ethyl ether, diethylene glycol methyl ether, dipropylene glycol methyl ether, dipropylene glycol dimethyl ether, propylene glycol phenyl ether, tripropylene glycol methyl ether), alcohols (e.g., methanol, ethanol), polyhydric alcohols (e.g., ethylene glycol, propylene glycol, polyethylene glycol, polypropylene glycol, glycerin, dipropylene glycol), nitrile compounds (e.g., acetonitrile, glutarodinitrile, methoxyacetonitrile, propionitrile, benzonitrile), esters (e.g., ethyl acetate, butyl acetate, methyl lactate, ethyl lactate, methyl methoxypropionate, ethyl ethoxypropionate, methyl pyruvate, ethyl pyruvate, propyl pyruvate, 2-methoxyethyl acetate, ethylene glycol monoethyl ether acetate, propylene glycol monomethyl ether acetate (PGMEA), butyrolactone, phosphoric acid ester, phosphonic acid ester), aprotic polar substances (e.g., dimethyl sulfoxide, sulfolane, dimethylformamide, dimethylacetamide), nonpolar solvents (e.g., toluene, xylene, mesitylene), chlorine-based solvents (e.g., methylene dichloride, ethylene dichloride), benzene, dichlorobenzene, naphthalene, diphenyl ether, diisopropylbenzene, triethylamine, methyl benzoate, ethyl benzoate, butyl benzoate, monomethyl ether acetate hydroxy ethers such as dibenzylethers, diglyme, triglyme, and mixtures thereof.

3. Base/Acid

In various embodiments, the aqueous mixture used in methods provided herein can comprise a base and/or an acid.

In certain embodiments where the aqueous mixture comprises a base, the aqueous mixture can have a pH from about 8 to about 15, from about 8 to about 14.5, from about 8 to about 14, from about 8 to about 13.5, from about 8 to about 13, from about 8 to about 12.5, from about 8 to about 12, from about 8 to about 11.5, from about 8 to about 11, from about 8 to about 10.5, from about 8 to about 10, from about 8 to about 9.5, from about 8 to about 9, from about 8 to about 8.5, from about 8.5 to about 15, from about 8.5 to about 14.5, from about 8.5 to about 14, from about 8.5 to about 13.5, from about 8.5 to about 13, from about 8.5 to about 12.5, from about 8.5 to about 12, from about 8.5 to about 11.5, from about 8.5 to about 11, from about 8.5 to about 10.5, from about 8.5 to about 10, from about 8.5 to about 9.5, from about 8.5 to about 9, from about 9 to about 15, from about 9 to about 14.5, from about 9 to about 14, from about 9 to about 13.5, from about 9 to about 13, from about 9 to about 12.5, from about 9 to about 12, from about 9 to about 11.5, from about 9 to about 11, from about 9 to about 10.5, from about 9 to about 10, from about 9 to about 9.5, from about 9.5 to about 15, from about 9.5 to about 14.5, from about 9.5 to about 14, from about 9.5 to about 13.5, from about 9.5 to about 13, from about 9.5 to about 12.5, from about 9.5 to about 12, from about 9.5 to about 11.5, from about 9.5 to about 11, from about 9.5 to about 10.5, from about 9.5 to about 10, from about 10 to about 15, from about 10 to about 14.5, from about 10 to about 14, from about 10 to about 13.5, from about 10 to about 13, from about 10 to about 12.5, from about 10 to about 12, from about 10 to about 11.5, from about 10 to about 11, from about 10 to about 10.5, from about 10.5 to about 15, from about 10.5 to about 14.5, from about 10.5 to about 14, from about 10.5 to about 13.5, from about 10.5 to about 13, from about 10.5 to about 12.5, from about 10.5 to about 12, from about 10.5 to about 11.5, from about 10.5 to about 11, from about 11 to about 15, from about 11 to about 14.5, from about 11 to about 14, from about 11 to about 13.5, from about 11 to about 13, from about 11 to about 12.5, from about 11 to about 12, from about 11 to about 11.5, from about 11.5 to about 15, from about 11.5 to about 14.5, from about 11.5 to about 14, from about 11.5 to about 13.5, from about 11.5 to about 13, from about 11.5 to about 12.5, from about 11.5 to about 12, from about 12 to about 15, from about 12 to about 14.5, from about 12 to about 14, from about 12 to about 13.5, from about 12 to about 13, from about 12 to about 12.5, from about 12.5 to about 15, from about 12.5 to about 14.5, from about 12.5 to about 14, from about 12.5 to about 13.5, from about 12.5 to about 13, from about 12.5 to about 15, from about 12.5 to about 14.5, from about 12.5 to about 14, from about 12.5 to about 13.5, from about 12.5 to about 13, from about 13 to about 15, from about 13 to about 14.5, from about 13 to about 14, from about 13 to about 13.5, from about 13.5 to about 15, from about 13.5 to about 14.5, from about 13.5 to about 14, from about 14 to about 15, from about 14 to about 14.5, and from about 14.5 to about 15.

In a particular embodiment comprising a base, the pH can be from about 9 to about 15, from about 9 to about 14 or from about 8 to about 14.

Exemplary bases can include, but are not limited to, sodium hydroxide, potassium hydroxide, lithium hydroxide, pyridine, pyrrole, piperazine, pyrrolidine, piperidine, picoline, monoethanolamine, diethanolamine, dimethylmonoethanolamine, monomethyldiethanolamine, triethanolamine, diazabicyclooctane, diazabicyclononane, diazabicycloundecene, tetramethylammonium hydroxide, tetraethylammonium hydroxide, tetrapropylammonium hydroxide, tetrabutylammonium hydroxide, ammonia, ammonium hydroxide, methylamine, ethylamine, propylamine, butylamine, pentylamine, hexylamine, octylamine, nonylamine, decylamine, N,N-dimethylamine, N,N-diethylamine, N,N-dipropylamine, N,N-dibutylamine, trimethylamine, triethylamine, tripropylamine, tributylamine, cyclohexylamine, trimethylimidine, 1-amino-3-methylbutane, dimethylglycine, 3-amino-3-methylamine, and the like. These bases may be used either singly or in combination. In a particular embodiment, the base can comprise or be sodium hydroxide and/or ammonium hydroxide.

In certain embodiments where the aqueous mixture comprises an acid, the aqueous mixture can have a pH from about 0.01 to about 6.0, from about 0.01 to about 5, from about 0.01 to about 4, from about 0.01 to about 3, from about 0.01 to about 2, from about 0.01 to about 1, about 0.1 to about 6.0, about 0.1 to about 5.5, about 0.1 to about 5.0, from about 0.1 to about 4.8, from about 0.1 to about 4.5, from about 0.1 to about 4.2, from about 0.1 to about 4.0, from about 0.1 to about 3.8, from about 0.1 to about 3.5, from about 0.1 to about 3.2, from about 0.1 to about 3.0, from about 0.1 to about 2.8, from about 0.1 to about 2.5, from about 0.1 to about 2.2, from about 0.1 to about 2.0, from about 0.1 to about 1.8, from about 0.1 to about 1.5, from about 0.1 to about 1.2, from about 0.1 to about 1.0, from about 0.1 to about 0.8, from about 0.1 to about 0.5, from about 0.1 to about 0.2, about 0.2 to about 6.0, about 0.2 to about 5.5, from about 0.2 to about 5, from about 0.2 to about 4.8, from about 0.2 to about 4.5, from about 0.2 to about 4.2, from about 0.2 to about 4.0, from about 0.2 to about 3.8, from about 0.2 to about 3.5, from about 0.2 to about 3.2, from about 0.2 to about 3.0, from about 0.2 to about 2.8, from about 0.2 to about 2.5, from about 0.2 to about 2.2, from about 0.2 to about 2.0, from about 0.2 to about 1.8, from about 0.2 to about 1.5, from about 0.2 to about 1.2, from about 0.2 to about 1.0, from about 0.2 to about 0.8, from about 0.2 to about 0.5, about 0.5 to about 6.0, about 0.5 to about 5.5, from about 0.5 to about 5, from about 0.5 to about 4.8, from about 0.5 to about 4.5, from about 0.5 to about 4.2, from about 0.5 to about 4.0, from about 0.5 to about 3.8, from about 0.5 to about 3.5, from about 0.5 to about 3.2, from about 0.5 to about 3.0, from about 0.5 to about 2.8, from about 0.5 to about 2.5, from about 0.5 to about 2.2, from about 0.5 to about 2.0, from about 0.5 to about 1.8, from about 0.5 to about 1.5, from about 0.5 to about 1.2, from about 0.5 to about 1.0, from about 0.5 to about 0.8, about 0.8 to about 6.0, about 0.8 to about 5.5, from about 0.8 to about 5, from about 0.8 to about 4.8, from about 0.8 to about 4.5, from about 0.8 to about 4.2, from about 0.8 to about 4.0, from about 0.8 to about 3.8, from about 0.8 to about 3.5, from about 0.8 to about 3.2, from about 0.8 to about 3.0, from about 0.8 to about 2.8, from about 0.8 to about 2.5, from about 0.8 to about 2.2, from about 0.8 to about 2.0, from about 0.8 to about 1.8, from about 0.8 to about 1.5, from about 0.8 to about 1.2, from about 0.8 to about 1.0, about 1.0 to about 6.0, about 1.0 to about 5.5, from about 1.0 to about 5.0, from about 1.0 to about 4.8, from about 1.0 to about 4.5, from about 1.0 to about 4.2, from about 1.0 to about 4.0, from about 1.0 to about 3.8, from about 1.0 to about 3.5, from about 1.0 to about 3.2, from about 1.0 to about 3.0, from about 1.0 to about 2.8, from about 1.0 to about 2.5, from about 1.0 to about 2.2, from about 1.0 to about 2.0, from about 1.0 to about 1.8, from about 1.0 to about 1.5, from about 1.0 to about 1.2, about 1.2 to about 6.0, about 1.2 to about 5.5, from about 1.2 to about 5.0, from about 1.2 to about 4.8, from about 1.2 to about 4.5, from about 1.2 to about 4.2, from about 1.2 to about 4.0, from about 1.2 to about 3.8, from about 1.2 to about 3.5, from about 1.2 to about 3.2, from about 1.2 to about 3.0, from about 1.2 to about 2.8, from about 1.2 to about 2.5, from about 1.2 to about 2.2, from about 1.2 to about 2.0, from about 1.2 to about 1.8, from about 1.2 to about 1.5, about 1.5 to about 6.0, about 1.5 to about 5.5, from about 1.5 to about 5.0, from about 1.5 to about 4.8, from about 1.5 to about 4.5, from about 1.5 to about 4.2, from about 1.5 to about 4.0, from about 1.5 to about 3.8, from about 1.5 to about 3.5, from about 1.5 to about 3.2, from about 1.5 to about 3.0, from about 1.5 to about 2.8, from about 1.5 to about 2.5, from about 1.5 to about 2.2, from about 1.5 to about 2.0, from about 1.5 to about 1.8, about 1.8 to about 6.0, about 1.8 to about 5.5, from about 1.8 to about 5.0, from about 1.8 to about 4.8, from about 1.8 to about 4.5, from about 1.8 to about 4.2, from about 1.8 to about 4.0, from about 1.8 to about 3.8, from about 1.8 to about 3.5, from about 1.8 to about 3.2, from about 1.8 to about 3.0, from about 1.8 to about 2.8, from about 1.8 to about 2.5, from about 1.8 to about 2.2, from about 1.8 to about 2.0, about 2.0 to about 6.0, about 2.0 to about 5.5, from about 2.0 to about 5.0, from about 2.0 to about 4.8, from about 2.0 to about 4.5, from about 2.0 to about 4.2, from about 2.0 to about 4.0, from about 2.0 to about 3.8, from about 2.0 to about 3.5, from about 2.0 to about 3.2, from about 2.0 to about 3.0, from about 2.0 to about 2.8, from about 2.0 to about 2.5, from about 2.0 to about 2.2, about 2.2 to about 6.0, about 2.2 to about 5.5, from about 2.2 to about 5.0, from about 2.2 to about 4.8, from about 2.2 to about 4.5, from about 2.2 to about 4.2, from about 2.2 to about 4.0, from about 2.2 to about 3.8, from about 2.2 to about 3.5, from about 2.2 to about 3.2, from about 2.2 to about 3.0, from about 2.2 to about 2.8, from about 2.2 to about 2.5, about 2.5 to about 6.0, about 2.5 to about 5.5, from about 2.5 to about 5.0, from about 2.5 to about 4.8, from about 2.5 to about 4.5, from about 2.5 to about 4.2, from about 2.5 to about 4.0, from about 2.5 to about 3.8, from about 2.5 to about 3.5, from about 2.5 to about 3.2, from about 2.5 to about 3.0, from about 2.5 to about 2.8, from about 2.8 to about 6.0, about 2.8 to about 5.5, from about 2.8 to about 5.0, from about 2.8 to about 4.8, from about 2.8 to about 4.5, from about 2.8 to about 4.2, from about 2.8 to about 4.0, from about 2.8 to about 3.8, from about 2.8 to about 3.5, from about 2.8 to about 3.2, from about 2.8 to about 3.0, from about 3.0 to about 6.0, from about 3.5 to about 5.5, from about 3.0 to about 5.0, from about 3.0 to about 4.8, from about 3.0 to about 4.5, from about 3.0 to about 4.2, from about 3.0 to about 4.0, from about 3.0 to about 3.8, from about 3.0 to about 3.5, from about 3.0 to about 3.2, from about 3.2 to about 6.0, from about 3.2 to about 5.5, from about 3.2 to about 5, from about 3.2 to about 4.8, from about 3.2 to about 4.5, from about 3.2 to about 4.2, from about 3.2 to about 4.0, from about 3.2 to about 3.8, from about 3.2 to about 3.5, from about 3.5 to about 6.0, from about 3.5 to about 5.5, from about 3.5 to about 5, from about 3.5 to about 4.8, from about 3.5 to about 4.5, from about 3.5 to about 4.2, from about 3.5 to about 4.0, from about 3.5 to about 3.8, from about 3.8 to about 5, from about 3.8 to about 4.8, from about 3.8 to about 4.5, from about 3.8 to about 4.2, from about 3.8 to about 4.0, from about 4.0 to about 6.0, from about 4.0 to about 5.5, from about 4.0 to about 5, from about 4.0 to about 4.8, from about 4.0 to about 4.5, from about 4.0 to about 4.2, from about 4.2 to about 5, from about 4.2 to about 4.8, from about 4.2 to about 4.5, from about 4.5 to about 5, from about 4.5 to about 4.8, or from about 4.8 to about 5.

In a particular embodiment comprising an acid, the pH can be from about 0.01 to about 6.0, about 0.2 to about 6.0, about 0.2 to about 5.0 or about 0.2 to about 4.5.

Exemplary acids can include, but are not limited to, inorganic acids such as hydrochloric acid, nitric acid, sulfuric acid, hydrofluoric acid, phosphoric acid, boric acid and oxalic acid; and organic acids such as acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, shikimic acid, 2-ethylhexanoic acid, oleic acid, stearic acid, linoleic acid, linolenic acid, salicylic acid, benzoic acid, p-amino-benzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, tartaric acid, succinic acid, itaconic acid, mesaconic acid, citraconic acid, malic acid, a hydrolysate of glutaric acid, a hydrolysate of maleic anhydride, a hydrolysate of phthalic anhydride, and the like. These acids may be used either singly or in combination. In a particular embodiment, the acid can comprise or be hydrochloric acid.

III.B. Compounds of Formula (Ia)

The methods provided herein comprise the step of adding at least one compound of Formula $[R^1R^2SiCH_2]_3$ (Ia) into the aqueous mixture to form a solution, wherein each $R^1$ can be a $C_1$-$C_4$ alkoxy group and each $R^2$ can be a $C_1$-$C_4$ alkoxy group or a $C_1$-$C_4$ alkyl group.

In one embodiment, each $R^1$ can comprise a $C_1$-$C_3$ alkoxy or methoxy or ethoxy.

Additionally or alternatively, each $R^2$ can comprise a $C_1$-$C_4$ alkoxy, a $C_1$-$C_3$ alkoxy or methoxy or ethoxy. Additionally or alternatively, each $R^2$ can comprise methyl, ethyl or propyl, such as a methyl or ethyl.

Additionally or alternatively, each $R^1$ can be a $C_1$-$C_2$ alkoxy group and $R^2$ can be a $C_1$-$C_2$ alkoxy group or a $C_1$-$C_2$ alkyl group Additionally or alternatively, each $R^1$ can be methoxy or ethoxy and each $R^2$ can be methyl or ethyl.

In a particular embodiment, each $R^1$ and $R^2$ can be ethoxy, such that the compound corresponding to Formula (Ia) can be 1,1,3,3,5,5-hexaethoxy-1,3,5-trisilacyclohexane, ($[(EtO)_2SiCH_2]_3$).

In a particular embodiment, each $R^1$ can be ethoxy and each $R^2$ can be methyl, such that compound corresponding to Formula (Ia) can be 1,3,5-trimethyl-1,3,5-triethoxy-1,3,5-trisilacyclohexane, ($[EtOCH_3SiCH_2]_3$).

In various aspects, more than one compound of Formula (Ia) (e.g., same or different compound) may be added to the aqueous mixture to form a solution. For example, $[(EtO)_2SiCH_2]_3$ and $[EtOCH_3SiCH_2]_3$ may both be added to the aqueous mixture to form a solution.

As mentioned hereinabove, the at least one compound of Formula (Ia) can additionally or alternatively be at least partially hydroxylated and/or polymerized/oligomerized when added into the aqueous mixture to form a solution.

When more than one compound of Formula (Ia) is used, the respective compounds may be used in a wide variety of molar ratios. For example, if two compounds of Formula (Ia) are used, the molar ratio of each compound may vary from 1:99 to 99:1, such as from 10:90 to 90:10. The use of different compounds of Formula (Ia) allows to tailor the properties of the organosilica materials made by the process of the invention, as will be further explained in the examples and in the section of this specification describing the properties of the organosilicas made by the present processes.

III.C. Sources of Trivalent Metal Oxides

In additional embodiments, the methods provided herein can comprise adding to the aqueous solution a source of a trivalent metal oxide.

Sources of trivalent metal oxides can include, but are not limited to, corresponding salts, alkoxides, oxides, and/or hydroxides of the trivalent metal, e.g., aluminum sulphate, aluminum nitrate, colloidal alumina, aluminum trihydroxide, hydroxylated alumina, $Al_2O_3$, aluminum halides (e.g., $AlCl_3$), $NaAlO_2$, boron nitride, $B_2O_3$ and/or $H_3BO_3$.

In various aspects, the source of trivalent metal oxide may be a compound of Formula $M^3(OZ^{15})_3$ (IIa), wherein $M^3$ can be a Group 13 metal and each $Z^{15}$ independently can be a $C_1$-$C_6$ alkyl group.

In one embodiment, $M^3$ can be B, Al, Ga, In, Tl, or Uut. In particular, $M^3$ can be Al or B.

Additionally or alternatively, each $Z^{15}$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^{15}$ can be methyl, ethyl, propyl or butyl.

Additionally or alternatively, $M^3$ can be Al or B and each $Z^{15}$ can be methyl, ethyl, propyl or butyl.

In a particular embodiment, $M^3$ can be Al and each $Z^{15}$ can be methyl, such that compound corresponding to Formula (IIa) can be aluminum trimethoxide.

In a particular embodiment, $M^3$ can be Al and each $Z^{15}$ can be ethyl, such that compound corresponding to Formula (IIa) can be aluminum triethoxide.

In a particular embodiment, $M^3$ can be Al and each $Z^{15}$ can be propyl, such that compound corresponding to Formula (IIa) can be aluminum isopropoxide.

In a particular embodiment, $M^3$ can be Al and each $Z^{15}$ can be butyl, such that compound corresponding to Formula (IIa) can be aluminum tri-sec-butoxide.

In another particular embodiment, the compound of Formula (Ia) can be 1,1,3,3,5,5-hexaethoxy-1,3,5-trisilacyclohexane, ($[(EtO)_2SiCH_2]_3$) and the compound of Formula (IIa) can be selected from the group consisting of aluminum trimethoxide, aluminum triethoxide, aluminum isopropoxide, and aluminum tri-sec-butoxide.

In another particular embodiment, the compound of Formula (Ia) can be 1,1,3,3,5,5-hexaethoxy-1,3,5-trisilacyclohexane, ($[(EtO)_2SiCH_2]_3$) and the compound of Formula (IIa) can be aluminum tri-sec-butoxide.

Additionally or alternatively, the source of trivalent metal oxide may be a compound of Formula $(Z^{16}O)_2M^4$-O-Si$(OZ^{17})_3$ (IIIa), wherein $M^4$ can be a Group 13 metal and $Z^{16}$ and $Z^{17}$ each independently can be a $C_1$-$C_6$ alkyl group.

In one embodiment, $M^4$ can be B, Al, Ga, In, Tl, or Uut. In particular, $M^4$ can be Al or B.

Additionally or alternatively, each $Z^{16}$ and each $Z^{17}$ independently can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^{16}$ and $Z^{17}$ each independently can be methyl, ethyl, propyl or butyl.

Additionally or alternatively, $M^4$ can be Al or B and each $Z^{16}$ and each $Z^{17}$ independently can be methyl, ethyl, propyl or butyl.

Additionally or alternatively, the source of a trivalent metal oxide may be a source of a compound of Formula (IIa) (e.g., $AlCl_3$), and/or a source of a compound of Formula (IIIa).

The molar ratio of compound of Formula (Ia) to trivalent metal oxide may vary within wide limits, such as from about 99:1 to about 1:99, from about 30:1 to about 1:1, from about 25:1 to about 1:1, from about 20:1 to about 3:1 or from about 20:1 to about 5:1.

III.D. Compounds of Formula (Va)

In additional embodiments, the methods provided herein can further comprise adding to the aqueous solution a compound of Formula $R^3OR^4R^5R^6Si$ (Va) to obtain an organosilica material which is a copolymer comprising at least one independent unit of Formula (I) as described herein, at least one other trivalent metal oxide monomer (e.g., at least one independent unit of Formula (II) and/or Formula (III)) as described herein, optionally at least one independent unit of Formula (IV) as described herein, and at least one independent unit of Formula (V) as described herein, wherein each $R^3$ can be a $C_1$-$C_6$ alkyl group, and $R^4$, $R^5$ and $R^6$ each independently can be selected from the group consisting of a $C_1$-$C_6$ alkyl group, a $C_1$-$C_6$ alkoxy group, a nitrogen-containing $C_1$-$C_{10}$ alkyl group, a nitrogen-containing heteroaralkyl group, and a nitrogen-containing optionally substituted heterocycloalkyl group.

In one embodiment, each $R^3$ can be a $C_1$-$C_5$ alkyl group, a $C_1$-$C_4$ alkyl group, a $C_1$-$C_3$ alkyl group, a $C_1$-$C_2$ alkyl group, or methyl. In particular, $R^3$ can be methyl or ethyl.

Additionally or alternatively, each $R^4$, $R^5$ and $R^6$ can be each independently a $C_1$-$C_5$ alkyl group, a $C_1$-$C_4$ alkyl group, a $C_1$-$C_3$ alkyl group, a $C_1$-$C_2$ alkyl group, or methyl.

Additionally or alternatively, each $R^3$ can be a $C_1$-$C_2$ alkyl group and $R^4$, $R^5$ and $R^6$ can be each independently a $C_1$-$C_2$ alkyl group.

Additionally or alternatively, $R^4$, $R^5$ and $R^6$ can be each independently a $C_1$-$C_5$ alkoxy group, a $C_1$-$C_4$ alkoxy group, a $C_1$-$C_3$ alkoxy group, a $C_1$-$C_2$ alkoxy group, or methoxy.

Additionally or alternatively, each $R^3$ can be a $C_1$-$C_2$ alkyl group and $R^4$, $R^5$ and $R^6$ can be each independently a $C_1$-$C_2$ alkoxy group.

Additionally or alternatively, each $R^3$ can be a $C_1$-$C_2$ alkyl group and $R^4$, $R^5$ and $R^6$ can be each independently a $C_1$-$C_2$ alkyl group or a $C_1$-$C_2$ alkoxy group.

Additionally or alternatively, $R^4$, $R^5$ and $R^6$ can be each independently a nitrogen-containing $C_1$-$C_9$ alkyl group, a nitrogen-containing $C_1$-$C_8$ alkyl group, a nitrogen-containing $C_1$-$C_7$ alkyl group, a nitrogen-containing $C_1$-$C_6$ alkyl group, a nitrogen-containing $C_1$-$C_5$ alkyl group, a nitrogen-containing $C_1$-$C_4$ alkyl group, a nitrogen-containing $C_1$-$C_3$ alkyl group, a nitrogen-containing $C_1$-$C_2$ alkyl group, or a methylamine. In particular, $R^4$, $R^5$ and $R^6$ can be each independently a nitrogen-containing $C_2$-$C_{10}$ alkyl group, a nitrogen-containing $C_3$-$C_{10}$ alkyl group, a nitrogen-containing $C_3$-$C_9$ alkyl group, or a nitrogen-containing $C_3$-$C_8$ alkyl group. The aforementioned nitrogen-containing alkyl groups may have one or more nitrogen atoms (e.g., 2, 3, etc.). Examples of nitrogen-containing $C_1$-$C_{10}$ alkyl groups include, but are not limited to,

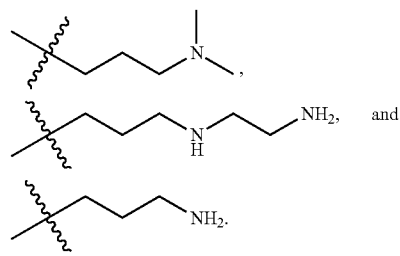

Additionally or alternatively, each $R^3$ can be a $C_1$-$C_2$ alkyl group and $R^4$, $R^5$ and $R^6$ can be each independently a nitrogen-containing $C_3$-$C_8$ alkyl group.

Additionally or alternatively, each $R^3$ can be a $C_1$-$C_2$ alkyl group and $R^4$, $R^5$ and $R^6$ can be each independently a $C_1$-$C_2$ alkyl group, a $C_1$-$C_2$ alkoxy group or a nitrogen-containing $C_3$-$C_8$ alkyl group.

Additionally or alternatively, $R^4$, $R^5$ and $R^6$ can be each independently a nitrogen-containing heteroaralkyl group. The nitrogen-containing heteroaralkyl group can be a nitrogen-containing $C_4$-$C_{12}$ heteroaralkyl group, a nitrogen-containing $C_4$-$C_{10}$ heteroaralkyl group, or a nitrogen-containing $C_4$-$C_8$ heteroaralkyl group. Examples of nitrogen-containing heteroaralkyl groups include but are not limited to pyridinylethyl, pyridinylpropyl, pyridinylmethyl, indolylmethyl, pyrazinylethyl, and pyrazinylpropyl. The aforementioned nitrogen-containing heteroaralkyl groups may have one or more nitrogen atoms (e.g., 2, 3, etc.).

Additionally or alternatively, each $R^3$ can be a $C_1$-$C_2$ alkyl group and $R^4$, $R^5$ and $R^6$ can be each independently a nitrogen-containing heteroaralkyl group.

Additionally or alternatively, each $R^3$ can be a $C_1$-$C_2$ alkyl group and $R^4$, $R^5$ and $R^6$ can be each independently a $C_1$-$C_2$ alkyl group, a $C_1$-$C_2$ alkoxy group, a nitrogen-containing $C_3$-$C_8$ alkyl group or a nitrogen-containing heteroaralkyl group.

Additionally or alternatively, $R^4$, $R^5$ and $R^6$ can be each independently a nitrogen-containing heterocycloalkyl group, wherein the heterocycloalkyl group may be optionally substituted with a $C_1$-$C_6$ alkyl group, particularly a $C_1$-$C_4$ alkyl group. The nitrogen-containing heterocycloalkyl group can be a nitrogen-containing $C_4$-$C_{12}$ heterocycloalkyl group, a nitrogen-containing $C_4$-$C_{10}$ heterocycloalkyl group, or a nitrogen-containing $C_4$-$C_8$ heterocycloalkyl group. Examples of nitrogen-containing heterocycloalkyl groups include but are not limited to piperazinylethyl, piperazinylpropyl, piperidinylethyl, piperidinylpropyl. The aforementioned nitrogen-containing heterocycloalkyl groups may have one or more nitrogen atoms (e.g., 2, 3, etc.).

Additionally or alternatively, each $R^3$ can be a $C_1$-$C_2$ alkyl group and $R^4$, $R^5$ and $R^6$ can be each independently a nitrogen-containing optionally substituted heterocycloalkyl group.

Additionally or alternatively, each $R^3$ can be a $C_1$-$C_2$ alkyl group and $R^4$, $R^5$ and $R^6$ can be each independently a $C_1$-$C_2$ alkyl group, a $C_1$-$C_2$ alkoxy group, a nitrogen-containing $C_3$-$C_8$ alkyl group, a nitrogen-containing heteroaralkyl group, or a nitrogen-containing optionally substituted heterocycloalkyl group.

Additionally or alternatively, each $R^3$ can be a $C_1$-$C_2$ alkyl group and $R^4$, $R^5$ and $R^6$ can be each independently a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroaralkyl group, or a nitrogen-containing optionally substituted $C_4$-$C_{10}$ heterocycloalkyl group.

In a particular embodiment, $R^3$ can be ethyl and $R^4$, $R^5$ and $R^6$ can be ethoxy, such that the compound corresponding to Formula (Va) can be tetraethyl orthosilicate (TEOS) ((EtO)$_4$Si).

In another particular embodiment, the compound of Formula (Ia) can be 1,1,3,3,5,5-hexaethoxy-1,3,5-trisilacyclohexane ([(EtO)$_2$SiCH$_2$]$_3$), and the compound of Formula (Va) can be tetraethyl orthosilicate (TEOS) ((EtO)$_4$Si).

In another particular embodiment, $R^3$ can be ethyl, $R^4$ can be methyl and $R^5$ and $R^6$ can be ethoxy, such that the compound corresponding to Formula (Va) can be methyltriethoxysilane (MTES) ((EtO)$_3$CH$_3$Si).

In another particular embodiment, the compound of Formula (Ia) can be 1,1,3,3,5,5-hexaethoxy-1,3,5-trisilacyclohexane ([(EtO)$_2$SiCH$_2$]$_3$), the trivalent metal oxide source can be aluminum tri-sec-butoxide, and the compound of Formula (Va) can be methyltriethoxysilane (MTES) ((EtO)$_3$CH$_3$Si).

In another particular embodiment, the compound of Formula (Ia) can be 1,3,5-trimethyl-1,3,5-triethoxy-1,3,5-trisilacyclohexane ([EtOCH$_3$SiCH$_2$]$_3$), the trivalent metal oxide source can be aluminum tri-sec-butoxide, and the compound of Formula (Va) can be tetraethyl orthosilicate (TEOS) ((EtO)$_4$Si).

In another particular embodiment, $R^3$ can be ethyl, $R^4$ and $R^5$ can be ethoxy and $R^6$ can be

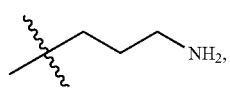 [SMILES: *CCCN]

such that the compound corresponding to Formula (Va) can be (3-aminopropyl)triethoxysilane (H$_2$N(CH$_2$)$_3$(EtO)$_3$Si).

In another particular embodiment, the compound of Formula (Ia) can be 1,1,3,3,5,5-hexaethoxy-1,3,5-trisilacyclohexane ([(EtO)$_2$SiCH$_2$]$_3$), the trivalent metal oxide source can be aluminum tri-sec-butoxide, and the compound of Formula (Va) can be (3-aminopropyl)triethoxysilane (H$_2$N(CH$_2$)$_3$(EtO)$_3$Si).

In another particular embodiment, $R^3$ can be methyl, $R^4$ and $R^5$ can be methoxy and $R^4$ can be

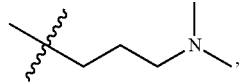 [SMILES: *CCCN(C)C]

such that the compound corresponding to Formula (Va) can be (N,N-dimethylaminopropyl)trimethoxysilane (((CH$_3$)$_2$N(CH$_2$)$_3$)(MeO)$_3$Si).

In another particular embodiment, the compound of Formula (Ia) can be 1,1,3,3,5,5-hexaethoxy-1,3,5-trisilacyclohexane ([(EtO)$_2$SiCH$_2$]$_3$), the trivalent metal oxide source can be aluminum tri-sec-butoxide, and the compound of Formula (Va) can be (N,N-dimethylaminopropyl)trimethoxysilane (((CH$_3$)$_2$N(CH$_2$)$_3$)(MeO)$_3$Si).

In another particular embodiment. $R^3$ can be ethyl, $R^4$ and $R^5$ can be ethoxy and $R^6$ can be

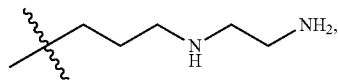 [SMILES: *CCCNCCN]

such that the compound corresponding to Formula (Va) can be (N-(2-aminoethyl)-3-aminopropyltriethoxysilane ((H$_2$N(CH$_2$)$_2$NH (CH$_2$)$_3$)(EtO)$_2$Si).

In another particular embodiment, the compound of Formula (Ia) can be 1,1,3,3,5,5-hexaethoxy-1,3,5-trisilacyclohexane ([(EtO)$_2$SiCH$_2$]$_3$), the trivalent metal oxide source can be aluminum tri-sec-butoxide, and the compound of Formula (Va) can be (N-(2-aminoethyl)-3-aminopropyltriethoxysilane ((H$_2$N(CH$_2$)$_2$NH(CH$_2$)$_3$)(EtO)$_2$Si).

In another particular embodiment, $R^3$ can be ethyl, $R^4$ and $R^5$ can be ethoxy and $R^6$ can be

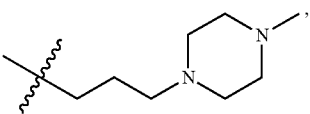 [SMILES: *CCCN1CCN(C)CC1]

such that the compound corresponding to Formula (Va) can be 4-methyl-1-(3-triethoxysilylpropyl)-piperazine.

In another particular embodiment, the compound of Formula (Ia) can be 1,1,3,3,5,5-hexaethoxy-1,3,5-trisilacyclohexane ($[(EtO)_2SiCH_2]_3$), the trivalent metal oxide source can be aluminum tri-sec-butoxide, and the compound of Formula (Va) can be 4-methyl-1-(3-triethoxysilylpropyl)-piperazine.

In another particular embodiment, $R^3$ can be ethyl, $R^4$ and $R^5$ can be ethoxy and $R^6$ can be

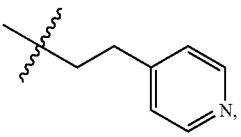 [SMILES: *CCc1ccncc1]

such that the compound corresponding to Formula (Va) can be 4-(2-(triethoxysily)ethyl)pyridine.

In another particular embodiment, the compound of Formula (Ia) can be 1,1,3,3,5,5-hexaethoxy-1,3,5-trisilacyclohexane ($[(EtO)_2SiCH_2]_3$), the trivalent metal oxide source can be aluminum tri-sec-butoxide, and the compound of Formula (Va) can be 4-(2-(triethoxysily)ethyl)pyridine.

In another particular embodiment, $R^3$ can be ethyl, $R^4$ and $R^5$ can be ethoxy and $R^5$ can be

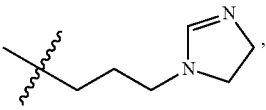 [SMILES: *CCCN1C=NCC1]

such that the compound corresponding to Formula (Va) can be 1-(3-(triethoxysilyl)propyl)-4,5-dihydro-1H-imidazole.

In another particular embodiment, the compound of Formula (Ia) can be 1,1,3,3,5,5-hexaethoxy-1,3,5-trisilacyclohexane ($[(EtO)_2SiCH_2]_3$), the trivalent metal oxide source can be aluminum tri-sec-butoxide, and the compound of Formula (Va) can be 1-(3-(triethoxysilyl)propyl)-4,5-dihydro-1H-imidazole.

The molar ratio of compound of Formula (Ia) to compound of Formula (Va) may vary within wide limits, such as from about 99:1 to about 1:99, from about 1:5 to about 5:1, from about 4:1 to about 1:4 or from about 3:2 to about 2:3. For example, a molar ratio of compound of Formula (Ia) to compound of Formula (Va) can be from about 4:1 to 1:4 or from about 2.5:1 to about 1:2.5, about 2:1 to about 1:2, such as about 1.5:1 to about 1.5:1.

III.D. Compounds of Formula (VIa)

In additional embodiments, the methods provided herein can further comprise adding to the aqueous solution a compound of Formula $Z^{18}Z^{19}Z^{20}Si-R^7Si\ Z^{18}Z^{19}Z^{20}$ (VIa) to obtain an organosilica material which is a copolymer comprising at least one independent unit Formula (I) as described herein, at least one other trivalent metal oxide monomer (e.g., at least one independent unit of Formula (II) and/or Formula (III)) as described herein, optionally at least one independent unit of Formula (IV) as described herein, optionally at least one independent unit of Formula (V) described herein and at least one independent unit of Formula (III) as described herein, wherein each $Z^{18}$ independently can be a $C_1$-$C_4$ alkoxy group; each $Z^{19}$ and $Z^{20}$ independently can be a $C_1$-$C_4$ alkoxy group or a $C_1$-$C_4$ alkyl group; and each $R^7$ can be selected from the group consisting a $C_1$-$C_8$ alkylene group, a $C_2$-$C_8$ alkenylene group, a $C_2$-$C_8$ alkynylene group, a nitrogen-containing $C_2$-$C_{10}$ alkylene group, an optionally substituted $C_6$-$C_{20}$ aralkyl group, and an optionally substituted $C_4$-$C_{20}$ heterocycloalkyl group.

In one embodiment, each $Z^{18}$ can be a $C_1$-$C_3$ alkoxy group, a $C_1$-$C_2$ alkoxy group, or methoxy.

Additionally or alternatively, each $Z^{19}$ and $Z^{20}$ each independently can be a $C_1$-$C_3$ alkoxy group, a $C_1$-$C_2$ alkoxy group, or methoxy.

Additionally or alternatively, each $Z^{18}$ can be a $C_1$-$C_2$ alkoxy group and each $Z^{19}$ and $Z^{20}$ independently can be a $C_1$-$C_2$ alkoxy group.

Additionally or alternatively, $Z^{19}$ and $Z^{20}$ each independently can be a $C_1$-$C_3$ alkyl group, a $C_1$-$C_2$ alkyl group, or methyl.

Additionally or alternatively, each $Z^{18}$ can be a $C_1$-$C_2$ alkoxy group and each $Z^{19}$ and $Z^{20}$ independently can be a $C_1$-$C_2$ alkyl group.

Additionally or alternatively, each $Z^{18}$ can be a $C_1$-$C_2$ alkoxy group and each $Z^{19}$ and $Z^{20}$ independently can be a $C_1$-$C_2$ alkoxy group or a $C_1$-$C_2$ alkyl group.

Additionally or alternatively, each $R^7$ can be a $C_1$-$C_7$ alkylene group, a $C_1$-$C_6$ alkylene group, a $C_1$-$C_5$ alkylene group, a $C_1$-$C_4$ alkylene group, a $C_1$-$C_3$ alkylene group, a $C_1$-$C_2$ alkylene group, or —$CH_2$—.

Additionally or alternatively, each $Z^{18}$ can be a $C_1$-$C_2$ alkoxy group; each $Z^{19}$ and $Z^{20}$ independently can be a $C_1$-$C_2$ alkoxy group or a $C_1$-$C_2$ alkyl group; and each $R^7$ can be a $C_1$-$C_2$ alkylene group.

Additionally or alternatively, each $R^7$ can be a $C_2$-$C_7$ alkenylene group, a $C_1$-$C_6$ alkenylene group, a $C_2$-$C_5$ alkenylene group, a $C_2$-$C_4$ a alkenylene group, a $C_2$-$C_3$ alkenylene group, or —CH=CH—.

Additionally or alternatively, each $Z^{18}$ can be a $C_1$-$C_2$ alkoxy group; each $Z^{19}$ and $Z^{20}$ independently can be a $C_1$-$C_2$ alkoxy group or a $C_1$-$C_2$ alkyl group; and $R^7$ can be a $C_1$-$C_2$ alkenylene group.

Additionally or alternatively, each $Z^{18}$ can be a $C_1$-$C_2$ alkoxy group; each $Z^{19}$ and $Z^{20}$ independently can be a $C_1$-$C_2$ alkoxy group or a $C_1$-$C_2$ alkyl group; and $R^7$ can be a $C_1$-$C_2$ alkylene group or a $C_1$-$C_2$ alkenylene group.

Additionally or alternatively, each $R^7$ can be a $C_2$-$C_7$ alkynylene group, a $C_1$-$C_6$ alkynylene group, a $C_2$-$C_5$ alkynylene group, a $C_2$-$C_4$ a alkynylene group, a $C_2$-$C_3$ alkynylene group, or —C≡C—.

Additionally or alternatively, each $Z^{18}$ can be a $C_1$-$C_2$ alkoxy group; each $Z^{19}$ and $Z^{20}$ independently can be a $C_1$-$C_2$ alkoxy group or a $C_1$-$C_2$ alkyl group; and each $R^7$ can be a $C_2$-$C_4$ alkynylene group.

Additionally or alternatively, each $Z^{18}$ can be a $C_1$-$C_2$ alkoxy group; each $Z^{19}$ and $Z^{20}$ independently can be a $C_1$-$C_2$ alkoxy group or a $C_1$-$C_2$ alkyl group; and each $R^7$ can be a $C_2$-$C_4$ alkylene group, a $C_2$-$C_4$ alkenylene group or a $C_2$-$C_4$ alkynylene group.

Additionally or alternatively, each $R^7$ can be a nitrogen-containing $C_2$-$C_{10}$ alkylene group, a nitrogen-containing $C_3$-$C_{10}$ alkylene group, a nitrogen-containing $C_4$-$C_{10}$ alkylene group, a nitrogen-containing $C_4$-$C_9$ alkylene group, a nitrogen-containing $C_4$-$C_8$ alkylene group, or nitrogen containing $C_3$-$C_8$ alkylene group. The aforementioned nitrogen-containing alkylene groups may have one or more nitrogen atoms (e.g., 2, 3, etc.). Examples of nitrogen-containing alkylene groups include, but are not limited to,

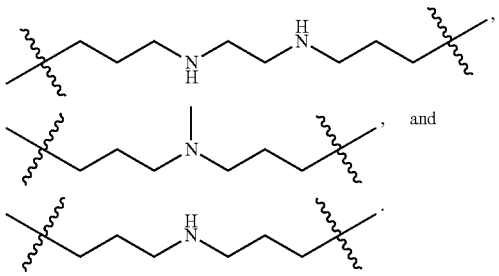

Additionally or alternatively, each $Z^{18}$ can be a $C_1$-$C_2$ alkoxy group; each $Z^{19}$ and $Z^{20}$ independently can be a $C_1$-$C_2$ alkoxy group or a $C_1$-$C_2$ alkyl group; and $R^7$ can be a nitrogen-containing $C_4$-$C_{10}$ alkylene group.

Additionally or alternatively, each $Z^{18}$ can be a $C_1$-$C_2$ alkoxy group; each $Z^{19}$ and $Z^{20}$ independently can be a $C_1$-$C_2$ alkoxy group or a $C_1$-$C_2$ alkyl group; and $R^7$ can be a $C_2$-$C_4$ alkylene group, a $C_2$-$C_4$ alkenylene group, a $C_2$-$C_4$ alkynylene group or a nitrogen-containing $C_4$-$C_{10}$ alkylene group.

Additionally or alternatively, each $R^7$ can be an optionally substituted $C_6$-$C_{20}$ aralkyl, an optionally substituted $C_6$-$C_{14}$ aralkyl, or an optionally substituted $C_6$-$C_{10}$ aralkyl. Examples of $C_6$-$C_{20}$ aralkyls include, but are not limited to, phenylmethyl, phenylethyl, and naphthylmethyl. The aralkyl may be optionally substituted with a $C_1$-$C_6$ alkyl group, particularly a $C_1$-$C_4$ alkyl group.

Additionally or alternatively, each $Z^{18}$ can be a $C_1$-$C_2$ alkoxy group; each $Z^{19}$ and $Z^{20}$ independently can be a $C_1$-$C_2$ alkoxy group or a $C_1$-$C_2$ alkyl group; and each $R^7$ can be an optionally substituted $C_6$-$C_{10}$ aralkyl.

Additionally or alternatively, each $Z^{18}$ can be a $C_1$-$C_2$ alkoxy group; $Z^{19}$ and $Z^{20}$ ea each $Z^{19}$ and $Z^{20}$ ch independently can be a $C_1$-$C_2$ alkoxy group or a $C_1$-$C_2$ alkyl group; and each $R^7$ can be a $C_2$-$C_4$ alkylene group, a $C_2$-$C_4$ alkenylene group, a $C_2$-$C_4$ alkynylene group, or an optionally substituted $C_6$-$C_{10}$ aralkyl.

Additionally or alternatively, each $R^7$ can be an optionally substituted $C_4$-$C_{20}$ heterocycloalkyl group, an optionally substituted $C_4$-$C_{16}$ heterocycloalkyl group, an optionally substituted $C_4$-$C_{12}$ heterocycloalkyl group, or an optionally substituted $C_4$-$C_{10}$ heterocycloalkyl group. Examples of $C_4$-$C_{20}$ heterocycloalkyl groups include, but are not limited to, thienylmethyl, furylethyl, pyrrolylmethyl, piperazinylethyl, pyridylmethyl, benzoxazolylethyl, quinolinylpropyl, and imidazolylpropyl. The heterocycloalkyl may be optionally substituted with a $C_1$-$C_6$ alkyl group, particularly a $C_1$-$C_4$ alkyl group.

Additionally or alternatively, each $Z^{18}$ can be a $C_1$-$C_2$ alkoxy group; each $Z^{19}$ and $Z^{20}$ independently can be a $C_1$-$C_2$ alkoxy group or a $C_1$-$C_2$ alkyl group; and each $R^7$ can be an optionally substituted $C_4$-$C_{12}$ heterocycloalkyl group.

Additionally or alternatively, each $Z^{18}$ can be a $C_1$-$C_2$ alkoxy group; each $Z^{19}$ and $Z^{20}$ independently can be a $C_1$-$C_2$ alkoxy group or a $C_1$-$C_2$ alkyl group; and each $R^7$ can be a $C_2$-$C_4$ alkylene group, a $C_2$-$C_4$ alkenylene group, a $C_2$-$C_4$ alkynylene group, an optionally substituted $C_6$-$C_{10}$ aralkyl, or an optionally substituted $C_4$-$C_{12}$ heterocycloalkyl group.

In a particular embodiment, each $Z^{18}$ and $Z^{19}$ can be ethoxy, each $Z^{20}$ can be methyl and $R^7$ can be —$CH_2CH_2$—, such that compound corresponding to Formula (VIa) can be 1,2-bis(methyldiethoxysilyl)ethane ($CH_3(EtO)_2Si$—$CH_2$—$CH_2$—$Si(EtO)_2CH_3$).

In another particular embodiment, Formula (Ia) can be 1,1,3,3,5,5-hexaethoxy-1,3,5-trisilacyclohexane ($[(EtO)_2SiCH_2]_3$), the trivalent metal oxide source can be aluminum tri-sec-butoxide, and Formula (VIa) can be 1,2-bis(methyldiethoxysilyl)ethane ($CH_3(EtO)_2Si$—$CH_2CH_2$—$Si(EtO)_2CH_3$).

In another particular embodiment, each $Z^{18}$, $Z^{19}$ and $Z^{20}$ can be ethoxy and $R^7$ can be —$CH_2$—, such that compound corresponding to Formula (VIa) can be bis(triethoxysilyl)methane (($EtO)_3Si$—$CH_2$—$Si(EtO)_3$).

In another particular embodiment, the compound of Formula (Ia) can be 1,1,3,3,5,5-hexaethoxy-1,3,5-trisilacyclohexane ($[(EtO)_2SiCH_2]_3$), the trivalent metal oxide source can be aluminum tri-sec-butoxide, and the compound of Formula (VIa) can be bis(triethoxysilyl)methane (($EtO)_3Si$—$CH_2$—$Si(EtO)_3$).

In another particular embodiment, each $Z^{18}$, $Z^{19}$ and $Z^{20}$ can be ethoxy and $R^7$ can be —HC=CH—, such that compound corresponding to Formula (VIa) can be 1,2-bis(triethoxysilyl)ethylene (($EtO)_3Si$—HC=CH—$Si(EtO)_3$).

In another particular embodiment, the compound of Formula (Ia) can be 1,1,3,3,5,5-hexaethoxy-1,3,5-trisilacyclohexane ($[(EtO)_2SiCH_2]_3$)), the trivalent metal oxide source can be aluminum tri-sec-butoxide, and the compound of Formula (VIa) can be 1,2-bis(triethoxysilyl)ethylene (($EtO)_3Si$—HC=CH—$Si(EtO)_3$).

In another particular embodiment, the compound of Formula (VIa) can be bis(triethoxysilyl)methane (($EtO)_3Si$—$CH_2$—$Si(EtO)_3$), the trivalent metal oxide source can be aluminum tri-sec-butoxide, and the compound of Formula (Va) can be tetraethyl orthosilicate (TEOS) (($EtO)_4Si$).

In a particular embodiment, each $Z^{18}$, $Z^{19}$ and $Z^{20}$ can be methoxy and $R^7$ can be

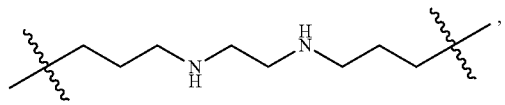 [SMILES: *CCCNCCNCCC*]

such that compound corresponding to Formula (VIa) can be N,N'-bis[(3-trimethoxysilyl)propyl]ethylenediamine.

In another particular embodiment, the compound of Formula (Ia) can be 1,1,3,3,5,5-hexaethoxy-1,3,5-trisilacyclohexane ($[(EtO)_2SiCH_2]_3$), the trivalent metal oxide source can be aluminum tri-sec-butoxide, and the compound of Formula (VIa) can be N,N'-bis[(3-trimethoxysilyl)propyl]ethylenediamine.

In another particular embodiment, each $Z^{18}$ and $Z^{19}$ can be ethoxy, each $Z^{20}$ can be methyl and $R^7$ can be

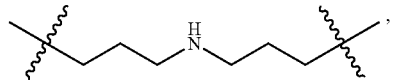 [SMILES: *CCCNCCC*]

such that compound corresponding to Formula (VIa) can be bis[(methyldiethoxysilyl)propyl]amine.

In another particular embodiment, the compound of Formula (Ia) can be 1,1,3,3,5,5-hexaethoxy-1,3,5-trisilacyclohexane ($[(EtO)_2SiCH_2]_3$), the trivalent metal oxide source can be aluminum tri-sec-butoxide, and the compound of Formula (VIa) can be bis[(methyldiethoxysilyl)propyl]amine.

In another particular embodiment, each $Z^{18}$ and $Z^{19}$ can be methoxy, each $Z^{20}$ can be methyl and $R^7$ can be

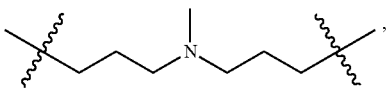 [SMILES: *CCCN(C)CCC*]

such that compound corresponding to Formula (VIa) can be bis[(methyldimethoxysilyl)propyl]-N-methylamine.

In another particular embodiment, the compound of Formula (Ia) can be 1,1,3,3,5,5-hexaethoxy-1,3,5-trisilacyclohexane ([(EtO)$_2$SiCH$_2$]$_3$), the trivalent metal oxide source can be aluminum tri-sec-butoxide, and the compound of Formula (VIa) can be bis[(methyldimethoxysilyl)propyl]-N-methylamine.

The molar ratio of compound of Formula (Ia) to compound of Formula (VIa) may vary within wide limits, such as from about 99:1 to about 1:99, from about 1:5 to about 5:1, from about 4:1 to about 1:4 or from about 3:2 to about 2:3. For example, a molar ratio of compound of Formula (Ia) to compound of Formula (VIa) can be from about 4:1 to 1:4 or from about 2.5:1 to 1:2.5, about 2:1 to about 1:2, such as about 1.5:1 to about 1.5:1.

III.C. Metal Chelate Sources

In additional embodiments, the methods provided herein can further comprise adding to the aqueous solution a source of metal chelate compounds.

Examples of metal chelate compounds, when present, can include titanium chelate compounds such as triethoxy.mono (acetylacetonato) titanium, tri-n-propoxy.mono(acetylacetonato)titanium, tri-i-propoxy.mono(acetylacetonato)titanium, tri-n-butoxy.mono(acetylacetonato)titanium, tri-sec-butoxy.mono(acetylacetonato)titanium, tri-t-butoxy.mono(acetylacetonato)titanium, diethoxy.bis(acetylacetonato)titanium, di-n-propoxy.bis(acetylacetonato)titanium, di-i-propoxy.bis(acetylacetonato)titanium, di-n-butoxy.bis(acetylacetonato) titanium, di-sec-butoxy.bis(acetylacetonato)titanium, di-t-butoxy.bis(acetylacetonato)titanium, monoethoxy.tris(acetylacetonato)titanium, mono-n-propoxy.tris(acetylacetonato) titanium, mono-i-propoxy.tris(acetylacetonato)titanium, m0ono-n-butoxy. tris(acetylacetonato)titanium, mono-sec-butoxy.tris(acetylacetonato)titanium, mono-t-butoxy-tris(acetylacetonato)titanium, tetrakis(acetylacetonato)titanium, triethoxy. mono(ethylacetoacetaato)titanium, tri-n-propoxy.mono(ethylacetoacetato)titanium, tri-i-propoxy.mono(ethylacetoacetato) titanium, tri-n-butoxy.mono(ethylacetoacetato) titanium, tri-sec-butoxy.mono(ethylacetoacetato) titanium, tri-t-butoxy-mono(ethylacetoacetato)titanium, diethoxy.bis(ethylacetoacetato)titanium, di-n-propoxy.bis(ethylacetoacetato)titanium, di-i-propoxy.bis(ethylacetoacetato)titanium, di-n-butoxy.bis(ethylacetoacetato)titanium, di-sec-butoxy.bis(ethylacetoacetato)titanium, di-t-butoxy.bis(ethylacetoacetato)titanium, monoethoxy.tris(ethylacetoacetato) titanium, mono-n-propoxy.tris(ethylacetoaetato)titanium, mono-i-propoxy.tris(ethylacetoacetato) titanium, mono-n-butoxy.tris(ethylacetoacetato)titanium, mono-sec-butoxy.tris(ethylacetoacetato)titanium, mono-t-butoxy.tris(ethylacetoacetato)titanium, tetrakis(ethylacetoacetato)titanium, mono(acetylacetonato)tris(ethylacetoacetato) titanium, bis(acetylacetonato)bis(ethylacetoacetato)titanium, and tris(acetylacetonato)mono(ethylacetoacetato)titanium; zirconium chelate compounds such as triethoxy.mono(acetylacetonato)zirconium, tri-n-propoxy.mono(acetylacetonato) zirconium, tri-i-propoxy.mono(acetylacetonato)zirconium, tri-n-butoxy. mono(acetylacetonato)zirconium, tri-sec-butoxy.mono(acetylacetonato)zirconium, tri-t-butoxy.mono(acetylacetonato)zirconium, diethoxy.bis(acetylacetonato)zirconium, di-n-propoxy.bis(acetylacetonato)zirconium, di-i-propoxy.bis(acetylacetonato)zirconium, di-n-butoxy.bis(acetylacetonato)zirconium, di-sec-butoxy.bis(acetylacetonato)zirconium, di-t-butoxy.bis(acetylacetonato)zirconium, monoethoxy.tris(acetylacetonato)zirconium, mono-n-propoxy.tris(acetylacetonato)zirconium, mono-i-propoxy.tris(acetylacetonato) zirconium, mono-n-butoxy.tris(acetylacetonato)zirconium, mono-sec-butoxy. tris(acetylacetonato)zirconium, mono-t-butoxy.tris(acetylacetonato)zirconium, tetrakis(acetylacetonato)zirconium, triethoxy.mono (ethylacetoacetato)zirconium, tri-n-propoxy.mono(ethylacetoacetato)zirconium, tri-i-propoxy.mono(ethylacetoacetato) zirconium, tri-n-butoxy.mono(ethylacetoacetato)zirconium, tri-sec-butoxy. mono(ethylacetoacetato)zirconium, tri-t-butoxy.mono(ethylacetoacetato)zirconium, diethoxy.bis(ethylacetoacetato)zirconium, di-n-propoxy.bis(ethylacetoacetato)zirconium, di-i-propoxy.bis(ethylacetoacetato) zirconium, di-n-butoxy.bis(ethylacetoacetato) zirconium, di-sec-butoxy.bis(ethylacetoacetato)zirconium, di-t-butoxy.bis(ethylacetoacetato)zirconium, monoethoxy.tris(ethylacetoacetato)zirconium, mono-n-propoxy.tris(ethylacetoacetato)zirconium, mono-i-propoxy.tris(ethylacetoacetato) zirconium, mono-n-butoxy.tris(ethylacetoacetato)zirconium, mono-sec-butoxy. tris(ethylacetoacetato)zirconium, mono-t-butoxy.tris(ethylacetoacetato)zirconium, tetrakis(ethylacetoacetato)zirconium, mono(acetylacetonato)tris(ethylacetoacetato) zirconium, bis(acetylacetonato)bis(ethylacetoacetato)zirconium, and tris(acetylacetonato)mono(ethylacetoacetato)zirconium; and aluminum chelate compounds such as tris(acetylacetonato)aluminum and tris(ethylacetoacetato)aluminum. Of these, the chelate compounds of titanium or aluminum can be of note, of which the chelate compounds of titanium can be particularly of note. These metal chelate compounds may be used either singly or in combination III.D. Molar Ratio In the methods described herein, a molar ratio of Formula (Ia): Formula (IIa), Formula (Ia): Formula (IIIa) of about 99:1 to about 1:99, about 75:1 to about 1:99, about 50:1 to about 1:99, about 25:1 to about 1:99, about 15:1 to about 1:99, about 50:1 to about 1:50, about 25:1 to about 1:25 or about 15:1 to about 1:15 may be used. For example, molar ratios of about 3:2, about 4:1, about 4:3, about 5:1, about 2:3, about 1:1 about 5:2 and about 15:1 may be used. For example, a molar ratio of Formula (Ia):Formula (IIa), Formula (Ia):Formula (IIIa) of about 15:1 and about 5:1 can be used.

For the sake of the following discussion, the compounds of Formula (Ia), (Va) and (VIa) shall be referred to collectively as starting siloxane. Depending on the choice of starting materials, the solution may have a variety of compositions. For example, if base is used, the solution may have molar ratios of starting siloxane to OH$^-$ of from about 1:5 to about 1:20, such as from about 1:5 to about 1:15 or from about 1:5 to 1:10, or from about 1:6 to 1:20. If acid is used, the solution may have molar ratios of starting siloxane:H$^+$ of from about 50:1 to about 5:1, such as from about 45:1 to about 10:1. In both cases when acid or base is used, the molar ratios of starting siloxane to H$_2$O may vary from about 1:50 to about 1:1000, such as from about 1:100 to about 1:500.

III.E. Aging the Solution

The solution formed in the methods described herein can be aged for at least about 4 hours, at least about 6 hours, at least about 12 hours, at least about 18 hours, at least about 24 hours (1 day), at least about 30 hours, at least about 36 hours, at least about 42 hours, at least about 48 hours (2 days), at least about 54 hours, at least about 60 hours, at least about 66 hours, at least about 72 hours (3 days), at least about 96 hours (4 days), at least about 120 hours (5 days) or at least about 144 hours (6 days).

Additionally or alternatively, the solution formed in the methods described herein can be aged for about 4 hours to about 144 hours (6 days), about 4 hours to about 120 hours (5 days), about 4 hours to about 96 hours (4 days), about 4 hours to about 72 hours (3 days), about 4 hours to about 66 hours, about 4 hours to about 60 hours, about 4 hours to about 54 hours, about 4 hours to about 48 hours (2 days), about 4 hours to about 42 hours, about 4 hours to about 36 hours, about 4 hours to about 30 hours, about 4 hours to about 24 hours (1 day), about 4 hours to about 18 hours, about 4 hours to about 12 hours, about 4 hours to about 6 hours, about 6 hours to about 144 hours (6 days), about 6 hours to about 120 hours (5 days), about 6 hours to about 96 hours (4 days), about 6 hours to about 72 hours (3 days), about 6 hours to about 66 hours, about 6 hours to about 60 hours, about 6 hours to about 54 hours, about 6 hours to about 48 hours (2 days), about 6 hours to about 42 hours, about 6 hours to about 36 hours, about 6 hours to about 30 hours, about 6 hours to about 24 hours (1 day), about 6 hours to about 18 hours, about 6 hours to about 12 hours, about 12 hours to about 144 hours (6 days), about 12 hours to about 120 hours (5 days), about 12 hours to about 96 hours (4 days), about 12 hours to about 72 hours (3 days), about 12 hours to about 66 hours, about 12 hours to about 60 hours, about 12 hours to about 54 hours, about 12 hours to about 48 hours (2 days), about 12 hours to about 42 hours, about 12 hours to about 36 hours, about 12 hours to about 30 hours, about 12 hours to about 24 hours (1 day), about 12 hours to about 18 hours, about 18 hours to about 144 hours (6 days), about 18 hours to about 120 hours (5 days), about 18 hours to about 96 hours (4 days), about 18 hours to about 72 hours (3 days), about 18 hours to about 66 hours, about 18 hours to about 60 hours, about 18 hours to about 54 hours, about 18 hours to about 48 hours (2 days), about 18 hours to about 42 hours, about 18 hours to about 36 hours, about 18 hours to about 30 hours, about 18 hours to about 24 hours (1 day), about 24 hours (1 day) to about 144 hours (6 days), about 24 (1 day) hours (1 day) to about 120 hours (5 days), about 24 hours (1 day) to about 96 hours (4 days), about 24 hours (1 day) to about 72 hours (3 days), about 24 hours (1 day) to about 66 hours, about 24 hours (1 day) to about 60 hours, about 24 hours (1 day) to about 54 hours, about 24 hours (1 day) to about 48 hours (2 days), about 24 hours (1 day) to about 42 hours, about 24 hours (1 day) to about 36 hours, about 24 hours (1 day) to about 30 hours, about 30 hours to about 144 hours (6 days), about 30 hours to about 120 hours (5 days), about 30 hours to about 96 hours (4 days), about 30 hours to about 72 hours (3 days), about 30 hours to about 66 hours, about 30 hours to about 60 hours, about 30 hours to about 54 hours, about 30 hours to about 48 hours (2 days), about 30 hours to about 42 hours, about 30 hours to about 36 hours, about 36 hours to about 144 hours (6 days), about 36 hours to about 120 hours (5 days), about 36 hours to about 96 hours (4 days), about 36 hours to about 72 hours (3 days), about 36 hours to about 66 hours, about 36 hours to about 60 hours, about 36 hours to about 54 hours, about 36 hours to about 48 hours (2 days), about 36 hours to about 42 hours, about 42 hours to about 144 hours (6 days), about 42 hours to about 120 hours (5 days), about 42 hours to about 96 hours (4 days), about 42 hours to about 72 hours (3 days), about 42 hours to about 66 hours, about 42 hours to about 60 hours, about 42 hours to about 54 hours, about 42 hours to about 48 hours (2 days), about 48 hours (2 days) to about 144 hours (6 days), about 48 hours (2 days) to about 120 hours (5 days), about 48 hours (2 days) to about 96 hours (4 days), about 48 hours (2 days) to about 72 hours (3 days), about 48 hours (2 days) to about 66 hours, about 48 hours (2 days) to about 60 hours, about 48 hours (2 days) to about 54 hours, about 54 hours to about 144 hours (6 days), about 54 hours to about 120 hours (5 days), about 54 hours to about 96 hours (4 days), about 54 hours to about 72 hours (3 days), about 54 hours to about 66 hours, about 54 hours to about 60 hours, about 60 hours to about 144 hours (6 days), about 60 hours to about 120 hours (5 days), about 60 hours to about 96 hours (4 days), about 60 hours to about 72 hours (3 days), about 60 hours to about 66 hours, about 66 hours to about 144 hours (6 days), about 66 hours to about 120 hours (5 days), about 66 hours to about 96 hours (4 days), about 66 hours to about 72 hours (3 days), about 72 hours (3 days) to about 144 hours (6 days), about 72 hours (3 days) to about 120 hours (5 days), about 72 hours (3 days) to about 96 hours (4 days), about 96 hours (4 days) to about 144 hours (6 days), about 96 hours (4 days) to about 120 hours (5 days), or about 120 hours (5 days) to about 144 hours (6 days).

Additionally or alternatively, the solution formed in the method can be aged at temperature of at least about 10° C., at least about 20° C., at least about 30° C., at least about 40° C., at least about 50° C., at least about 60° C., at least about 70° C., at least about 80° C., at least about 90° C., at least about 100° C., at least about 110° C., at least about 120° C. at least about 130° C., at least about 140° C., at least about 150° C., at least about 175° C., at least about 200° C., at least about 250° C., or about 300° C.

Additionally or alternatively, the solution formed in the method can be aged at temperature of about 10° C. to about 300° C., about 10° C. to about 250° C., about 10° C. to about 200° C., about 10° C. to about 175° C., about 10° C. to about 150° C., about 10° C. to about 140° C., about 10° C. to about 130° C., about 10° C. to about 120° C., about 10° C. to about 110° C., about 10° C. to about 100° C., about 10° C. to about 90° C., about 10° C. to about 80° C., about 10° C. to about 70° C., about 10° C. to about 60° C., about 10° C. to about 50° C., about 20° C. to about 300° C., about 20° C. to about 250° C., about 20° C. to about 200° C., about 20° C. to about 175° C., about 20° C. to about 150° C., about 20° C. to about 140° C., about 20° C. to about 130° C., about 20° C. to about 120° C., about 20° C. to about 110° C., about 20° C. to about 100° C., about 20° C. to about 90° C., about 20° C. to about 80° C., about 20° C. to about 70° C., about 20° C. to about 60° C., about 20° C. to about 50° C., about 30° C. to about 300° C., about 30° C. to about 250° C., about 30° C. to about 200° C., about 30° C. to about 175° C., about 30° C. to about 150° C., about 30° C. to about 140° C., about 30° C. to about 130° C., about 30° C. to about 120° C., about 30° C. to about 110° C., about 30° C. to about 100° C., about 30° C. to about 90° C., about 30° C. to about 80° C., about 30° C. to about 70° C., about 30° C. to about 60° C., about 30° C. to about 50° C., about 50° C. to about 300° C., about 50° C. to about 250° C., about 50° C. to about 200° C., about 50° C. to about 175° C., about 50° C. to about 150° C., about 50° C. to about 140° C., about 50° C. to about 130° C., about 50° C. to about 120° C., about 50° C. to about 110° C., about 50° C. to about 100° C., about 50° C. to about 90° C., about 50° C. to about 80° C., about 50° C. to about 70° C., about 50° C. to about 60° C., about 70° C. to about 300° C., about 70° C. to about 250° C., about 70° C. to about 200° C., about 70° C. to about 175° C., about 70° C. to about 150° C., about 70° C. to about 140° C., about 70° C. to about 130° C., about 70° C. to about 120° C., about 70° C. to about 110° C., about 70° C. to about 100° C., about 70° C. to about 90° C., about 70° C. to about 80° C., about 80° C. to about 300° C., about 80° C. to about 250° C., about 80° C. to about 200° C., about 80° C. to about 175° C., about 80° C. to about 150° C., about 80° C. to about 140° C., about 80° C. to about 130° C., about 80° C. to about 120° C., about 80° C. to about 110° C., about 80° C. to about 100° C., about 80° C. to about 90° C., about 90° C. to about 300° C., about 90° C. to about 250° C., about 90° C. to about 200° C., about 90° C. to about 175° C., about 90° C. to about 150° C., about 90° C. to about 140° C., about 90° C. to about 130° C., about 90° C. to about 120° C., about 90° C. to about 110° C., about 90° C. to about 100° C., about 100° C. to about 300° C., about 100° C. to about 250° C., about 100° C. to about 200° C., about 100° C. to about 175° C., about 100° C. to about 150° C., about 100° C. to about 140° C., about 100° C. to about 130° C., about 100° C. to about 120° C., about 100° C. to about 110° C., about 110° C. to about 300° C., about 110° C. to about 250° C., about 110° C. to about 200° C., about 110° C. to about 175° C., about 110° C. to about 150° C., about 110° C. to about 140° C., about 110° C. to about 130° C., about 110° C. to about 120° C., about 120° C. to about 300° C., about 120° C. to about 250° C., about 120° C. to about 200° C., about 120° C. to about 175° C., about 120° C. to about 150° C., about 120° C. to about 140° C., about 120° C. to about 130° C., about 130° C. to about 300° C., about 130° C. to about 250° C., about 130° C. to about 200° C., about 130° C. to about 175° C., about 130° C. to about 150° C., or about 130° C. to about 140° C.

III.I. Drying the Pre-Product

The methods described herein comprise drying the pre-product (e.g., a gel) to produce an organosilica material.

In some embodiments, the pre-product (e.g., a gel) formed in the method can be dried at a temperature of greater than or equal to about 50° C., greater than or equal to about 70° C., greater than or equal to about 80° C., greater than or equal to about 100° C., greater than or equal to about 110° C., greater than or equal to about 120° C., greater than or equal to about 150° C., greater than or equal to about 200° C., greater than or equal to about 250° C., greater than or equal to about 300° C., greater than or equal to about 350° C., greater than or equal to about 400° C., greater than or equal to about 450° C., greater than or equal to about 500° C., greater than or equal to about 550° C., or greater than or equal to about 600° C.

Additionally or alternatively, the pre-product (e.g., a gel) formed in the method can be dried at temperature of about 50° C. to about 600° C., about 50° C. to about 550° C., about 50° C. to about 500° C., about 50° C. to about 450° C., about 50° C. to about 400° C., about 50° C. to about 350° C., about 50° C. to about 300° C., about 50° C. to about 250° C., about 50° C. to about 200° C., about 50° C. to about 150° C., about 50° C. to about 120° C., about 50° C. to about 110° C., about 50° C. to about 100° C., about 50° C. to about 80° C., about 50° C. to about 70° C., about 70° C. to about 600° C., about 70° C. to about 550° C., about 70° C. to about 500° C., about 70° C. to about 450° C., about 70° C. to about 400° C., about 70° C. to about 350° C., about 70° C. to about 300° C., about 70° C. to about 250° C., about 70° C. to about 200° C., about 70° C. to about 150° C., about 70° C. to about 120° C., about 70° C. to about 110° C., about 70° C. to about 100° C., about 70° C. to about 80° C., about 80° C. to about 600° C., about 80° C. to about 550° C., about 80° C. to about 500° C., about 80° C. to about 450° C., about 80° C. to about 400° C., about 80° C. to about 350° C., about 80° C. to about 300° C., about 80° C. to about 250° C., about 80° C. to about 200° C., about 80° C. to about 150° C., about 80° C. to about 120° C., about 80° C. to about 110° C., or about 80° C. to about 100° C.

In a particular embodiment, the pre-product (e.g., a gel) formed in the method can be dried at temperature from about 70° C. to about 200° C.

Additionally or alternatively, the pre-product (e.g., a gel) formed in the method can be dried in a $N_2$ and/or air atmosphere.

III.K. Optional Further Steps

In some embodiments, the method can further comprise calcining the organosilica material to obtain a silica material. The calcining can be performed in air or an inert gas, such as nitrogen or air enriched in nitrogen. Calcining can take place at a temperature of at least about 300° C., at least about 350° C., at least about 400° C., at least about 450° C., at least about 500° C., at least about 550° C., at least about 600° C., or at least about 650° C., for example at least about 400° C. Additionally or alternatively, calcining can be performed at a temperature of about 300° C. to about 650° C., about 300° C. to about 600° C., about 300° C. to about 550° C., about 300° C. to about 400° C., about 300° C. to about 450° C., about 300° C. to about 400° C., about 300° C. to about 350° C., about 350° C. to about 650° C., about 350° C. to about 600° C., about 350° C. to about 550° C., about 350° C. to about 400° C., about 350° C. to about 450° C., about 350° C. to about 400° C., about 400° C. to about 650° C., about 400° C. to about 600° C., about 400° C. to about 550° C., about 400° C. to about 500° C., about 400° C. to about 450° C., about 450° C. to about 650° C., about 450° C. to about 600° C., about 450° C. to about 550° C., about 450° C. to about 500° C., about 500° C. to about 650° C., about 500° C. to about 600° C., about 500° C. to about 550° C., about 550° C. to about 650° C., about 550° C. to about 600° C. or about 600° C. to about 650° C.

IV. Organosilica Material Product-by-Process

Organosilica materials can be made from the methods described herein. In another particular embodiment, organosilica materials made from an aqueous mixture as described herein that contains essentially no structure directing agent or porogen as described herein, wherein the organosilica material may be:

(i) a copolymer of:
 (a) at least one independent unit of Formula (I) as described herein:
 (b) at least one independent unit of Formula (II) as described herein and/or at least one independent unit of Formula (III) as described herein; and
 (c) optionally, at least one independent unit of Formulas (IV) as described herein, at least one independent unit of Formula (V) as described herein, and/or at least one independent unit of Formula (VI) as described herein.

The organosilica materials made from the methods described herein may exhibit an XRD pattern as described herein, particularly with only one peak between about 1 and about 3 degrees 2θ. Additionally or alternatively, the organosilica materials made from the methods described herein can exhibit substantially no peaks in the range of about 0.5 to about 10 degrees 2θ, about 0.5 to about 12 degrees 2θ range, about 0.5 to about 15 degrees 2θ, about 0.5 to about 20 degrees 2θ, about 0.5 to about 30 degrees 2θ, about 0.5 to about 40 degrees 2θ, about 0.5 to about 50 degrees 2θ, about 0.5 to about 60 degrees 2θ, about 0.5 to about 70 degrees 2θ, about 2 to about 10 degrees 2θ, about 2 to about 12 degrees 2θ range, about 2 to about 15 degrees 2θ, about 2 to about 20 degrees 2θ, about 2 to about 30 degrees 2θ, about 2 to about 40 degrees 2θ, about 2 to about 50 degrees 2θ, about 2 to about 60 degrees 2θ, about 2 to about 70 degrees 2θ, about 3 to about 10 degrees 2θ, about 3 to about 12 degrees 2θ range, about 3 to about 15 degrees 2θ, about 3 to about 20 degrees 2θ, about 3 to about 30 degrees 2θ, about 3 to about 40 degrees 2θ, about 3 to about 50 degrees 2θ, about 3 to about 60 degrees 2θ, or about 3 to about 70 degrees 2θ.

Additionally or alternatively, the organosilica materials may have an average pore diameter as described herein, particularly, between about 1.5 nm and about 20.0 nm.

V. Uses of the Organosilica Materials

The organosilica materials described herein find uses in several areas.

In certain embodiments, the organosilica material described herein can be used as adsorbents or support matrices for separation and/or catalysis processes.

V.A. Gas Separation Processes

In some cases, the organosilica materials can be used in a gas separation process as provided herein. The gas separation process can comprise contacting a gas mixture containing at least one contaminant with the organosilica material described herein as prepared according to the methods described herein.

In various embodiments, the gas separation process can be achieved by swing adsorption processes, such as pressure swing adsorption (PSA) and temperature swing adsorption (TSA). All swing adsorption processes typically have an adsorption step in which a feed mixture (typically in the gas phase) is flowed over an adsorbent to preferentially adsorb a more readily adsorbed component relative to a less readily adsorbed component. A component may be more readily adsorbed because of kinetic or equilibrium properties of the adsorbent. The adsorbent can typically be contained in a contactor that is part of the swing adsorption unit. The contactor can typically contain an engineered structured adsorbent bed or a particulate adsorbent bed. The bed can contain the adsorbent and other materials such as other adsorbents, mesopore filling materials, and/or inert materials used to mitigated temperature excursions from the heat of adsorption and desorption. Other components in the swing adsorption unit can include, but are not necessarily limited to, valves, piping, tanks, and other contactors. Swing adsorption processes are described in detail in U.S. Pat. Nos. 8,784,533; 8,784,534; 8,858,683; and 8,784,535, each of which are incorporated herein by reference. Examples of processes that can be used herein either separately or in combination are PSA, TSA, pressure temperature swing adsorption (PTSA), partial purge displacement swing adsorption (PPSA), PPTSA, rapid cycle PSA (RCPSA), RCTSA, RCPPSA and RCPTSA.

Swing adsorption processes can be applied to remove a variety of target gases, also referred to as "contaminant gas" from a wide variety of gas mixtures. Typically, in binary separation systems, the "light component" as utilized herein is taken to be the species or molecular component(s) not preferentially taken up by the adsorbent in the adsorption step of the process. Conversely in such binary systems, the "heavy component" as utilized herein is typically taken to be the species or molecular component(s) preferentially taken up by the adsorbent in the adsorption step of the process. However, in binary separation systems where the component(s) that is(are) preferentially adsorbed has(have) a lower molecular weight than the component(s) that is(are) not preferentially adsorbed, those descriptions may not necessarily correlate as disclosed above.

An example of gas mixture that can be separated in the methods described herein is a gas mixture comprising $CH_4$, such as a natural gas stream. A gas mixture comprising $CH_4$ can contain significant levels of contaminants such as $H_2O$, $H_2S$, $CO_2$, $N_2$, mercaptans, and/or heavy hydrocarbons. Additionally or alternatively, the gas mixture can comprise $NO_x$ and/or $SO_x$ species as contaminants, such as a waste gas stream, a flue gas stream and a wet gas stream. As used herein, the terms "$NO_x$," and "$NO_x$" species refers to the various oxides of nitrogen that may be present in waste gas, such as waste gas from combustion processes. The terms refer to all of the various oxides of nitrogen including, but not limited to, nitric oxide (NO), nitrogen dioxide ($NO_2$), nitrogen peroxide ($N_2O$), nitrogen pentoxide ($N_2O_5$), and mixtures thereof. As used herein, the terms "$SO_x$," and "$SO_x$ species," refers to the various oxides of sulfur that may be present in waste gas, such as waste gas from combustion processes. The terms refer to all of the various oxides of sulfur including, but not limited to, SO, $SO_2$, $SO_3$, $SO_4$, $S_7O_2$ and $S_6O_2$. Thus, examples of contaminants include, but are not limited to $H_2O$, $H_2S$, $CO_2$, $N_2$, mercaptans, heavy hydrocarbons, $NO_x$ and/or $SO_x$ species.

V.B. Aromatic Hydrogenation Process

The hydrogenation catalyst can further comprise a binder such as, but not limited to, active and inactive materials, inorganic materials, clays, ceramics, activated carbon, alumina, silica, silica-alumina, titania, zirconia, niobium oxide, tantalum oxide, or a combination thereof, particularly, silica-alumina, alumina, titania, or zirconia. These hydrogenation catalysts can be used for both hydrogenation and aromatic saturation of a feedstream.

In various embodiments, the hydrogenation process can be achieved by contacting a hydrocarbon feedstream comprising aromatics with a hydrogenation catalyst described herein in the presence of a hydrogen-containing treat gas in a first reaction stage operated under effective aromatics hydrogenation conditions to produce a reaction product with reduced aromatics content.

Hydrogen-containing treat gasses suitable for use in a hydrogenation process can be comprised of substantially pure hydrogen or can be mixtures of other components typically found in refinery hydrogen streams. It is preferred that the hydrogen-containing treat gas stream contains little, more preferably no, hydrogen sulfide. The hydrogen-containing treat gas purity should be at least about 50% by volume hydrogen, preferably at least about 75% by volume hydrogen, and more preferably at least about 90% by volume hydrogen for best results. It is most preferred that the hydrogen-containing stream be substantially pure hydrogen.

Feedstreams suitable for hydrogenation by the hydrogenation catalyst described herein include any conventional hydrocarbon feedstreams where hydrogenation or aromatic saturation is desirable. Typically, an input feed for an aromatic saturation process can be generated as a product or side-product from a previous type of hydroprocessing, such as hydrocracking for fuels or lubricant base stock production. A wide range of petroleum and chemical feedstocks can be hydroprocessed. Such feedstreams can include hydrocarbon fluids, diesel, kerosene, lubricating oil feedstreams, heavy coker gasoil (HKGO), de-asphalted oil (DAO), FCC main column bottom (MCB), steam cracker tar. Such feedstreams can also include other distillate feedstreams such as light to heavy distillates including raw virgin distillates, wax-containing feedstreams such as feeds derived from crude oils, shale oils and tar sands. Synthetic feeds such as those derived from the Fischer-Tropsch process can also be aromatically saturated using the hydrogenation catalyst described herein. Typical wax-containing feedstocks for the preparation of lubricating base oils have initial boiling points of about 315° C. or higher, and include feeds such as whole and reduced petroleum crudes, hydrocrackates, raffinates, hydrotreated oils, gas oils (such as atmospheric gas oils, vacuum gas oils, and coker gas oils), atmospheric and vacuum residues, deasphalted oils/residua (e.g., propane deasphalted residua, brightstock, cycle oil), dewaxed oils, slack waxes and Fischer-Tropsch wax, and mixtures of these materials. Such feeds may be derived from distillation towers (atmospheric and vacuum), hydrocrackers, hydrotreaters and solvent extraction units, and may have wax contents of up to 50% or more. Preferred lubricating oil boiling range feedstreams include feedstreams which boil in the range of 650-1100° F. Diesel boiling range feedstreams include feedstreams which boil in the range of 480-660° F. Kerosene boiling range feedstreams include feedstreams which boil in the range of 350-617° F.

Hydrocarbon feedstreams suitable for use herein also contain aromatics and nitrogen- and sulfur-contaminants. Feedstreams containing up to 0.2 wt. % of nitrogen, based on the feedstream, up to 3.0 wt. % of sulfur, and up to 50 wt. % aromatics can be used in the present process In various embodiments, the sulfur content of the feedstreams can be below about 500 wppm, or below about 300 wppm, or below about 200 wppm, or below about 100 wppm, or below about 50 wppm, or below about 15 wppm. The pressure used during an aromatic hydrogenation process can be modified based on the expected sulfur content in a feedstream. Feeds having a high wax content typically have high viscosity indexes of up to 200 or more. Sulfur and nitrogen contents may be measured by standard ASTM methods D2622 (sulfur), and D5453 and/or D4629 (nitrogen), respectively.

Effective hydrogenation conditions may be considered to be those conditions under which at least a portion of the aromatics present in the hydrocarbon feedstream are saturated, preferably at least about 50 wt. % of the aromatics are saturated, more preferably greater than about 75 wt. %. Effective hydrogenation conditions can include temperatures of from 150° C. to 400° C., a hydrogen partial pressure of from 740 to 20786 kPa (100 to 3000 psig), a space velocity of from 0.1 to 10 liquid hourly space velocity (LHSV), and a hydrogen to feed ratio of from 89 to 1780 $m^3/m^3$ (500 to 10000 scf/B).

Additionally or alternatively, effective hydrogenation conditions may be conditions effective at removing at least a portion of the nitrogen and organically bound sulfur contaminants and hydrogenating at least a portion of said aromatics, thus producing at least a liquid lube boiling range product having a lower concentration of aromatics and nitrogen and organically bound sulfur contaminants than the lube boiling range feedstream.

Additionally or alternatively, effective hydrogenation conditions may be conditions effective at removing at least a portion of the nitrogen and organically bound sulfur contaminants and hydrogenating at least a portion of said aromatics, thus producing at least a liquid diesel boiling range product having a lower concentration of aromatics and nitrogen and organically bound sulfur contaminants than the diesel boiling range feedstream.

As stated above, in some instances, the hydrocarbon feedstream (e.g., lube oil boiling range) may be hydrotreated to reduce the sulfur contaminants to below about 500 wppm, particularly below about 300 wppm, particularly below about 200 wppm or particularly below about 100 wppm. In such an embodiment, the process may comprise at least two reaction stages, the first reaction state containing a hydrotreating catalyst operated under effective hydrotreating conditions, and the second containing a hydrogenation catalyst has described herein operated under effective hydrogenation conditions as described above. Therefore, in such an embodiment, the hydrocarbon feedstream can be first contacted with a hydrotreating catalyst in the presence of a hydrogen-containing treat gas in a first reaction stage operated under effective hydrotreating conditions in order to reduce the sulfur content of the feedstream to within the above-described range. Thus, the term "hydrotreating" as used herein refers to processes wherein a hydrogen-containing treat gas is used in the presence of a suitable catalyst that is active for the removal of heteroatoms, such as sulfur, and nitrogen. Suitable hydrotreating catalysts for use in the present invention are any conventional hydrotreating catalyst and includes those which are comprised of at least one Group 8 metal, preferably Fe, Co and Ni, more preferably Co and/or Ni, and most preferably Ni; and at least one Group 6 metal, preferably Mo and W, more preferably Mo, on a high surface area support material, preferably alumina. Additionally or alternatively, more than one type of hydrotreating catalyst can be used in the same reaction vessel. The Group 8 metal may typically be present in an amount ranging from about 2 to 20 wt. %, preferably from about 4 to 12 wt. %. The Group 6 metal can typically be present in an amount ranging from about 5 to 50 wt. %, preferably from about 10 to 40 wt. %, and more preferably from about 20 to 30 wt. %. All metals weight percents are "on support" as described above.

Effective hydrotreating conditions may be considered to be those conditions that can effectively reduce the sulfur content of the feedstream (e.g., lube oil boiling range) to within the above-described ranges. Typical effective hydrotreating conditions can include temperatures ranging from about 150° C. to about 425° C., preferably about 200° C. to about 370° C., more preferably about 230° C. to about 350° C. Typical weight hourly space velocities ("WHSV") may range from about 0.1 to about 20 $hr^{-1}$, preferably from about 0.5 to about 5 $hr^{-1}$. Any effective pressure can be utilized, and pressures can typically range from about 4 to about 70 atmospheres (405 to 7093 kPa), preferably 10 to 40 atmospheres (1013 to 4053 kPa). In a particular embodiment, said effective hydrotreating conditions may be conditions effective at removing at least a portion of said organically bound sulfur contaminants and hydrogenating at least a portion of said aromatics, thus producing at least a reaction product (e.g., liquid lube oil boiling range product) having a lower concentration of aromatics and organically bound sulfur contaminants than the lube oil boiling range feedstream.

The contacting of the hydrocarbon feedstream with the hydrotreating catalyst may produce a reaction product comprising at least a vapor product and a liquid product. The vapor product may typically comprise gaseous reaction products, such as $H_2S$, and the liquid reaction product may typically comprise a liquid hydrocarbon having a reduced level of nitrogen and sulfur contaminants. The total reaction product can be passed directly into the second reaction stage, but it may be preferred that the gaseous and liquid reaction products be separated, and the liquid reaction product conducted to the second reaction stage. Thus, in one embodiment, the vapor product and the liquid product may be separated, and the liquid product may be conducted to the second reaction stage. The method of separating the vapor product from the liquid product can be accomplished by any means known to be effective at separating gaseous and liquid reaction products. For example, a stripping tower or reaction zone can be used to separate the vapor product from the liquid product (e.g., liquid lube oil boiling range product). The liquid product thus conducted to the second reaction stage can have a sulfur concentration within the range of about 500 wppm, particularly below about 300 wppm, or particularly below about 200 wppm or particularly below about 100 wppm.

In still other embodiments, the hydrogenation catalysts described herein can be used in integrated hydroprocessing methods. In addition to the hydrofinishing and/or aromatic hydrogenation/saturation processes involving the hydrogenation catalyst described herein, an integrated hydroprocessing method can also include various combinations of hydrotreating, hydrocracking, catalytic dewaxing (such as hydrodewaxing), and/or solvent dewaxing. The scheme of hydrotreating followed by hydrofinishing described above represents one type of integrated process flow. Another integrated processing example is to have a dewaxing step, either catalytic dewaxing or solvent dewaxing, followed by hydroprocessing with the hydrogenation catalysts described herein. Still another example is a process scheme involving hydrotreating, dewaxing (catalytic or solvent), and then hydroprocessing with the hydrogenation catalysts described herein. Yet another example is hydroprocessing with the hydrogenation catalysts described herein followed by dewaxing (catalytic or solvent). Alternatively, multiple hydrofinishing and/or aromatic hydrogenation steps can be employed with hydrotreatment, hydrocracking, or dewaxing steps. An example of such a process flow is hydrofinishing, dewaxing (catalytic or solvent), and then hydrofinishing again, where at least one of the hydrofinishing steps may use a hydrogenation catalysts described herein. For processes involving catalytic dewaxing, effective catalytic dewaxing conditions can include temperatures of from 150° C. to 400° C., preferably 250° C. to 350° C., pressures of from 791 to 20786 kPa (100 to 3000 psig), preferably 1480 to 17338 kPa (200 to 2500 psig), liquid hourly space velocities of from 0.1 to 10 hr$^{-1}$, preferably 0.1 to 5 hr$^{-1}$ and hydrogen treat gas rates from 45 to 1780 m$^3$/m$^3$ (250 to 10000 scf/B), preferably 89 to 890 m$^3$/m$^3$ (500 to 5000 scf/B). Any suitable dewaxing catalyst may be used.

In embodiments where the product of an aromatic saturation process will be a lubricant base oil, the input feed should also have suitable lubricant base oil properties. For example, an input feed intended for use as a Group I or Group II base oil can have a viscosity index (VI) of at least about 80, preferably at least about 90 or at least about 95. An input feed intended for use as a Group I+ base oil can have a VI of at least about 100, while an input feed intended for use as a Group II+ base oil can have a VI of at least 110. The viscosity of the input feed can be at least 2 cSt at 100° C., or at least 4 cSt at 100° C., or at least 6 cSt at 100° C.

VI. Further Embodiments

The invention can additionally or alternately include one or more of the following embodiments.

Embodiment 1. An organosilica material, which is a polymer of at least one independent monomer of Formula [$Z^1OZ^2OSiCH_2$]$_3$ (I), wherein each $Z^1$ and $Z^2$ independently represent a hydrogen atom, a $C_1$-$C_4$ alkyl group or a bond to a silicon atom of another monomer and at least one other trivalent metal oxide monomer.

Embodiment 2. The organosilica material of embodiment 1, wherein each $Z^1$ and $Z^2$ independently represent a hydrogen atom, a $C_1$-$C_2$ alkyl group or a bond to a silicon atom of another monomer.

Embodiment 3. The organosilica material of embodiment 1 or 2, wherein each $Z^1$ and $Z^2$ independently represent a hydrogen atom, ethyl or a bond to a silicon atom of another monomer.

Embodiment 4. The mesoporous organosilica material of any one of the previous embodiments wherein the at least one other trivalent metal oxide monomer is
(i) an independent unit of formula $M^1(OZ^3)_3$ (II), wherein $M^1$ represents a Group 13 metal and each $Z^3$ independently represents a hydrogen atom, a $C_1$-$C_6$ alkyl or a bond to a silicon atom of another monomer; or
(ii) an independent unit of formula $(Z^4O)_2M^2$-O—Si$(OZ^5)_3$ (III), wherein $M^2$ represents a Group 13 metal and each $Z^4$ and each $Z^5$ independently represent a hydrogen atom, a $C_1$-$C_6$ alkyl group or a bond to a silicon atom of another monomer.

Embodiment 5. The organosilica material of embodiment 4, wherein at least one unit of formula (II) is present, wherein $M^1$ is Al or B and each $Z^3$ independently represents a hydrogen atom, a $C_1$-$C_4$ alkyl group or a bond to a silicon atom or another monomer.

Embodiment 6. The organosilica material of embodiment 4 or 5, wherein at least one unit of formula (III) is present, wherein $M^2$ is Al or B; and each $Z^4$ and each $Z^5$ each independently represent a hydrogen atom, a $C_1$-$C_4$ alkyl group or a bond to a silicon atom of another monomer.

Embodiment 7. The organosilica material of any one of the previous embodiments further comprising a monomer selected from the group consisting of:
(i) an independent unit of formula [$Z^6OZ^7SiCH_2$]$_3$ (IV), wherein each $Z^6$ represents a hydrogen atom, a $C_1$-$C_4$ alkyl group or a bond to a silicon atom of another monomer and each $Z^7$ represents a hydroxyl group, a $C_1$-$C_6$ alkyl group or an oxygen atom bonded to a silicon atom of another monomer;
(ii) an independent unit of formula $Z^8OZ^9Z^{10}Z^{11}Si$ (V), wherein each $Z^8$ represents a hydrogen atom or a $C_1$-$C_4$ alkyl group or a bond to a silicon atom of another monomer; and $Z^9$, $Z^{10}$ and $Z^{11}$ are each independently selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroaralkyl group, a nitrogen-containing optionally substituted heterocycloalkyl group, and an oxygen atom bonded to a silicon atom of another monomer; and
(iii) an independent unit of formula $Z^{12}Z^{13}Z^{14}Si$—R—Si$Z^{12}Z^{13}Z^{14}$ (VI), wherein each $Z^{12}$ independently represents a hydroxyl group, a $C_1$-$C_4$ alkoxy group or an oxygen atom bonded to a silicon atom of another comonomer; each $Z^{13}$ and $Z^{14}$ independently represent a hydroxyl group, a $C_1$-$C_4$ alkoxy group, a $C_1$-$C_4$ alkyl group or an oxygen bonded to a silicon atom of another monomer; and R is selected from the group consisting of a $C_1$-$C_8$ alkylene group, a $C_2$-$C_8$ alkenylene group, a $C_2$-$C_8$ alkynylene group, a nitrogen-containing $C_2$-$C_{10}$ alkylene group, an optionally substituted $C_6$-$C_{20}$ aralkyl and an optionally substituted $C_4$-$C_{20}$ heterocycloalkyl group; and
(iv) a combination thereof.

Embodiment 8. The organosilica material of any one of the previous embodiments, wherein the organosilica has an average pore diameter between about 1.5 nm and about 20.0 nm.

Embodiment 9. The organosilica material of any one of the previous embodiments, wherein the organosilica material has a total surface area of about 200 m²/g to about 2500 m²/g.

Embodiment 10. The organosilica material of any one of the previous embodiments, wherein the organosilica material has a pore volume about 0.1 cm³/g to about 5.0 cm³/g.

Embodiment 11. The organosilica material of any one of the previous embodiments, further comprising at least one catalytic metal incorporated within the pores of the material.

Embodiment 12. The organosilica material of embodiment 11, wherein the catalytic metal is selected from the group consisting of a Group 6 element, a Group 8 element, a Group 9 element, a Group 10 element and a combination thereof.

Embodiment 13. The organosilica material of any one of the previous embodiments made using essentially no structure directing agent or porogen.

EXAMPLES

General Methods

Small Angle X-Ray Diffraction Analysis

X-ray powder diffraction (XRD) patterns were collected on a PANalytical X'pert diffractometer equipped with an accessory for low angle measurements. XRD analyses were recorded using the Cu Ka (=1.5405980 Å) line in the 2θ range from 0.5 to 10° with a step size of 0.0167° and a counting time of 1.2 s.

Solid-State (SS) NMR Measurements

The $^{29}$Si MAS NMR spectra were recorded on a Varian InfinityPlus-400 spectrometer (operating at 9.4T) and Varian InfinityPlus-500 (operating at 11.74T), corresponding to $^{29}$Si Larmor frequencies of 79.4 MHz and 99.2 MHz, respectively, with a 7.5 mm MAS probe heads using 5 kHz spinning, 4.0 μs 90° pulses, and at least 60 s recycle delay, with proton decoupling during data acquisition. The $^{29}$Si chemical shifts are referenced with respect to an external tetramethyl silane ($\delta_{Si}$=0.0 ppm). The $^{13}$C CPMAS NMR spectra were recorded on a Varian InfinityPlus-500 spectrometer corresponding to $^{13}$C Larmor frequency of 125 MHz, with 1.6 mm MAS probe head using 40 kHz spinning, $^1$H-$^{13}$C cross-polarization (CP) contact time of at least 1 ms, a recycle delay of at least 1 s, with proton decoupling during data acquisition. The $^{13}$C chemical shifts are referenced with respect to an external tetramethyl silane ($\delta_C$=0.0 ppm). The $^{27}$Al MAS NMR spectra were recorded on a Varian InfinityPlus-500 corresponding to $^{27}$Al Larmor frequency of 130.1 MHz using a 4 mm MAS probe head using 12 kHz spinning, with a π/12 radian pulse length, with proton decoupling during data acquisition, and a recycle delay of 0.3 s. The chemical shifts are referenced with respect to an external solution of Al(H$_2$O)$_6^{3+}$ ($\delta_{Al}$=0.0 ppm). All NMR spectra were recorded at room temperature using air for spinning.

Thermal Gravimetric Analysis (TGA)

Thermal stability results were recorded on Q5000 TGA. Ramp rate was 5° C./min; temperature range was from 25° C. to 800° C. All the samples were tested in both air and nitrogen.

CO$_2$ Adsorption

The work was done with a Quantchrom autosorb iQ2. All the samples were pre-treated at 120° C. in vacuum for 3 hours before collecting the CO$_2$ isotherm at different temperatures.

Nitrogen Porosimetry

The nitrogen adsorption/desorption analyses was performed with different instruments, e.g. TriStar 3000, TriStar II 3020 and Autosorb-1. All the samples were pre-treated at 120° C. in vacuum for 4 hours before collecting the N$_2$ isotherm. The analysis program calculated the experimental data and report BET surface area (total surface area), microporous surface area (S), total pore volume, pore volume for micropores, average pore diameter (or radius), etc.

Surface Acidity Analysis

Alpha Testing

For the Alpha activity test, about 70 mg of sample were sized to 14-25 mesh size and loaded in a plug flow reactor. Samples were heated to 1000° F. (about 538° C.) in a flow of 100 ml/min He at a ramp rate of about 40° F. (about 4.4° C.)/min. The sample was then exposed to a flow of about 100 Torr hexane in He at atmospheric pressure. The gas flow rate was adjusted to maintain a hexane conversion between 5 and 25%. Four measurements were taken at 4, 11, 18, and 25 minutes. Product analysis was done by GC/FID. The Alpha value reported is the activity at 18 minutes time on stream.

Alpha is a measure for the n-hexane cracking activity of a catalyst or sample. It is defined as the ratio of the first order rate constant for n-hexane cracking relative to a silica-alumina standard, and determined using the formula below $$\alpha = A*\ln(1-X)/\tau$$

where:

α is the relative first order rate constant;

A is equal to −1.043 and includes the reference rate constant & unit conversion;

X is the fractional conversion;

τ is the residence time defined using the formula τ=wt/(ρ*F);

where ρ is the assumed packing density and is equal to 0.55 g/cm³;

F is the gas flow rate (helium+hexane+½ cracked products) cm³/min; and wt is the catalyst weight in grams.

TPAA/TPAD Method

The ammonia adsorption and temperature-programmed desorption was measured gravimetrically using a Mettler SDTA851 TGA instrument. Before the ammonia adsorption, the samples were calcined in air at 500° C. for 1 hr (ramp rate 20° C./min) in order to remove any adsorbed moisture or volatile compound. The sample was subsequently cooled to 250° C. in helium, and exposed to a flow of helium at 250° C. for 5 min and 20 seconds. Recurrent pulses of 1% NH$_3$/He were then dosed into the system at 250° C. while monitoring the sample weight in-situ using a microbalance. After saturation of the acid sites with NH$_3$, the system was purged with helium at 250° C. for 5 min and 20 seconds in order to remove physically adsorbed ammonia. The catalyst temperature was subsequently ramped from 250° C. to 700° C. in 1% NH$_3$/He at a rate of 5° C./min to carry out the temperature programmed ammonia desorption.

Collidine Uptake

The collidine uptake was measured gravimetrically on a TA Q5000 TGA micro balance. The catalyst sample was dried in nitrogen flow at 200° C. for 60 minutes in order to remove physisorbed water. Subsequently the sample was exposed to a flow of collidine in N$_2$ for 60 minutes at a collidine vapor pressure of 3 Torr. After collidine adsorption, the sample was treated in flowing nitrogen for 60 minutes at 200° C. prior to measuring the weight uptake of collidine. The dried catalyst weight and the final weight after exposure and subsequent stripping of collidine were used to calculate the collidine uptake.

IR-Pyridine Test Protocol

For the IR measurement of adsorbed pyridine, the samples were ground in an agate mortar and pressed into thin self-supporting wafers. Specific wafer weights ranged from 10 to 22 mg/cm². Four square wafers of 7 mm×7 mm size were placed into a Multi-Sample-IR-Transmission cell (MSTIR) equipped with $CaF_2$ windows. Samples were pretreated in-situ by evacuation for 2 hr at 300° C. at a pressure of $6\times10^{-7}$ Torr. The samples were subsequently exposed for 30 min to about 16 Torr equilibrium vapor pressure of pyridine at 150° C. followed by evacuation for 30 min at 150° C. at a pressure of about $10^{-6}$ Torr. For the collection of IR spectra the MSTIR cuvette was transferred into a Nicolet 670 FTIR spectrometer. Spectra were taken at 2 $cm^{-1}$ resolution accumulating 512 scans. The bands at 1545 $cm^{-1}$ and 1450 $cm^{-1}$ were chosen to assess the presence of Brønsted and Lewis acid sites, respectively.

Example 1

Organosilica Material Syntheses Using Formula [$R^1R^2SiCH_2$]₃ (Ia) in Basic or Acidic Media 1A. Synthesis Using [(EtO)₂SiCH₂]₃ in Basic Aqueous Medium—without Surfactant.

A solution with 18.6 g of 30% NH₄OH and 23.76 g deionized water (DI) water was made. The pH of the solution was 12.55. To the solution, 3.0 g of 1,1,3,3,5,5-hexaethoxy-1,3,5-trisilacyclohexane ([(EtO)₂SiCH₂]₃) was added, producing a mixture having the molar composition:

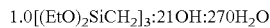

1.0[(EtO)₂SiCH₂]₃:21OH:270H₂O and stirred for 1 day at room temperature (20-25° C.). The solution was transferred to an autoclave and aged at 80° C.-90° C. for 1 day to produce a gel. The gel was dried at 80° C. in a vacuum to remove most of the water and then fully dried at 110° C. for three hours. This produced Sample 1A as a clear solid, which was converted to white powder after grinding. No surface directing agent or porogen were used in this preparation.

The procedure was repeated with the following molar composition

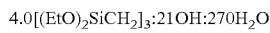

4.0[(EtO)₂SiCH₂]₃:21OH:270H₂O to produce Sample 1B.

XRD Analysis

XRD was performed on Sample 1A. The XRD pattern of Sample 1A is shown in FIG. 1.

TGA Analysis

Figure 2A:
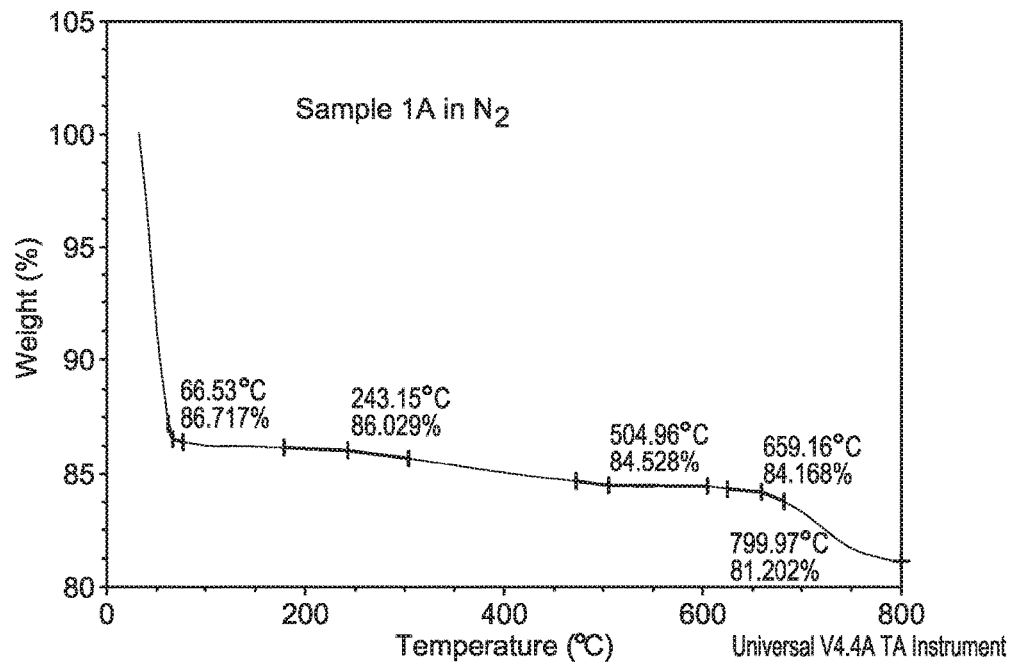
FIG. 2a illustrates thermal gravimetric analysis (TGA) data for Sample 1A in $N_2$.
Figure 2B:
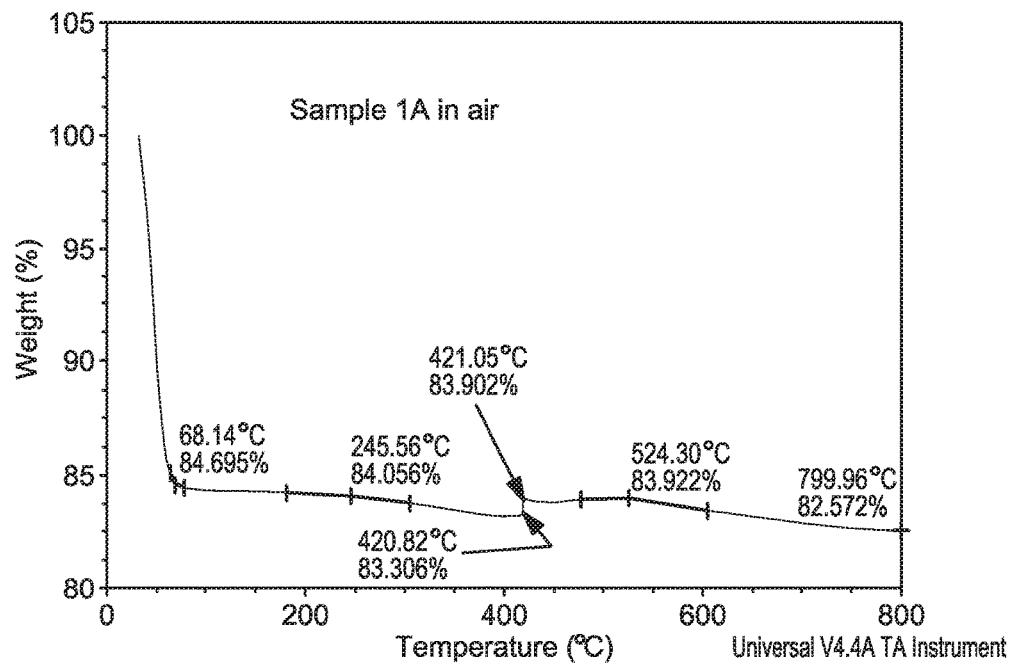
FIG. 2b illustrates TGA data for Sample 1A in air.
Figure 3:
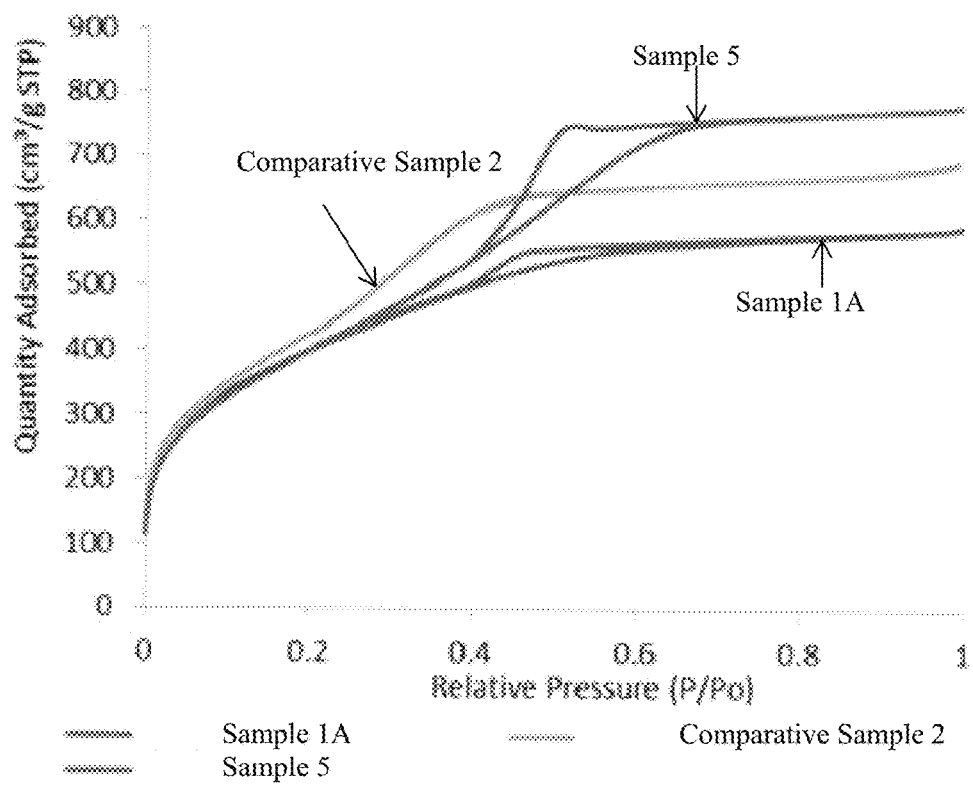
FIG. 3 illustrates BET $N_2$ adsorption for Sample 1A, Comparative Sample 2 and Sample 5.
Figure 4:
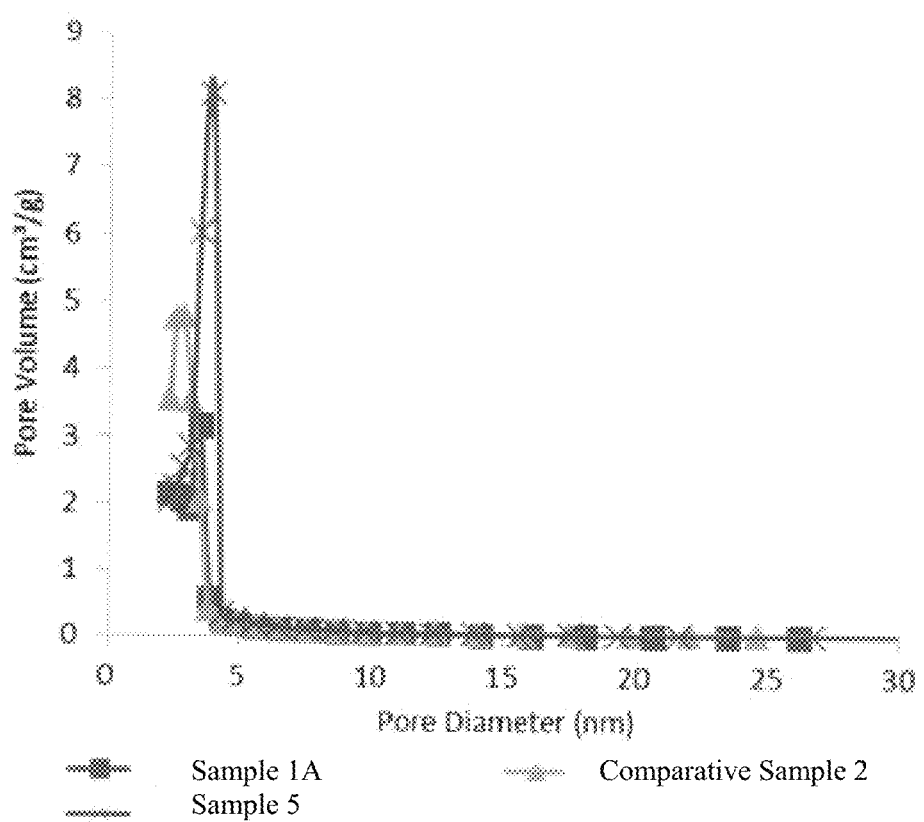
FIG. 4 illustrates a BET pore diameter distribution for Sample 1A, Comparative Sample 2 and Sample 5.

TGA weight loss studies were performed on Sample 1A in nitrogen and air. FIGS. 2a and 2b display the TGA data for Sample 1A in nitrogen and air, respectively.

Nitrogen Adsorption/Desorption Analysis

Nitrogen adsorption/desorption analysis was performed on Sample 1A, and the results are provided in Table 1 below and FIGS. 3-6.

SS-NMR-Analysis

Figure 7A:
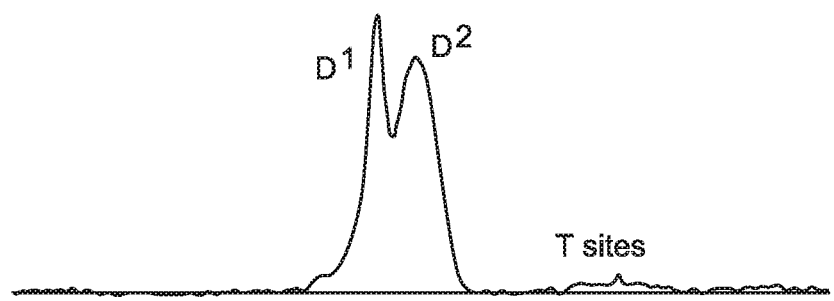
FIG. 7a illustrates a $^{29}$Si MAS NMR spectrum for Sample 1A.

Sample 1A was characterized with ²⁹Si MAS NMR with the results as shown in FIG. 7a.

1B. Comparative—Synthesis Using [(EtO)₂SiCH₂]₃ in Basic Aqueous Medium—with Surfactant.

In this example, an organosilica material was prepared according to Landskron, K., et al., Science 302:266-269 (2003).

Cetyltrimethylammonium bromide (CTMABr, 0.9 mmol, 0.32 g, Aldrich) was dissolved in a mixture of 2.16 g NH₄OH (35 wt %) and 3.96 g de-ionized water at 20° C. to form a solution.

[(EtO)₂SiCH₂]₃ (1.26 mmol, 0.5 g) was added to the solution, producing a solution having the molar composition:

1.0[(EtO)₂SiCH₂]₃:17OH:236H₂O:0.7CTMABr which was stirred for 1 day at 20° C. and a white precipitate formed. Afterwards, the solution was aged for 1 day at 80° C. Then the precipitate was filtered off and washed with water. The sample was then stirred for 48 hours in a solution of 12 g HCl (36 wt %) and 80 g of methanol. The sample was then filtered off again and washed with MeOH, resulting in Comparative Sample 2.

XRD Analysis

XRD was performed Comparative Sample 2. A comparison of the XRD patterns for Sample A1 and Comparative Sample 2 is shown in FIG. 1. Compared to the XRD pattern of Sample 1A, the XRD pattern of Comparative Sample 2 exhibits a shoulder at about 3 degrees 2θ.

TGA Analysis

Figure 8A:
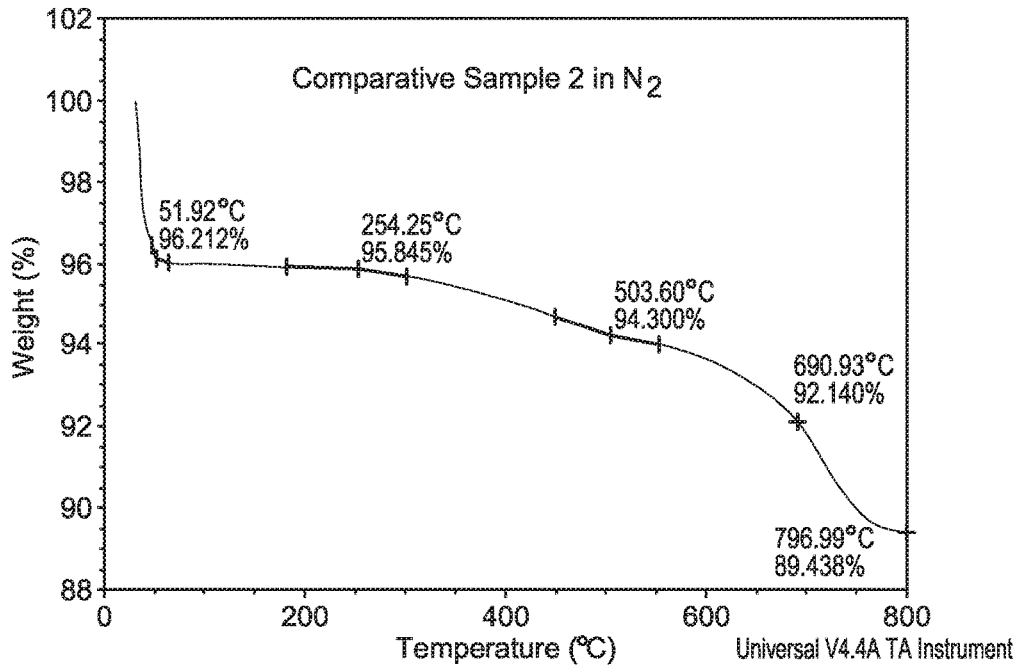
FIG. 8a illustrates TGA data for Comparative Sample 2 in $N_2$.
Figure 8B:
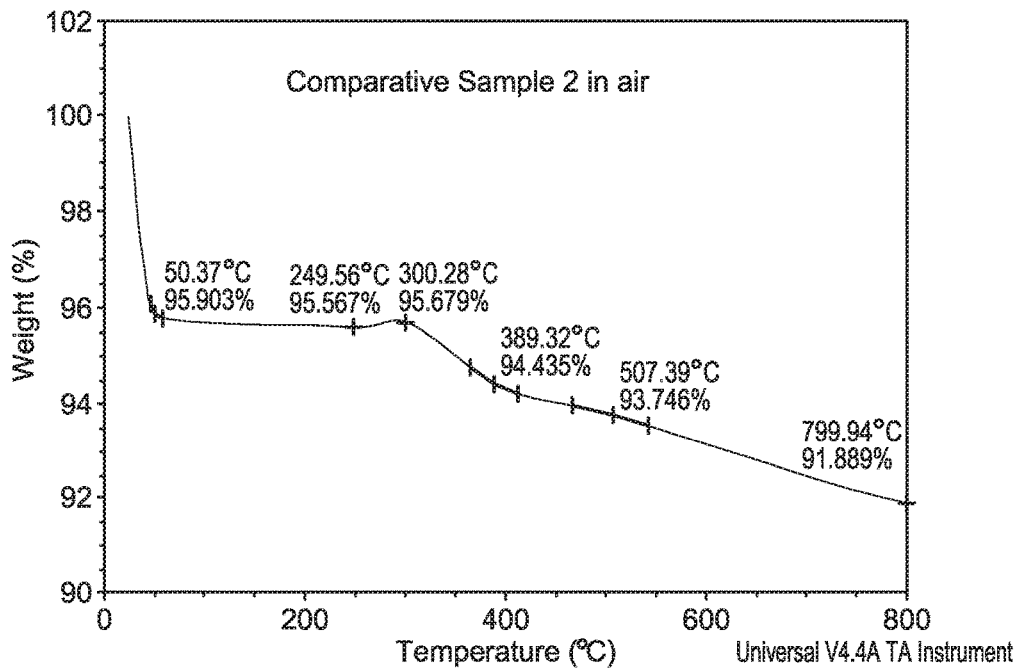
FIG. 8b illustrates TGA data for Comparative Sample 2 in air.

TGA weight loss studies were performed on Comparative Sample 2 in nitrogen and air. FIGS. 8a and 8b display the TGA data for Comparative Sample 2 in nitrogen and air, respectively.

Nitrogen Adsorption/Desorption Analysis

Nitrogen adsorption/desorption analysis was performed on Comparative Sample 2. The surface area, average pore diameter, and pore volume obtained by the nitrogen adsorption/desorption analysis for Sample 1A and Comparative Sample 2 are shown below in Table 1 and FIGS. 3 and 4.

TABLE 1

| Material | BET (m²/g) | Pore Diameter (nm) | Pore Volume (cc/g) |
| --- | --- | --- | --- |
| Comparative Sample 2 | 1520 | 3.02 | 1.07 |
| Sample 1A | 1410 | 3.18 | 0.92 |

SS-NMR-Analysis

Figure 7B:
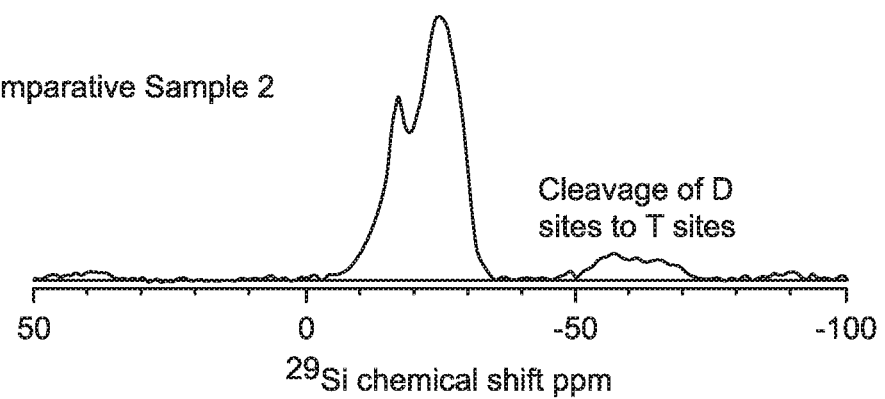
FIG. 7b illustrates a $^{29}$Si MAS NMR spectrum for Comparative Sample 2.

Comparative Sample 2 was characterized with ²⁹Si MAS NMR as shown in FIG. 7b. As shown below in Table 2, Sample 1A had a higher silanol content (i.e., 47%) compared to Comparative Sample 2 (i.e., 41%).

TABLE 2

|  | D₁ | D₂ | T sites | Si(OH)/Si |
| --- | --- | --- | --- | --- |
| Sample 1A (%) | 96 |  | 4 | 47 |
|  | 45.6 | 50.4 |  |  |
| Comparative Sample 2(%) | 89 |  | 11 | 41 |
|  | 34.7 | 54.3 |  |  |

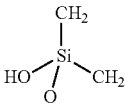

D¹

-continued

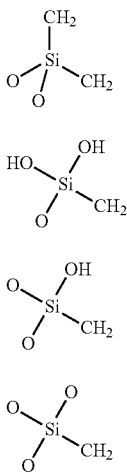

1C. Synthesis using [(EtO)$_2$SiCH$_2$]$_3$ in Acidic Aqueous Medium—without Surfactant.

A 14 g HCl solution with a pH of 2 was made by adding 0.778 mol water and 0.14 mmol HCl. To the solution, 1.0 g (2.52 mmol) of [(EtO)$_2$SiCH$_2$]$_3$ was added producing a solution having the molar composition:

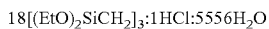
18[(EtO)$_2$SiCH$_2$]$_3$:1HCl:5556H$_2$O which was stirred for 1 day at room temperature (20-25° C.). The solution was transferred to an autoclave and aged at 94° C. for 1 day to produce a gel. The gel was dried in a vacuum at 120° C. overnight (16-24 hours) to produce Sample 3. No surface directing agent or porogen were used.

XRD Analysis

Figure 9:
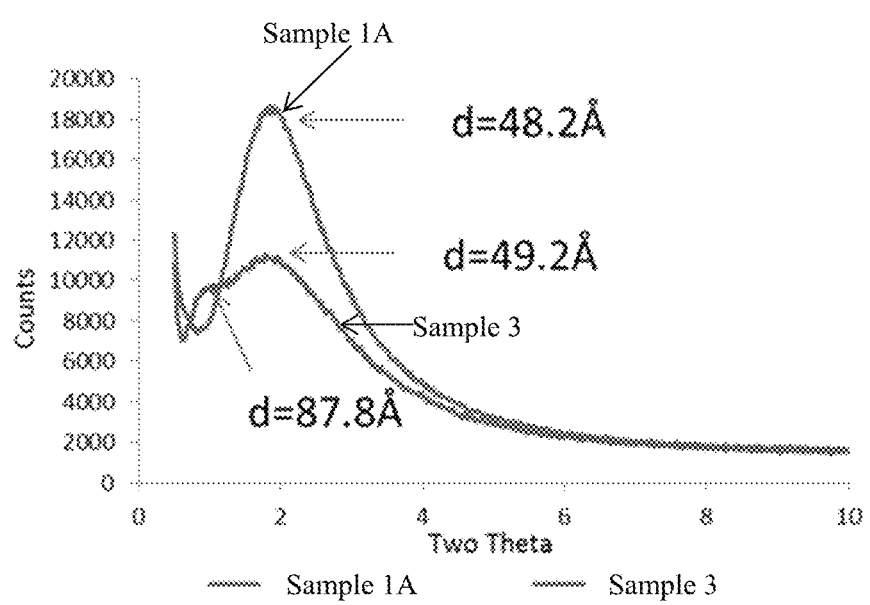
FIG. 9 illustrates an XRD spectrum for Sample 1A and Sample 3.

XRD was performed on Sample 3. A comparison of XRD patterns for Sample 1A and Sample 3 is shown in FIG. 9.

Nitrogen Adsorption/Desorption Analysis

Figure 5:
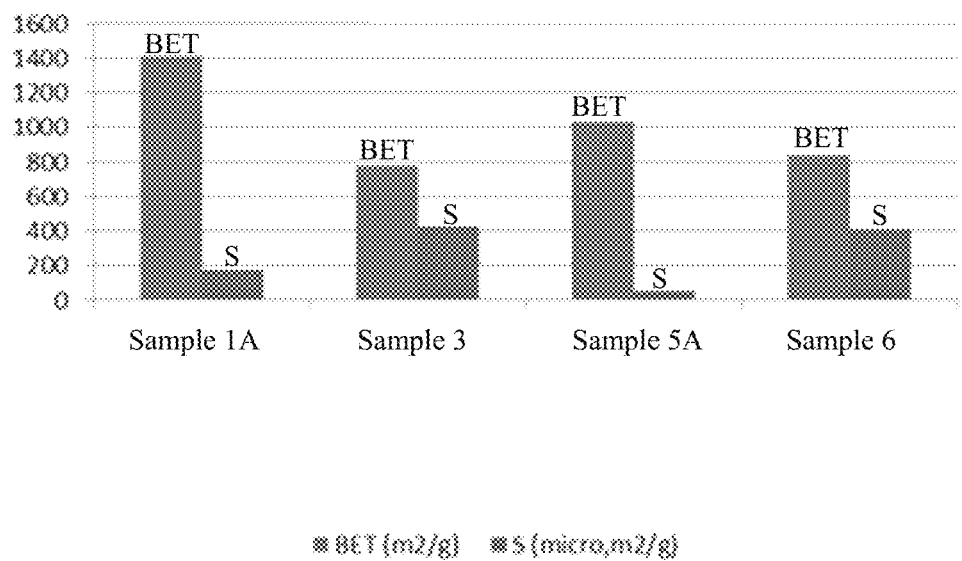
FIG. 5 illustrates comparison of BET surface area and microporous surface area for Sample 1A, Sample 3, Sample 5A and Sample 6.
Figure 6:
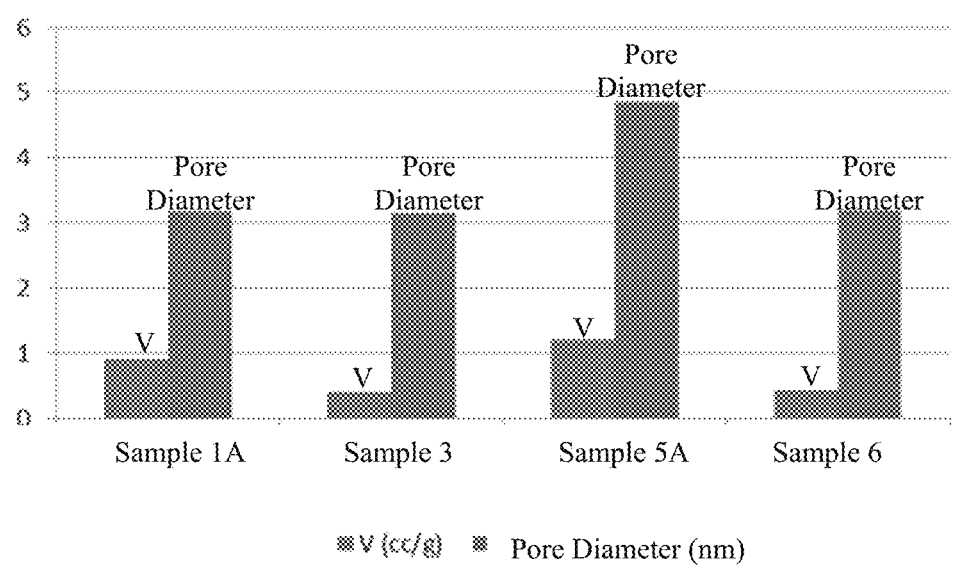
FIG. 6 illustrates comparison of pore volume and pore diameter for Sample 1A, Sample 5A, Sample 6 and Sample 3.

Nitrogen adsorption/desorption analysis was performed on Sample 3. The surface area, microporous surface area, average pore diameter, and pore volume obtained by the nitrogen adsorption/desorption analysis for Sample 3 are shown in FIGS. 5 and 6.

1D. Synthesis Using [(EtO)$_2$SiCH$_2$]$_3$ and [CH$_3$EtOSiCH$_2$]$_3$

A solution with 6.21 g of 30% NH$_4$OH and 7.92 g DI water was made. To the solution, 0.6 g of [(EtO)$_2$SiCH$_2$]$_3$ and 0.306 g of 1,3,5-trimethyl-1,3,5-triethoxy-1,3,5-trisilacyclohexane ([CH$_3$EtOSiCH$_2$]$_3$) was added producing a solution having the molar composition:

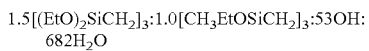
1.5[(EtO)$_2$SiCH$_2$]$_3$:1.0[CH$_3$EtOSiCH$_2$]$_3$:53OH:682H$_2$O which was stirred for 1 day at room temperature (20-25° C.). The solution was transferred to an autoclave and aged at 90° C. for 1 day to produce a gel. The gel was dried in a vacuum at 120° C. overnight (16-24 hours) and Sample 4A was obtained. No structure directing agent or porogen were used.

Nitrogen Adsorption/Desorption Analysis

This above preparation method was repeated, except the relative ratio of [(EtO)$_2$SiCH$_2$]$_3$ (Reagent 1) to [CH$_3$EtOSiCH$_2$]$_3$ (Reagent 2) was varied. Nitrogen adsorption/desorption analysis was performed on each material and the results for each material is given below in Table 3.

TABLE 3

| Material | Reagent 1:Reagent 2 | BET (m$^2$/g) | V (cc/g) | Pore Diameter (nm) |
|---|---|---|---|---|
| Sample 1A | 5:0 | 1410 | 0.915 | 3.18 |
| Sample 4A | 3:2 | 819 | 1.52 | 7.39 |
| Sample 4B | 4:1 | 1100 | 1.14 | 4.17 |
| Sample 4C | 2:3 | 460 | 1.09 | 13.9 |
| Sample 4D | 0:5 | 1.81 | 7.73E−03 | 68.8 |

As Reagent 2 increased, the average pore diameter was observed to increase, which without being bound by theory may be due to Reagent 2 containing less reactive —OR groups compared to Reagent 1. The porosity of the material decreased as Reagent 2 was greater than 60% (mol ratio).

SS-NMR-Analysis

Figure 10:
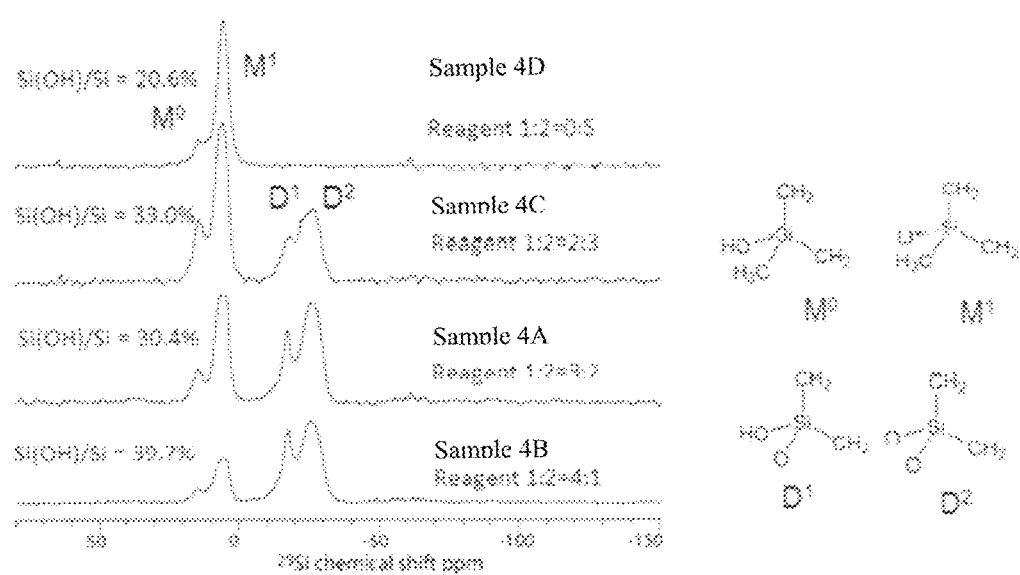
FIG. 10 illustrates a $^{29}$Si MAS NMR spectrum for Sample 4A, Sample 4B, Sample 4C and Sample 4D.

The materials in Table 3 were characterized with $^{29}$Si MAS NMR, as shown in FIG. 10.

Example 2

Organosilica Material Syntheses Using Formula [R$^1$R$^2$SiCH$_2$]$_3$ (Ia) and Formula R$^3$OR$^4$R$^5$R$^6$Si (Va) in Basic or Acidic Media 2A. Synthesis Using [(EtO)$_2$SiCH$_2$]$_3$ and Tetraethylorthosilicate (TEOS) ((EtO)$_4$Si) in Basic Aqueous Medium A solution with 6.21 g of 30% NH$_4$OH (53 mmol NH$_4$OH) and 7.92 g DI water was made. To the solution, 0.8 g (2 mmol) of [(EtO)$_2$SiCH$_2$]$_3$ and 0.625 g (3 mmol) of TEOS was added to produce a solution having the molar composition:

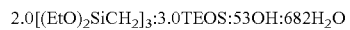
2.0[(EtO)$_2$SiCH$_2$]$_3$:3.0TEOS:53OH:682H$_2$O which was stirred for three days at room temperature (20-25° C.). The solution was transferred to an autoclave and aged at 80° C.-90° C. for 2 days to produce a gel. The gel was dried in a vacuum at 110° C. overnight (16-24 hours) and Sample 5 was obtained. No structure directing agent or porogen was used.

A solution with 6.21 g of 30% NH$_4$OH (53 mmol NH$_4$OH) and 7.92 g DI water was made. To the solution, 3.2 g (8 mmol) of [(EtO)$_2$SiCH$_2$]$_3$ and 2.5 g (12 mmol) of TEOS was added to produce a solution having the molar composition:

8.0[(EtO)$_2$SiCH$_2$]$_3$:12.0TEOS:53OH:682H$_2$O which was stirred for three days at room temperature (20-25° C.). The solution was transferred to an autoclave and aged at 80° C.-90° C. for 2 days to produce a gel. The gel was dried in a vacuum at 110° C. overnight (16-24 hours) and Sample 5A was obtained. No structure directing agent or porogen was used.

XRD Analysis

Figure 11:
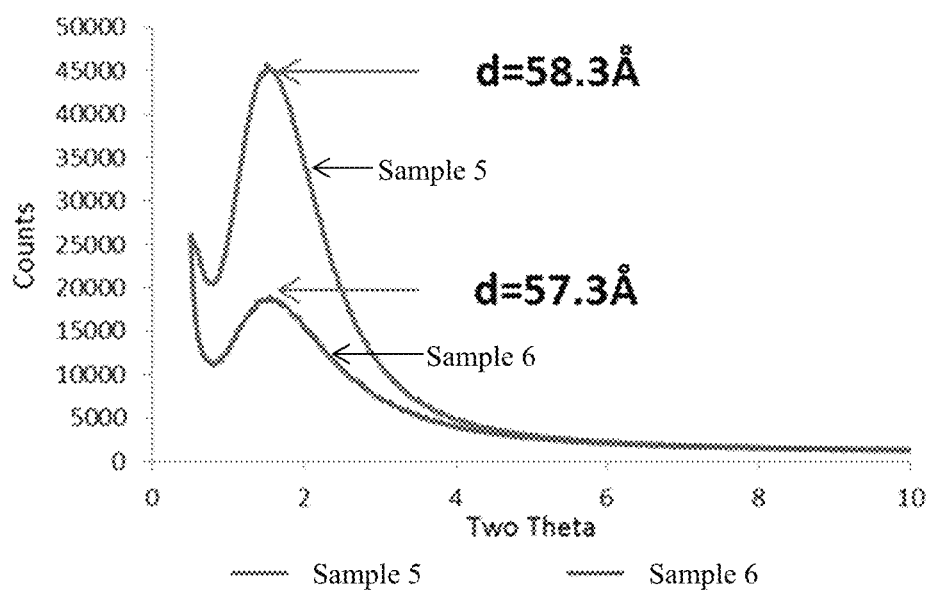
FIG. 11 illustrates an XRD spectrum for Sample 5 and Sample 6.

XRD was performed on Sample 5. The XRD pattern of Sample 5 is shown in FIG. 11.

TGA Analysis

Figure 12:
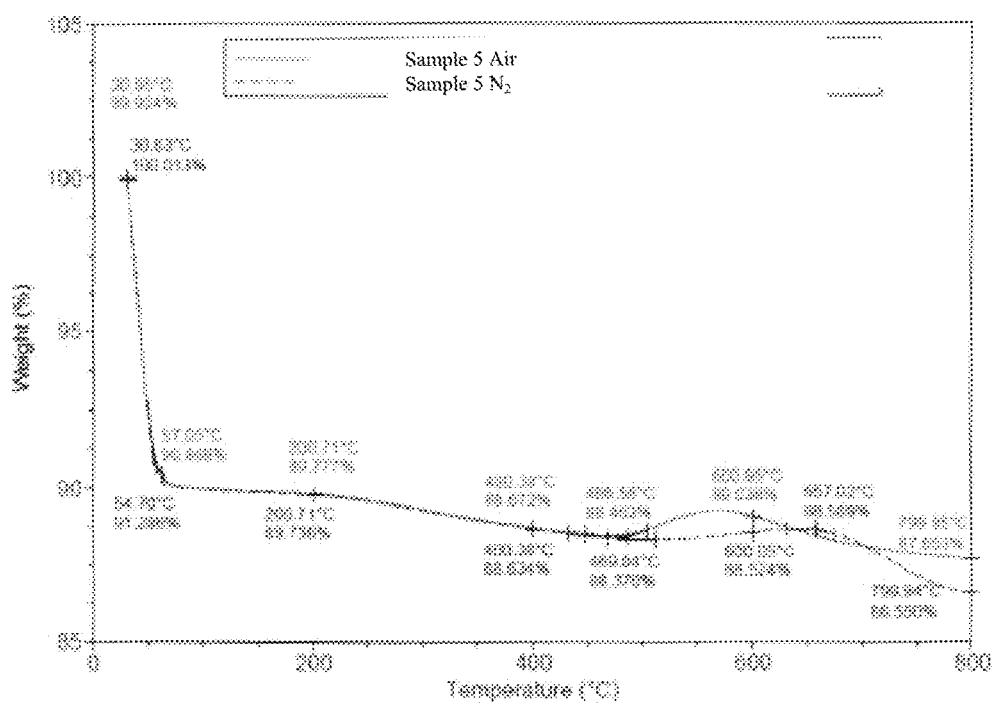
FIG. 12 illustrates TGA data for Sample 5 in air and $N_2$.

TGA weight loss studies were performed on Sample 5 in nitrogen and air. FIG. 12 display the TGA data for Sample 5 in nitrogen and air.

SS-NMR-Analysis

Figure 13:
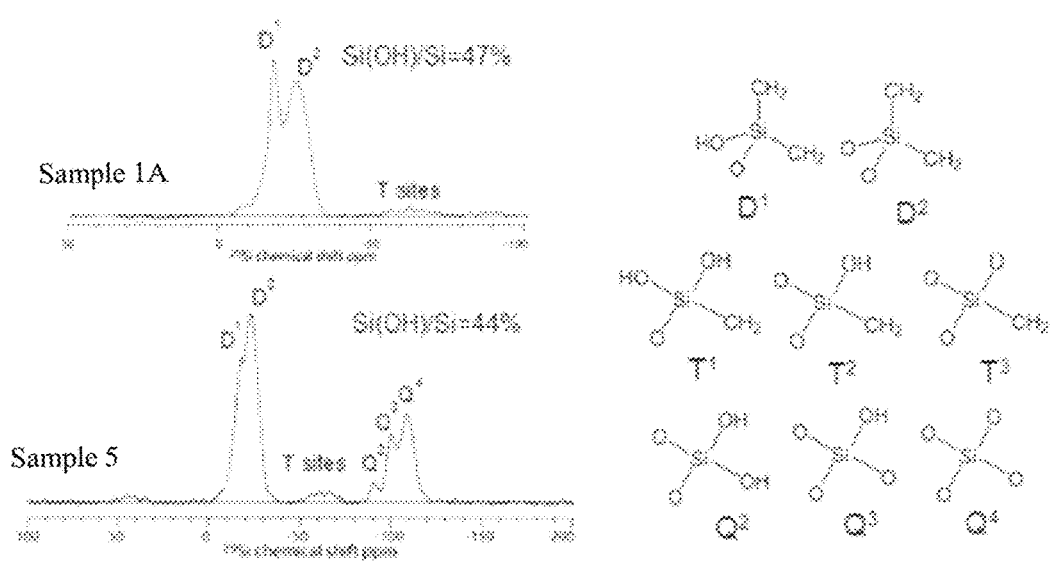
FIG. 13 illustrates a $^{29}$Si MAS NMR spectrum for Sample 1A and Sample 5.

Sample 5 was characterized with $^{29}$Si MAS NMR and compared with Sample 1A as shown in FIG. 13. As shown in FIG. 13, Sample 5 had a silanol content of 44%.

Nitrogen Adsorption/Desorption Analysis

Nitrogen adsorption/desorption analysis was performed on Sample 5 and Sample 5A, and the results are provided below in Table 4 and FIGS. 5 and 6.

TABLE 4

| Material | BET ($m^2/g$) | Pore Diameter (nm) | Pore Volume (cc/g) |
|---|---|---|---|
| Sample 5 | 1430 | 3.42 | 1.21 |
| Sample 5A | 1027 | 4.84 | 1.20 |

2B. Synthesis Using $[(EtO)_2SiCH_2]_3$ and TEOS in Acidic Aqueous Medium

A 14 g HCl solution with a pH of 2 was made by adding 0.778 mol water and 0.14 mmol HCl. To the solution, 0.8 g (2 mmol) of $[(EtO)_2SiCH_2]_3$ and 0.625 g (3 mmol) TEOS was added to produce a solution having the molar composition:

$2.0[(EtO)_2SiCH_2]_3:3.0TEOS:0.14H:778H_2O$ which was stirred for 1 day at room temperature (20-25° C.). The solution was transferred to an autoclave and aged at 94° C. for 1 day to produce a gel. The gel was dried in a vacuum at 120° C. overnight (16-24 hours) to produce Sample 6. No structure directing agent or porogen were used.

XRD Analysis

XRD was performed on Sample 6. The XRD pattern of Sample 6 is shown in FIG. 11.

Nitrogen Adsorption/Desorption Analysis

Nitrogen adsorption/desorption analysis was performed on Sample 6, and the results are provided in FIGS. 5 and 6.

2C. Synthesis Using $[CH_3EtOSiCH_2]_3$ and TEOS

A solution with 6.21 g of 30% $NH_4OH$ (53 mmol $NH_4OH$) and 7.92 g DI water was made. To the solution, 0.612 g (2 mmol) of 1,3,5-trimethyl-1,3,5-triethoxy-1,3,5-trisilacyclohexane ($[CH_3EtOSiCH_2]_3$) and 0.625 g (3 mmoles) of TEOS was added to produce a solution having the molar composition:

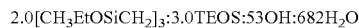
$2.0[CH_3EtOSiCH_2]_3:3.0TEOS:53OH:682H_2O$ which was stirred for 1 day at room temperature (20-25° C.). The solution was transferred to an autoclave and aged at 90° C. for 1 day to produce a gel. The gel was dried in a vacuum at 120° C. overnight (16-24 hours) and Sample 7A was obtained. No structure directing agent or porogen were used.

Nitrogen Adsorption/Desorption Analysis

This above preparation method was repeated, except the relative ratio of TEOS (Reagent 3) to $[CH_3EtOSiCH_2]_3$ (Reagent 2) was varied. Table 5 below is a summary of the $N_2$ adsorption analysis for the materials obtained with varied reagent ratios.

TABLE 5

| Material | (Reagent 3:Reagent 2) | BET ($m^2/g$) | Pore Volume (cc/g) | Pore Diameter (nm) |
|---|---|---|---|---|
| Sample 7A | 3:2 | 471 | 1.9 | 18.6 |
| Sample 7B | 3:4 | 493 | 2.16 | 23.1 |

SS-NMR-Analysis

Figure 14:
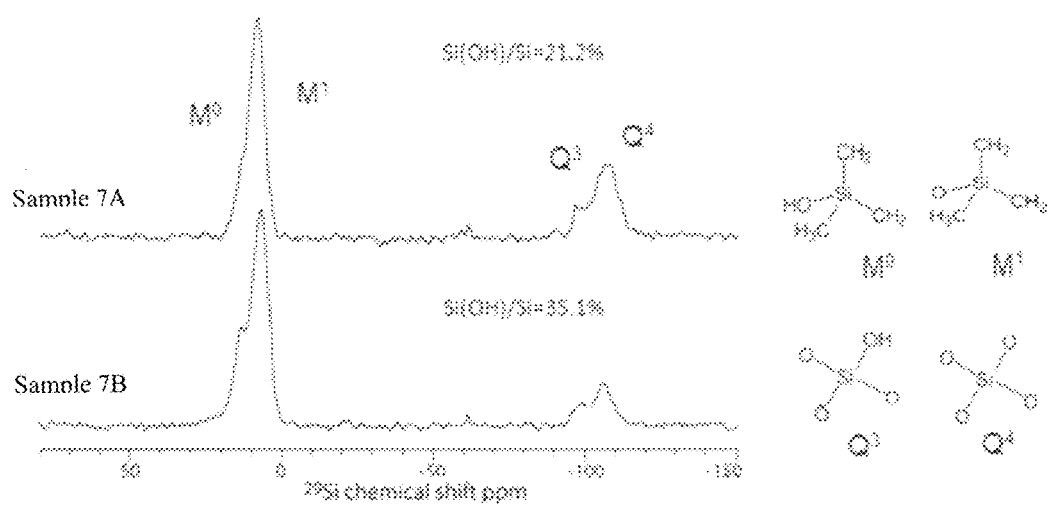
FIG. 14 illustrates a $^{29}$Si MAS NMR spectrum for Sample 7A and Sample 7B.

The materials made by this method were characterized with by $^{29}Si$ MAS NMR, as shown in FIG. 14.

2D. Synthesis using $[(EtO)_2SiCH_2]_3$ and methyltriethoxysilane (MTES) $((EtO)_3CH_3Si)$ A solution with 6.21 g of 30% $NH_4OH$ (53 mmol $NH_4OH$) and 7.92 g DI water was made. To the solution, 0.4 g (1 mmol) of $[(EtO)_2SiCH_2]_3$ and 0.267 g (1.5 mmol) of MTES was added to produce a solution having the molar composition:

$1.0[(EtO)_2SiCH_2]_3:1.5MTES:53OH:682H_2O$ which was stirred for 1 day at room temperature (20-25° C.). The solution was transferred to an autoclave and aged at 90° C. for 1 day to produce a gel. The gel was dried in a vacuum at 120° C. overnight (16-24 hours) and Sample 8A was obtained. No structure directing agent or porogen were used.

Nitrogen Adsorption/Desorption Analysis

This above preparation method was repeated, except the relative ratio of $[(EtO)_2SiCH_2]_3$ (Reagent 1) and of MTES (Reagent 2) was varied. Table 6 below is a summary of the $N_2$ adsorption analysis for the materials obtained with varied reagent ratios.

TABLE 6

| Material | Reagent 1:Reagent 2 | BET ($m^2/g$) | Pore Volume (cc/g) | Pore Diameter (nm) |
|---|---|---|---|---|
| Sample 1A | 5:0 | 1410 | 0.915 | 3.18 |
| Sample 8A | 2:3 | 821 | 1.06 | 4.5 |
| Sample 8B | 4:1 | 1130 | 1.0 | 3.59 |
| Sample 8C | 3:2 | 1040 | 1.05 | 3.89 |

Example 3

Organosilica Material Syntheses Using Formula $[R^1R^2SiCH_2]_3$ (Ia) Formula $R^3OR^4R^5R^6Si$ (Va), and/or Formula $Z^{18}Z^{19}Z^{20}Si—R—SiZ^{18}Z^{19}Z^{20}$ (VIa)

3A. Synthesis Using $[(EtO)_2SiCH_2]_3$ and $CH_3(EtO)_2Si—CH_2CH_2—Si(EtO)_2CH_3$.

A solution with 6.21 g of 30% $NH_4OH$ (53 mmol $NH_4OH$) and 7.9 g DI water was made. To the solution, 0.8 g (2 mmol) of $[(EtO)_2SiCH_2]_3$ and 0.88 g (3 mmol) 1,2-bis (methyldiethyoxysilyl)ethane ($CH_3(EtO)_2Si—CH_2CH_2—Si(EtO)_2CH_3$) was added to produce a solution having the molar composition:

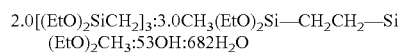
$2.0[(EtO)_2SiCH_2]_3:3.0CH_3(EtO)_2Si—CH_2CH_2—Si(EtO)_2CH_3:53OH:682H_2O$ which was stirred for 1 day at room temperature (20-25° C.). The solution was transferred to an autoclave and aged at 80° C.-90° C. for 1 day to produce a gel. The gel was dried in a vacuum at 110° C. overnight (16-24 hours) and Sample 9 was obtained. No structure directing agent or porogen were used.

XRD Analysis

Figure 15:
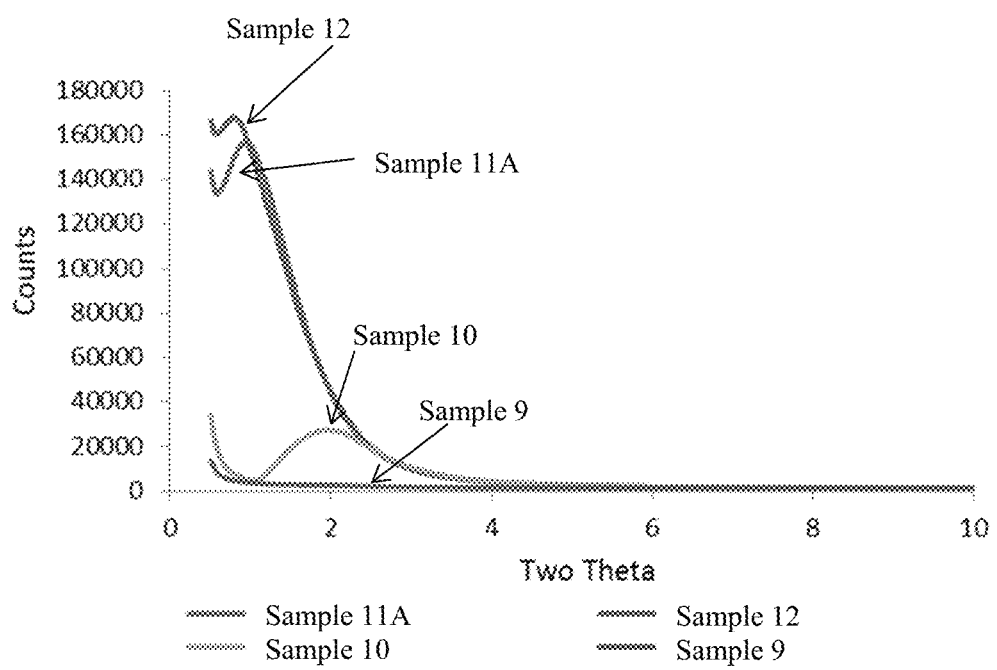
FIG. 15 illustrates an XRD spectrum for Sample 9, Sample 10, Sample 11A, and Sample 12.

XRD was performed on Sample 9. The XRD pattern of Sample 9 is shown in FIG. 15.

Nitrogen Adsorption/Desorption Analysis

Nitrogen adsorption/desorption analysis was performed on Sample 9, and the results are provided in Table 7.

3B. Synthesis using $[(EtO)_2SiCH_2]_3$ and $(EtO)_3Si—CH_2—Si(EtO)_3$

A solution with 6.21 g of 30% $NH_4OH$ (53 mmol $NH_4OH$) and 7.9 g DI water was made. To the solution, 0.8 g (2 mmol) of $[(EtO)_2SiCH_2]_3$ and 1.02 g (3 mmol) of bis(triethoxysilyl)methane $((EtO)_3Si—CH_2—Si(EtO)_3)$ was added to produce a solution having the molar composition:

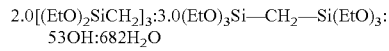
$2.0[(EtO)_2SiCH_2]_3:3.0(EtO)_3Si—CH_2—Si(EtO)_3:53OH:682H_2O$ which was stirred for 1 day at room temperature (20-25° C.). The solution was transferred to an autoclave and aged at 80° C.-90° C. for 1 day to produce a gel. The gel was dried in a vacuum at 110° C. overnight (16-24 hours) and Sample 10 was obtained. No structure directing agent or porogen were used.

XRD Analysis

XRD was performed on Sample 10. The XRD pattern of Sample 10 is shown in FIG. 15.

Nitrogen Adsorption/Desorption Analysis

Nitrogen adsorption/desorption analysis was performed on Sample 10, and the results are provided in Table 7.

3C. Synthesis Using TEOS and $(EtO)_3Si$—$CH_2$—$Si(EtO)_3$

A solution with 6.21 g of 30% $NH_4OH$ (53 mmoles $NH_4OH$) and 7.92 g DI water was made. To the solution, 1.7 g (5 mmol) of bis(triethoxysilyl)methane (($EtO)_3Si$—$CH_2$—$Si(EtO)_3$) and 0.416 g (2 mmol) of TEOS were added to produce a solution having the molar composition:

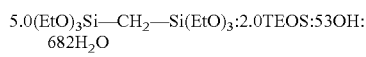
5.0(EtO)$_3$Si—CH$_2$—Si(EtO)$_3$:2.0TEOS:53OH: 682H$_2$O which was stirred for 1 day at room temperature (20-25° C.). The solution was transferred to an autoclave and aged at 80° C.-90° C. for 1 day to produce a gel. The gel was dried in a vacuum at 110° C. overnight (8-16 hours) and Sample 11A was obtained. No structure directing agent or porogen were used.

Two more preparations with different ratios of reagents were also made, one with a $(EtO)_3Si$—$CH_2$—$Si(EtO)_3$:TEOS molar ratio of 4:4 to obtain Sample 11B and another with a $(EtO)_3Si$—$CH_2$—$Si(EtO)_3$:TEOS molar ratio of 3:6 to obtain Sample 11C.

XRD Analysis

XRD was performed on Sample 11A. The XRD pattern of Sample 11A is shown in FIG. 15.

Nitrogen Adsorption/Desorption Analysis

Nitrogen adsorption/desorption analysis was performed on Sample 11A, and the results are provided in Table 7.

3D. Synthesis Using $[(EtO)_2SiCH_2]_3$ and $(EtO)_3Si$—$CH=CH$—$Si(EtO)_3$

A solution with 12.42 g of 30% $NH_4OH$ (106 mmol $NH_4OH$) and 15.8 g DI water was made. To the solution, 1.6 g (4 mmol) of $[(EtO)_2SiCH_2]_3$ and 0.352 g (1 mmol) 1,2-bis(triethoxysilyl)ethylene (($EtO)_3Si$—$CH=CH$—$Si(EtO)_3$) was added to produce a solution having the molar composition:

4.0[(EtO)$_2$SiCH$_2$]$_3$:1.0(EtO)$_3$Si—CH=CH—Si(EtO)$_3$:106OH:1364H$_2$O which was stirred for 1 day at room temperature (20-25° C.). The solution was transferred to an autoclave and aged at 80° C.-90° C. for 1 day to produce a gel. The gel was dried in a vacuum at 110° C. overnight (8-16 hours) and Sample 12 was obtained. No structure directing agent or porogen were used.

XRD Analysis

XRD was performed on Sample 12. The XRD pattern of Sample 12 is shown in FIG. 15.

Nitrogen Adsorption/Desorption Analysis

Nitrogen adsorption/desorption analysis was performed on Sample 12, and the results are provided in Table 7.

TABLE 7

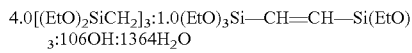

| Material | BET (m2/g) | S (m2/g, micro) | Pore Diameter (nm) | Pore Volume (cc/g) |
|---|---|---|---|---|
| Sample 9 | 551 | 233 | 8.4 | 0.76 |
| Sample 10 | 1270 | 512 | 3.35 | 0.96 |
| Sample 11A | 870 | 0 | 3.83 | 0.84 |
| Sample 12 | 1030 | 0 | 3.69 | 1.02 |

Example 4

Organosilica Material Syntheses using Formula $[R^1R^2SiCH_2]_3$ (Ia) and Nitrogen-Containing Monomers A solution with 6.21 g of 30% $NH_4OH$ (53 mmol $NH_4OH$) and 7.9 g DI water was made. To the solution, 0.8 g (2 mmol) of $[(EtO)_2SiCH_2]_3$ and an amount of Reagent 2 was added to produce a solution having the molar composition:

2.0[(EtO)$_2$SiCH$_2$]$_3$:x Reagent 2:53OH:682H$_2$O which was stirred for 1 day at room temperature (20-25° C.). The solution was transferred to an autoclave and aged at 80° C.-90° C. for 1 day to produce a gel. The gel was dried in a vacuum at 110° C. overnight (8-16 hours) and Sample 12 was obtained. No structure directing agent or porogen were used.

The above synthesis was performed with the following reagents in Table 8 to obtain Samples 13, 14, 15 and 21.

The above synthesis was performed with the following reagents in Table 8 to obtain Samples 16, 17, 18 and 19 except 1.6 g of $[(EtO)_2SiCH_2]_3$, 12.4 g of 30% $NH_4OH$ and 15.8 g DI water were used for the preparation.

The above synthesis was performed with the following reagents in Table 8 to obtain Sample 20 except 3.2 g of $[(EtO)_2SiCH_2]_3$, 24.8 g of 30% $NH_4OH$ and 31.6 g of DI water were used for the preparation.

TABLE 8

| Material | Reagent 2 | Reagent 2 Amount (g) | Reagent 1:Reagent 2 Molar ratio |
|---|---|---|---|
| Sample 13 | N,N'-bis[(3-trimethoxysilyl)propyl]ethylenediamine | 0.192 | 2:0.5 |
| Sample 14 | bis[(methyldiethoxysilyl)propyl]amine | 0.183 | 2:0.5 |
| Sample 15 | bis[(methyldimethoxysilyl)propyl]-N-methylamine | 0.162 | 2:0.5 |
| Sample 16 | (N,N-dimethylaminopropyl)trimethoxysilane | 1.24 | 2:3 |
| Sample 17 | N-(2-aminoethyl)-3-aminopropyltriethoxysilane | 1.58 | 2:3 |
| Sample 18 | 4-methyl-1-(3-triethoxysilylpropyl)-piperazine | 1.83 | 2:3 |
| Sample 19 | 4-(2-(triethoxysily)ethyl)pyridine | 0.271 | 2:0.5 |
| Sample 20 | 1-(3-(triethoxysilyl)propyl)-4,5-dihydro-1H-imidazole | 0.553 | 2:0.5 |
| Sample 21 | (3-aminopropyl)triethoxysilane | 0.22 | 2:0.5 |

XRD Analysis

Figure 16:
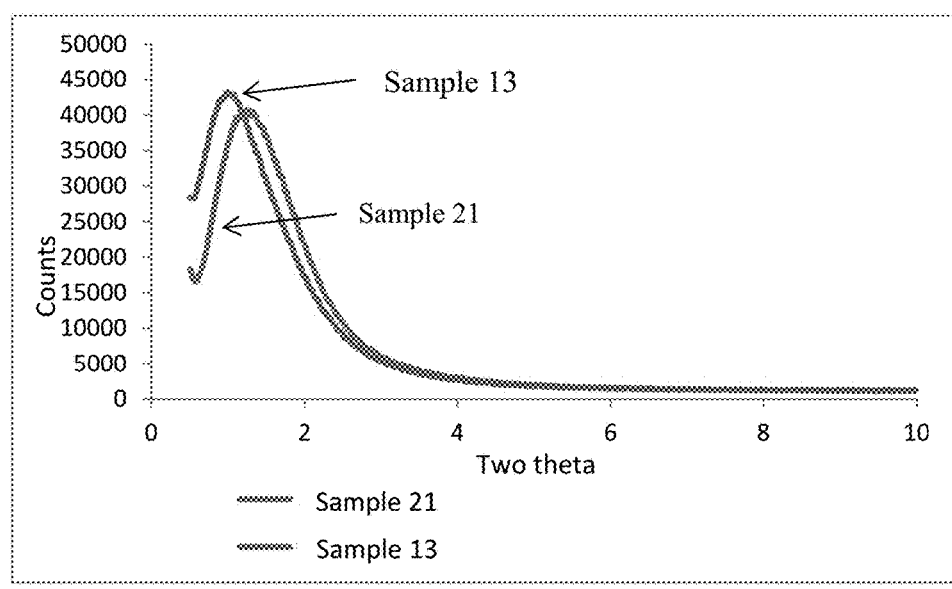
FIG. 16 illustrates an XRD spectrum for Sample 13 and Sample 21.

XRD was performed on Samples 13 and 21. The XRD patterns of Samples 13 and 21 are shown in FIG. 16.

Nitrogen Adsorption/Desorption Analysis

Figure 17:
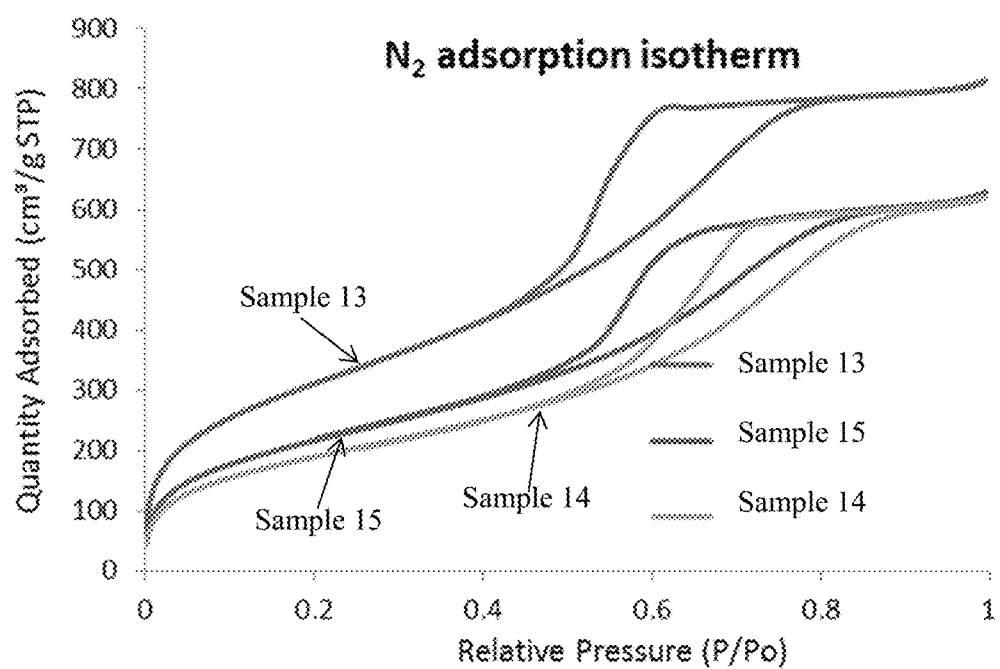
FIG. 17 illustrates $N_2$ adsorption isotherms for Sample 13, Sample 14 and Sample 15.
Figure 18:
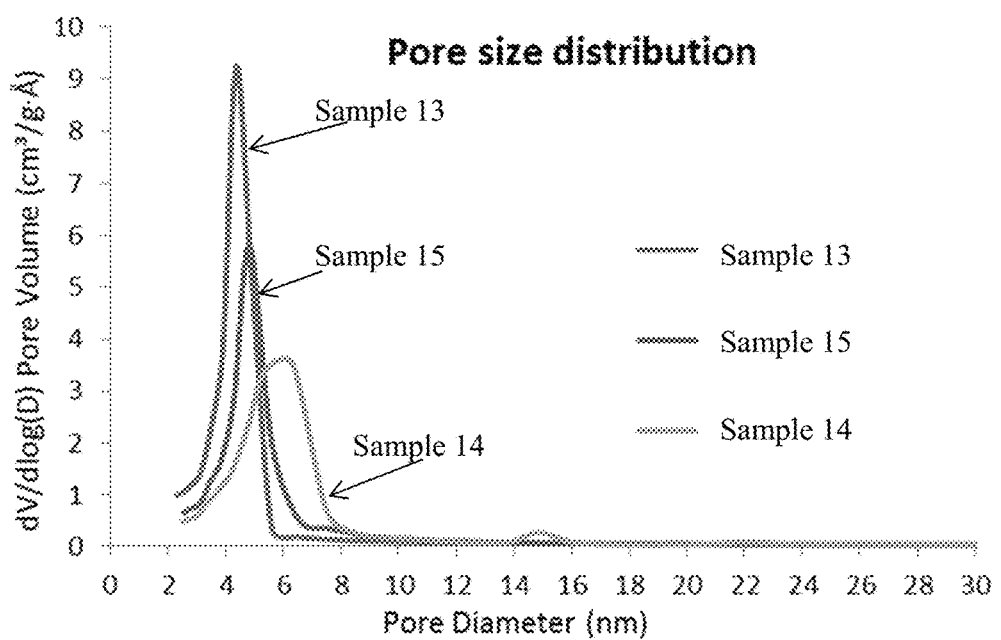
FIG. 18 illustrates pore diameter distribution for Sample 13, Sample 14 and Sample 15.

Nitrogen adsorption/desorption analysis was performed on Samples 13, 14 and 15, and the results are provided in Table 9 and FIGS. 17 and 18.

TABLE 9

| Material | BET (m²/g) | Pore Diameter (nm) | Pore Volume (cc/g) |
|---|---|---|---|
| Sample 13 | 1127 | 4.11 | 1.26 |
| Sample 14 | 691 | 5 | 0.96 |
| Sample 15 | 787 | 4.56 | 0.97 |

Example 5

Organosilica Material Syntheses Using Formula [R$^1$R$^2$SiCH$_2$]$_3$ (Ia) and Trivalent Metal Oxides 5A. Synthesis Using [(EtO)$_2$SiCH$_2$]$_3$ and Aluminum-Tri-Sec-Butoxide A solution with 39.6 g DI water (3410 mmol H$_2$O) and 31.15 g 30 wt % NH$_4$OH (265 mmol NH$_4$OH) was made. To the solution, 10 g (25 mmol) of [(EtO)$_2$SiCH$_2$]$_3$ (Reagent 1) and 0.37 g (1.5 mmol) aluminum-tri-sec-butoxide (Reagent 2) was added to produce a solution having the molar composition:

25.0[(EtO)$_2$SiCH$_2$]$_3$:1.5 aluminum-tri-sec-butoxide:
265OH:3410H$_2$O which was stirred at 23-25° C. for 1 day. The Si/Al ratio between Reagent 1 and Reagent 2 was 50:1. The solution was transferred to an autoclave and aged at 90° C. for 1 day to produce a gel. The gel was dried in a vacuum at 120° C. for 1 day and Sample 22A was obtained. No surface directing agent or porogen were used.

The procedure was repeated except 1.845 g (7.5 mmol) aluminum-tri-sec-butoxide was added instead of 0.37 g (1.5 mmol) aluminum-tri-sec-butoxide to obtain Sample 22B. The Si/Al ratio between Reagent 1 and Reagent 2 was 10:1.

XRD Analysis

Figure 19:
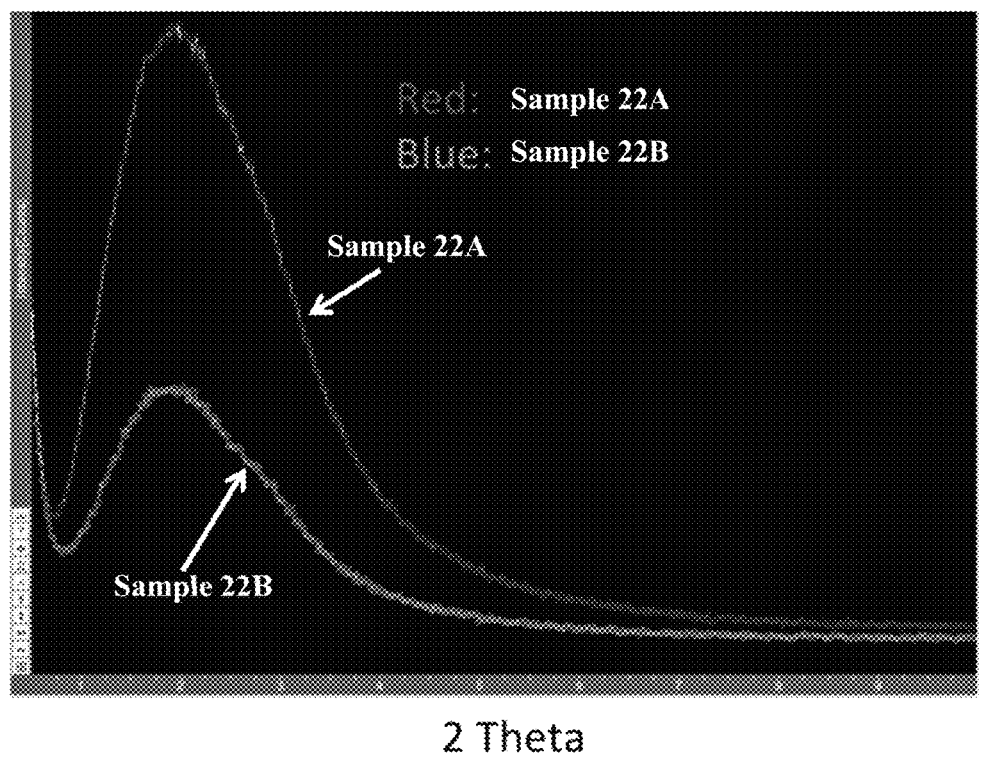
FIG. 19 illustrates an XRD spectrum for Sample 22A and Sample 22B.

XRD was performed on Samples 22A and 22B. The XRD pattern of Samples 22A and 22B is shown in FIG. 19.

Nitrogen Adsorption/Desorption Analysis

Nitrogen adsorption/desorption analysis was performed on Samples 22A and 22B, and the results are provided in Table 10.

TABLE 10

| Material | Si/Al for Reagent 1:Reagent 2 | BET (m$^2$/g) | SA (micro, m$^2$/g) | V (cc/g) | Pore Diameter (nm) |
|---|---|---|---|---|---|
| Sample 22A | 50 | 1273 | 646 | 0.679 | 2.13 |
| Sample 22B | 10 | 578 | 489 | 0.265 | 1.83 |

A highly porous material with more mesoporous structure was achieved when Si/Al ratio increases from 10 to 50.

SS-NMR-Analysis

Figure 20:
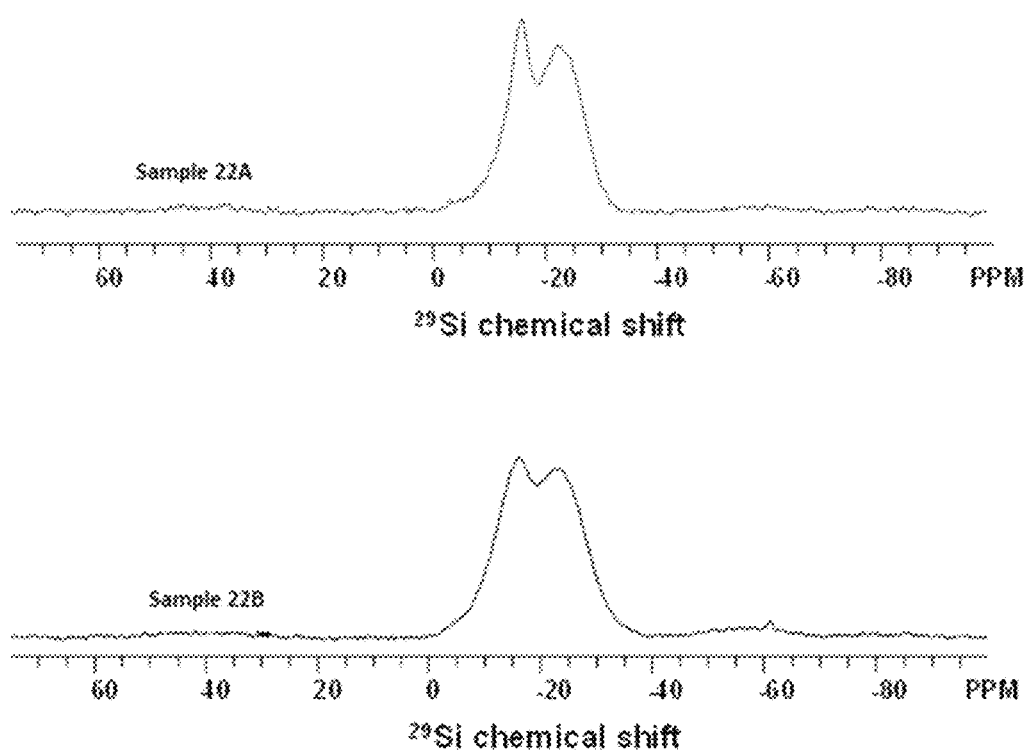
FIG. 20 illustrates a $^{29}$Si MAS NMR spectrum for sample 22A and 22B.
Figure 21:
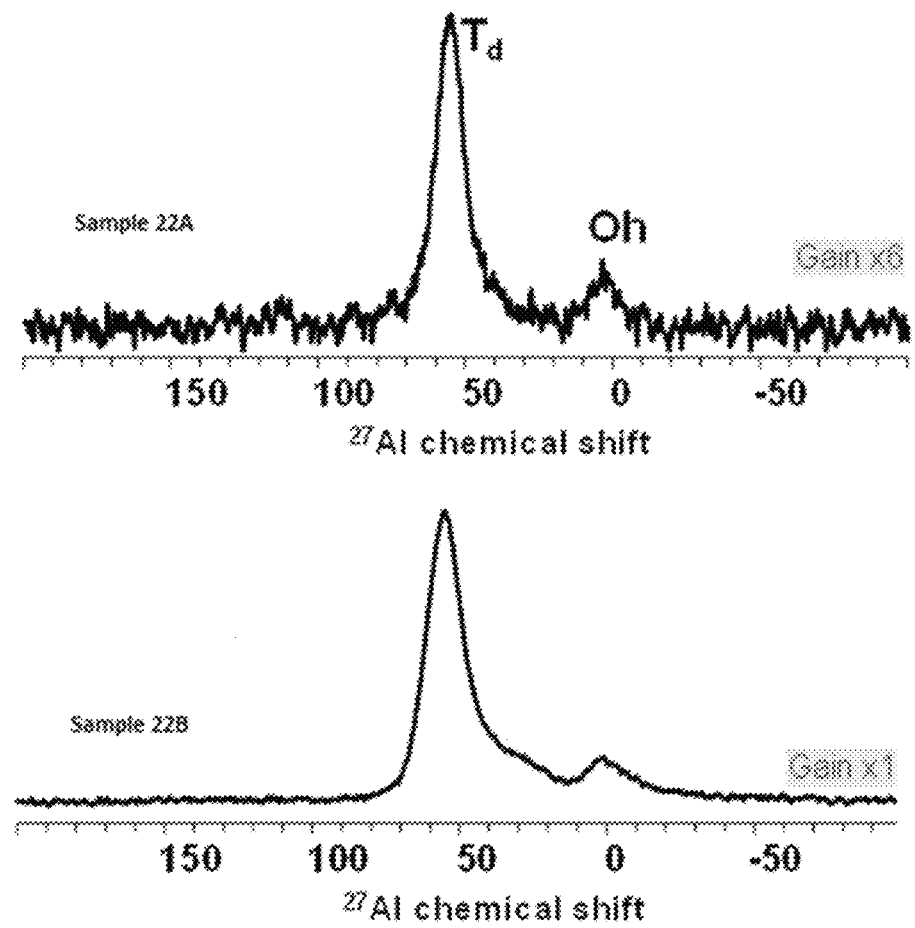
FIG. 21 illustrates a $^{29}$Al MAS NMR spectrum for sample 22A and 22B.
Figure 22:
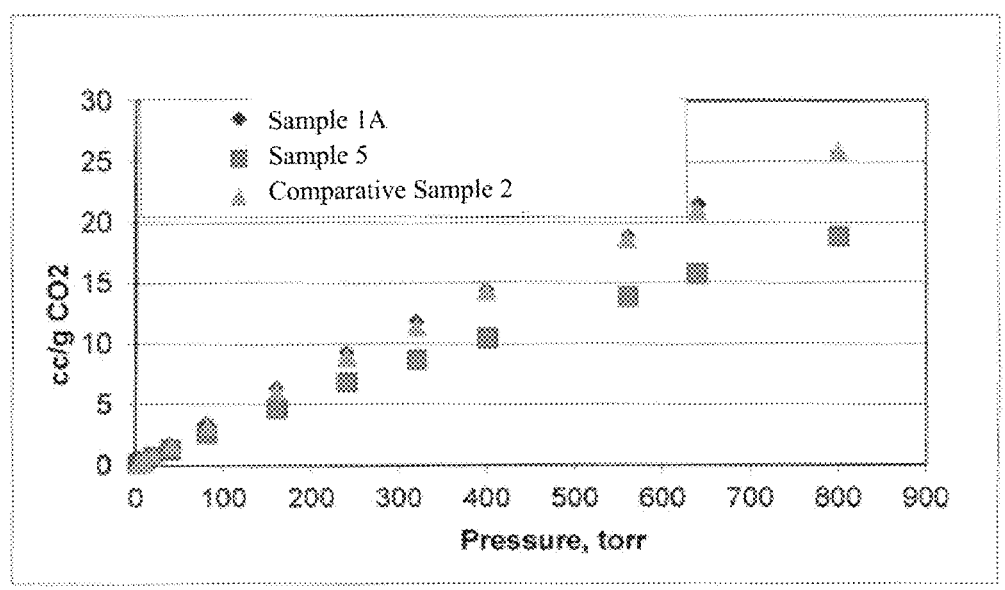
FIG. 22 illustrates $CO_2$ adsorption isotherms for Sample 1A, Sample 5 and Comparative Sample 2.

Samples 22A and 22B were characterized with $^{29}$Si MAS NMR and $^{27}$Al MAS NRM, as shown in FIGS. 20 and 21, respectively.

5B. Surface Acidity Analysis

Surface acidity analysis was used to determine the acid strength of the tetrahedral aluminums in Sample 22A and Sample 22B. Table 11 shows the results of alpha measurement, collidine adsorption, and TPAD.

TABLE 11

| Material | Si/Al for Reagent 1: Reagent 2 | BET (m$^2$/g) | V (cc/g) | Alpha Value | Collidine Adsoprtion (µmoles/g) | TPAD (meq/g) |
|---|---|---|---|---|---|---|
| Sample 22A | 50 | 1273 | 0.68 | 6 | 67 | 0.12 |
| Sample 22B | 10 | 578 | 0.27 | 5 | 90 | 0.61 |

As can be seen from the data in Table 11, the materials show some activity in the hexane cracking reaction. The alpha value measures the cracking activity of the material compared to an amorphous silica-alumina tested under the same conditions. The cracking activity increases with the number of acid sites as well as with their strength. Despite the big difference in collidine capacity as well as the meq/g of ammonia desorbed in the TPAD experiment, the alpha value of the two materials is very similar.

The data indicate that the number of sites accessible to collidine and ammonia is very high relative to what is observed for zeolites.

Example 8

CO$_2$ Isotherms

CO$_2$ adsorption isotherms were measured for Sample 1A, Comparative Sample 2, and Sample 5, as shown in FIG. 21. Sample 1A has similar CO$_2$ uptake compared to the Comparative Sample 2.

What is claimed is:

1. An organosilica material, which is a polymer of at least one trivalent metal oxide monomer and at least one independent monomer of Formula [Z$^1$OZ$^2$OSiCH$_2$]$_3$ (I), wherein Z$^1$ represents a hydrogen atom, a C$_1$-C$_4$ alkyl group, a bond to a silicon atom of another monomer, or a combination thereof, and Z$^2$ represents a hydrogen atom, a C$_1$-C$_4$ alkyl group, a bond to a silicon atom of another monomer, or a combination thereof, wherein the organosilica material has an X-ray diffraction pattern with one peak between 1 and 3 degrees 2θ and no peaks in the range of from 3 to 20 degrees 2θ.

2. The organosilica material of claim 1, wherein Z$^1$ represents a hydrogen atom, a C$_1$-C$_2$ alkyl group, a bond to a silicon atom of another monomer, or a combination thereof, and Z$^2$ represents a hydrogen atom, a C1-C2 alkyl group, a bond to a silicon atom of another monomer, or a combination thereof.

3. The organosilica material of claim 1, wherein Z$^1$ represents a hydrogen atom, ethyl, a bond to a silicon atom of another monomer, or a combination thereof, and Z$^2$ represents a hydrogen atom, ethyl, a bond to a silicon atom of another monomer, or a combination thereof.

4. The organosilica material of claim 1, wherein the at least one trivalent metal oxide monomer is
   (i) an independent unit of formula M$^1$(OZ$^3$)$_3$ (II), wherein M$^1$ represents a Group 13 metal and Z$^3$ represents a hydrogen atom, a C$_1$-C$_6$ alkyl, a bond to a silicon atom of another monomer, or a combination thereof; or
   (ii) an independent unit of formula (Z$^4$O)$_2$M$^2$-O—Si(OZ$^5$)$_3$ (III), wherein M$^2$ represents a Group 13 metal and Z$^4$ represents a hydrogen atom, a C$_1$-C$_6$ alkyl group, a bond to a silicon atom of another monomer, or a combination thereof, and Z$^5$ represents a hydrogen atom, a C$_1$-C$_6$ alkyl group, a bond to a silicon atom of another monomer, or a combination thereof.

5. The organosilica material of claim 4, wherein at least one unit of formula (II) is present, wherein M$^1$ is Al or B and Z$^3$ represents a hydrogen atom, a C$_1$-C$_4$ alkyl group, a bond to a silicon atom or another monomer, or a combination thereof.

6. The organosilica material of claim 4, wherein at least one unit of formula (III) is present, wherein M$^2$ is Al or B; and Z$^4$ represents a hydrogen atom, a C$_1$-C$_4$ alkyl group, a bond to a silicon atom of another monomer, or a combination thereof.

7. The organosilica material of claim 4, wherein the at least one other trivalent metal oxide monomer is the independent unit of formula M$^1$(OZ$^3$)$_3$ (II), wherein M$^1$ is a Group 13 metal and $Z^3$ represents a combination of a hydrogen atom and a bond to a silicon atom of another monomer.

8. The organosilica material of claim 4, wherein the at least one other trivalent metal oxide monomer is an independent unit of formula $M^1(OZ^3)_3$ (II), wherein $M^1$ is Al and $Z^3$ represents a combination of a hydrogen atom and a bond to a silicon atom of another monomer.

9. The organosilica material of claim 1 further comprising a monomer selected from the group consisting of:
  (i) an independent unit of formula $[Z^6OZ^7SiCH_2]_3$ (IV), wherein $Z^6$ represents a hydrogen atom, a $C_1$-$C_4$ alkyl group, a bond to a silicon atom of another monomer, or a combination thereof, and $Z^7$ represents a hydroxyl group, a $C_1$-$C_6$ alkyl group, an oxygen atom bonded to a silicon atom of another monomer, or a combination thereof;
  (ii) an independent unit of formula $Z^8OZ^9Z^{10}Z^{11}Si$ (V), wherein $Z^8$ represents a hydrogen atom or a $C_1$-$C_4$ alkyl group, a bond to a silicon atom of another monomer, or a combination thereof; $Z^9$ is selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroaralkyl group, a nitrogen-containing optionally substituted heterocycloalkyl group, an oxygen atom bonded to a silicon atom of another monomer, or a combination thereof; $Z^{10}$ is selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroaralkyl group, a nitrogen-containing optionally substituted heterocycloalkyl group, an oxygen atom bonded to a silicon atom of another monomer, or a combination thereof; and $Z^{11}$ is selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroaralkyl group, a nitrogen-containing optionally substituted heterocycloalkyl group, an oxygen atom bonded to a silicon atom of another monomer, or a combination thereof; and
  (iii) an independent unit of formula $Z^{12}Z^{13}Z^{14}Si$—R—$SiZ^{12}Z^{13}Z^{14}$ (VI), wherein $Z^{12}$ represents a hydroxyl group, a $C_1$-$C_4$ alkoxy group, an oxygen atom bonded to a silicon atom of another comonomer, or a combination thereof, $Z^{13}$ represents a hydroxyl group, a $C_1$-$C_4$ alkoxy group, a $C_1$-$C_4$ alkyl group, an oxygen bonded to a silicon atom of another monomer, or a combination thereof; Z14 represents a hydroxyl group, a $C_1$-$C_4$ alkoxy group, a $C_1$-$C_4$ alkyl group, an oxygen bonded to a silicon atom of another monomer, or a combination thereof; and R is selected from the group consisting of a $C_1$-$C_8$ alkylene group, a $C_2$-$C_8$ alkenylene group, a $C_2$-$C_8$ alkynylene group, a nitrogen-containing $C_2$-$C_{10}$ alkylene group, an optionally substituted $C_6$-$C_{20}$ aralkyl and an optionally substituted $C_4$-$C_{20}$ heterocycloalkyl group; and
  (iv) a combination thereof.

10. The organosilica material of claim 1, wherein the organosilica has an average pore diameter between about 1.5 nm and about 20.0 nm.

11. The organosilica material of claim 1, wherein the organosilica material has a total surface area of about 200 $m^2/g$ to about 2500 $m^2/g$.

12. The organosilica material of claim 1, wherein the organosilica material has a pore volume about 0.1 $cm^3/g$ to about 5.0 $cm^3/g$.

13. The organosilica material of claim 1, further comprising at least one catalytic metal incorporated within the pores of the material.

14. The organosilica material of claim 13, wherein the catalytic metal is selected from the group consisting of a Group 6 element, a Group 8 element, a Group 9 element, a Group 10 element and a combination thereof.

15. The organosilica material of claim 14, wherein the catalytic metal is Group 10 element.

16. The organosilica material of claim 14, wherein the catalytic metal is the Group 10 element of palladium.

17. The organosilica material of claim 1 made using no added structure directing agent or porogen.

18. The organosilica material of claim 1, wherein $Z^1$ represents a combination of a hydrogen atom and a bond to a silicon atom of another monomer and $Z^2$ represents a combination of a hydrogen atom and a bond to a silicon atom of another monomer.

19. The organosilica material of claim 1, further comprising an independent unit of formula $Z^8OZ^9Z^{10}Z^{11}Si$ (V), wherein $Z^8$ represents a combination of a hydrogen atom and a bond to a silicon atom of another monomer, $Z^9$ represents a combination of a hydroxyl group and a bond to an oxygen atom bonded to a silicon atom of another monomer, $Z^{10}$ represents a combination of a hydroxyl group and a bond to an oxygen atom bonded to a silicon atom of another monomer, and $Z^{11}$ represents a combination of a hydroxyl group and a bond to an oxygen atom bonded to a silicon atom of another monomer.

* * * * *